US009296795B2

(12) United States Patent
Pavliak et al.

(10) Patent No.: US 9,296,795 B2
(45) Date of Patent: *Mar. 29, 2016

(54) POLYSACCHARIDE-STAPHYLOCOCCAL SURFACE ADHESIN CARRIER PROTEIN CONJUGATES FOR IMMUNIZATION AGAINST NOSOCOMIAL INFECTIONS

(75) Inventors: Viliam Pavliak, Montebello, NY (US); Steven Morris Baker, Highland Mills, NY (US); Subramonia Padmanaba Pillai, Pomona, NY (US)

(73) Assignees: WYETH HOLDINGS, LLC., New York, NY (US); INHIBITEX, INC., Alpharetta, GA (US)

( * ) Notice: Subject to any disclaimer, the term of this patent is extended or adjusted under 35 U.S.C. 154(b) by 1081 days.

This patent is subject to a terminal disclaimer.

(21) Appl. No.: 10/548,507

(22) PCT Filed: Mar. 4, 2004

(86) PCT No.: PCT/US2004/006661
§ 371 (c)(1),
(2), (4) Date: Jun. 13, 2006

(87) PCT Pub. No.: WO2004/080490
PCT Pub. Date: Sep. 23, 2004

(65) Prior Publication Data
US 2007/0087014 A1 Apr. 19, 2007

Related U.S. Application Data

(60) Provisional application No. 60/452,728, filed on Mar. 7, 2003.

(51) Int. Cl.
*C07K 14/31* (2006.01)
*A61K 39/085* (2006.01)
*A61K 39/09* (2006.01)
*A61K 47/48* (2006.01)
*A61K 39/00* (2006.01)

(52) U.S. Cl.
CPC .............. *C07K 14/31* (2013.01); *A61K 39/085* (2013.01); *A61K 39/092* (2013.01); *A61K 47/4823* (2013.01); *A61K 47/4833* (2013.01); *A61K 2039/6068* (2013.01)

(58) Field of Classification Search
None
See application file for complete search history.

(56) References Cited

U.S. PATENT DOCUMENTS

| 5,175,096 | A | 12/1992 | Hook et al. |
|---|---|---|---|
| 5,189,015 | A | 2/1993 | Hook et al. |
| 5,320,951 | A | 6/1994 | Hook et al. |
| 5,416,021 | A | 5/1995 | Hook et al. |
| 5,440,014 | A | 8/1995 | Hook et al. |
| 5,571,514 | A | 11/1996 | Hook et al. |
| 5,648,240 | A | 7/1997 | Hook et al. |
| 5,652,217 | A | 7/1997 | Hook et al. |
| 5,730,978 | A | 3/1998 | Wayner |
| 5,851,794 | A | 12/1998 | Guss et al. |
| 5,980,908 | A | 11/1999 | Hook et al. |
| 6,008,341 | A | 12/1999 | Foster et al. |
| 6,288,214 | B1 | 9/2001 | Hook et al. |
| 6,596,861 | B1* | 7/2003 | Moreau ...................... 536/123.1 |
| 6,635,473 | B1 | 10/2003 | Foster et al. |
| 6,703,025 | B1* | 3/2004 | Patti et al. .................. 424/243.1 |
| 6,841,154 | B2 | 1/2005 | Foster et al. |
| 6,994,855 | B1 | 2/2006 | Foster et al. |
| 7,252,828 | B2 | 8/2007 | Pier et al. |
| 7,666,438 | B1 | 2/2010 | Patti et al. |
| 2002/0119166 | A1* | 8/2002 | Pier et al. ................... 424/234.1 |
| 2002/0173462 | A1* | 11/2002 | Boden Wastfelt et al. ...... 514/12 |
| 2003/0068336 | A1 | 4/2003 | Ryall |
| 2007/0087014 | A1 | 4/2007 | Pavliak et al. |
| 2007/0141077 | A1 | 6/2007 | Pavliak et al. |
| 2010/0150956 | A1 | 6/2010 | Patti et al. |

FOREIGN PATENT DOCUMENTS

| AU | 2004220590 | 2/2010 |
|---|---|---|
| AU | 2004266111 | 12/2010 |
| CA | 2 351 018 | 1/2003 |
| EP | 1 034 792 | 9/2000 |
| IN | 226421 | 12/2008 |
| JP | 09-502978 | 3/1997 |
| JP | 2002-5234723 | 7/2002 |
| MX | 283832 | 6/2011 |
| NZ | 561879 | 3/2004 |
| NZ | 561879 | 9/2009 |
| WO | WO 85/05553 | 12/1985 |

(Continued)

OTHER PUBLICATIONS

Ansell et al 1996 Bioconjugate Chem vol. 7 pp. 490-496.*
Ansell et al (1996 Bioconjugate Chem vol. 7 pp. 490-496).*
Maxe et al 1986 Infection and Immunity vol. 54 No. 3 pp. 695-704.*
Cheng et al 2001 Infection and Immunity vol. 69 No. 4 pp. 2302-2308.*
Cheng et al 2002 Infection and Immunity vol. 69 No. 4 pp. 2408-2413.*
Casolini, et al. (Nov. 1998) "Antibody Response to fibronectin-binding adhesion FnbpA in Patients with Staphylococcus aureus infections." Infection and Immunity 66(11): 5433-5442.
Chinese Pharmacological Bulletin (2002) 18(3): 249-252.

(Continued)

*Primary Examiner* — Oluwatosin Ogunbiyi
(74) *Attorney, Agent, or Firm* — B. Aaron Schulman, Esq.; Stites & Harbison, PLLC.

(57) ABSTRACT

Immunogenic polysaccharide-protein conjugates having a polysaccharide antigen (or its oligosaccharide fragment representing one or more antigenic epitopes) derived from a nosocomial pathogen conjugated to a staphylococcal surface adhesin carrier protein are used in immunogenic compositions to elicit antibody responses to both the polysaccharide antigen and the staphylococcal surface adhesion carrier protein. Such immunogenic compositions are used to immunize against diseases caused by *Staphylococcal aureus*, *Staphylococcal epidermidis* or other nosocomial pathogens.

22 Claims, 34 Drawing Sheets

(56) References Cited

FOREIGN PATENT DOCUMENTS

| WO | WO 86/06635 | 11/1986 |
| WO | WO 94/10317 | 5/1994 |
| WO | WO 95/08348 | 3/1995 |
| WO | WO 97/43314 | 11/1997 |
| WO | WO 97/48727 | 12/1997 |
| WO | WO 99/03871 | 1/1999 |
| WO | WO/00/12131 | * 3/2000 |
| WO | WO 00/12131 | 3/2000 |
| WO | WO 00/12134 | 3/2000 |
| WO | WO 00/56359 | 9/2000 |
| WO | WO 00/71585 | 11/2000 |
| WO | WO 01/70685 | 9/2001 |
| WO | WO 01/72337 | 10/2001 |
| WO | WO 03/061558 | 7/2003 |
| WO | WO 03/076470 | 9/2003 |
| WO | WO 2004/080490 | 9/2004 |

OTHER PUBLICATIONS

Devi, et al. (Aug. 15, 1991) "Antibodies to poly[(2→8)-α-N-acetylneuraminic acid] and poly[(2→9)-α-N-acetylneuraminic acid] are elicited by immunization of mice with *Escherichia coli* K92 conjugates: potential vaccines for groups B and C meningococci and *E. coli* K1." Proc. Natl. Acad. Sci. USA 88: 7175-7179.

Fattom, et al. (Mar. 1993) "Laboratory and clinical evaluation of conjugate vaccines composed of *Staphylococcus aureus* type 5 and type 8 capsular polysaccharides bound to *Pseudomonas aeruginosa* recombinant exoprotein A." Infection and Immunity 61(3): 1023-1032.

Fattom, et al. (Oct. 1, 1995) "Effect of conjugation methodology, carrier protein, and adjuvants on the immune response to *Staphylococcus aureus* capsular polysaccharides." Vaccine 14(14): 1288-1293.

Fattom, et al. (1996) "A *Staphylococcus aureus* capsular polysaccharide (CP) vaccine and CP-specific antibodies protect mice against bacterial challenge." Infection and Immunity 64(5): 1659-1665.

Han, et al. (Jan. 1998) "Determination of alpha-toxin antibodies against *Staphylococcus aureus* and phagocytic ability postimmunization in rabbits." Bovine Practitioner 32(1): 14-17.

Josefsson, et al. (Sep. 2000) "Protection Against *Staphylococcus aureus* Arthritis by Vaccination with Clumping Factor A, a Novel Virulence Determinant." Immunology Letters 73(2/3): 153-154.

Josefsson, et al. (Dec. 15, 2001) "Protection Against *Staphylococcus aureus* Arthritis by Vaccination with Clumping Factor A, a Novel Virulence Determinant." Journal of Infectious Diseases 184(12): 1572-1580.

Konadu, et al. (Nov. 1994) "Preparation, Characterization, and Immunological Properties in Mice of *Escherichia coli* O157 O-Specific polysaccharide-protein conjugate vaccines." Infection and Immunity 62(11): 5048-5054.

Mamo, et al. (Nov. 1, 1994) "Vaccination with *Staphylococcus aureus* Fibrinogen Binding Proteins (FGBPS) Reduces Colonisation of *S. aureus* in a Mouse Mastitis Model." FEMS Immunology and Medical Microbiology 10(1): 47-53.

Park, et al. (Sep. 1999) "Immunogenicity of alpha-toxin, capsular polysaccharide (CPS) and recombinant fibronectin-binding protein (r-FnBP) of *Staphylococcus aureus* in rabbit." Journal of Veterinary Medical Science 61(9): 995-1000.

Schneerson, et al. (1991) "Evaluation of monophosphoryl lipid A (MPL) as an adjuvant: Enhancement of the serum antibody response in mice to polysaccharide-protein conjugates by concurrent injection with MPL." Journal of Immunology 147(7): 2136-214.

Shinefield, et al. (Feb. 14, 2002) "Use of a *Staphylococcus aureus* conjugate vaccine in patients receiving hemodialysis." New England Journal of Medicine 346(7): 491-496.

Tollersrud, et al. (2001) "*Staphylococcus aureus* capsular polysaccharide type 5 conjugate and while cell vaccines stimulate antibody responses in cattle." Vaccine 19:3896-3903.

Welch, et al. (1996) "Safety and Immunogenicity of *Staphylococcus aureus* type 5 capsular polysaccharide-pseudomonas conjugate vaccine in patients on hemodialysis." Journal of the American Society of Nephrology 7: 247-253.

International Search Report (Sep. 9, 2004).
Written Opinion of the International Searching Authority (Sep. 7, 2005).
International Preliminary Report on Patentability (Sep. 9, 2005).
Bash, et al. (1995) *Infection and Immunity* 63(4): 1484-1490.
Dinges, et al. (2000) *Clinical Microbiology Reviews* 13(1): 16-34.
Janson, et al. (Jan. 1991) *Infection and Immunity* 59(1): 119-125.
Brouillette, et al. (2002) *Vaccine* 20:2348-2357 [Abstract].
Smeltzer, et al. (1997) *Gene* 196(1-2): 249-259.
Brouillette, et al. (2002) *Vaccine* 20(17-18): 2348-57.
Josefsson, et al. (2001) *The Journal of Infectious Diseases* 184: 1572-80.
Aoki, et al. (2006) *Biosci. Biotechnol. Biochem.* 70(10): 2349-2356.
*Bacterial Pathogenesis*, Salyers and Whitt (1994) Chapter 21, pp. 260-269.
Collier (1975) "Diphtheria Toxin: Mode of Action and Structure." *Bacteriological Reviews* 39(1): 54-85.
Fattom, et al. (1990) *Infection and Immunity* 58(7): 2367-2374.
Fattom, et al. (1999) *Vaccine* 17(2): 126-33.
Hunt, et al. (1996) Immunol. Cell Biol. 74: 81-89.
Kao, et al. (2007) *J. Mol. Biol.* 374: 426-442.
Lukac, et al. (1998) "Toxoid of *Pseudomonas aeruginosa* Exotoxin A Generated by Deletion of an Active-Site Residue." *Infection and Immunity* 56(12): 3095-3098.
O'Riordan and Lee (2004) "*Staphylococcus aureus* Capsular Polysaccharides." *Clinical Microbiology Reviews* 17(1): 218-234.
Reeves, et al. (1996) *Trends in Microbiology* 4(12): 495-503.
Sau, et al. (1997) *Microbiology* 143: 2395-2405.
Rudinger, et al. Peptide Hormones, edited by Parsons, J.A., University Park Press, Jun. 1976, p. 6.
Tollersrud, et al. (2001) *Vaccine* 19: 3896-3903.
Verheul, et al. (1991) *Infection and Immunity* 59(3): 843-851.
*Polysaccharides: structural diversity and functional versatility* Severian Dumitriu (Ed.) (2005), pp. 1-1189, p. v "Preface".
Office Action dated Jun. 25, 2013 in corresponding Japanese Application No. 201-228995.
Foster et at Surface-associated proteins of *Staphylococcus aureus*: their possible roles in virulence. FEMS Microbiol Lett. May 15, 1994;118(3):199-205. Review.
Mamo et al. Vaccination with *Staphylococcus aureus* fibrinogen binding proteins (FgBPs) reduces colonisation of *S. aureus* in a mouse mastitis model. FEMS Immunol Med Microbiol. Nov. 1994;10(1):47-53.
Patti et al. Identification and biochemical characterization of the ligand binding domain of the collagen adhesin from *Staphylococcus aureus*. Biochemistry. Oct. 26, 1993;32(42):11428-35.
Dominiecki et al. Antibacterial action of extracellular mammalian group IIA phospholipase A2 against grossly clumped *Staphylococcus aureus*. Infect Immun. May 1999;67(5):2299-305.
Hartford et al. Matrix-binding proteins of *Staphylococcus aureus*: functional analysis of mutant and hybrid molecules. Microbiology. Sep. 1999;145 ( Pt 9):2497-505.
Schennings et al. Immunization with fibronectin binding protein from *Staphylococcus aureus* protects against experimental endocarditis in rats. Microb Pathog. Sep. 1993;15(3):227-36.
Lee JC. The prospects for developing a vaccine against *Staphylococcus aureus*. Trends Microbiol. Apr. 1996;4(4):162-6.
Rozalska et al., "Role of Antibodies Against Fibronectin, . . . ", Zentrablatt Fuer Bakteriologie, vol. 281, No. 4, 1994, pp. 495-501.
Nillson et al., "Vaccination with a recombinant fragment of collagen adhesion provides protection against *Staphylococcus aureus*-mediated septic death", *Journal of Clinical Investigation*, vol. 101, No. 12, Jun. 15, 1998, pp. 2640-2649.
McCrea et al, "A family of putative adherence proteins related to the clumping factor of Staphilococcus aureus", *Abstracts of the General Meeting of the American Society for Microbiology*, vol. 98, May 17, 1998, p. 63.
Espersen et al., "Immunization of Mice with the Fibronectin-Binding Protein and Clumping Factor from *Staphylococcus-aureus* Antibody . . . ", *ACTA Pathologica Microbiologica Et Immunologica Scandinavica Section* C, vol. 93, No. 2, 1985; pp. 53-58.

* cited by examiner

Antisera (Center Well):

H α-Clf A rabbit

Antigens:

1-CP5-Clf41 (N2N3) (His+); 2-CP8-Clf41 (N2N3); 3- Clf41 (N2N3)

1a-d CP5-SdrG (N2N3)
2 a-d CP5-Clf40 (N1N2N3)
3 a-d CP8-SdrG (N2N3)
4 a-d CP8- Clf40 (N1N2N3)
5a-CP5; 5b-CP8; 5c-d SdrG (N2N3),
6a-b buffer; 6c-d Clf40 (N1N2N3)

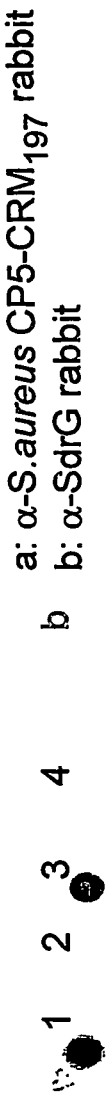
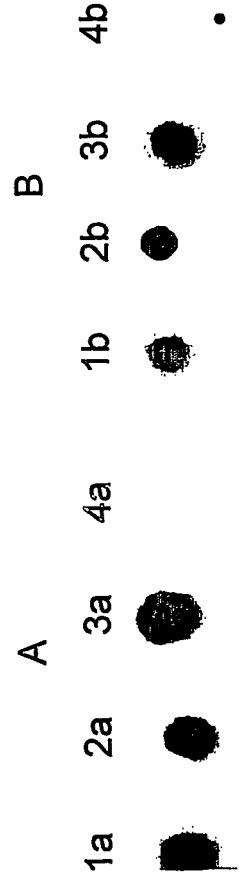
Antisera:
a: α-S.aureus CP5-CRM$_{197}$ rabbit
b: α-SdrG rabbit
Antigens:
1: CP5-Clf40 (N1N2N3)
2: CP5-BSA
3: Clf40 (N1N2N3)
4: CP5
Antiserum A: rabbit α-S.aureus CP5-CRM$_{197}$
Antigens: 1a: CP5-CRM$_{197}$; 2a: CP5-FnbA; 3a: CP5-SdrG (N2N3) (His-); 4a: CP5
Antiserum B: rabbit α-S.aureus CP8-CRM$_{197}$
Antigens: 1b: CP8-CRM$_{197}$; 2b: CP8-FnbA; 3b: CP8-SdrG (N2N3) (His-); 4b: CP8
FIG.14

POLYSACCHARIDE-STAPHYLOCOCCAL SURFACE ADHESIN CARRIER PROTEIN CONJUGATES FOR IMMUNIZATION AGAINST NOSOCOMIAL INFECTIONS

This application is the US national phase of international application PCT/US2004/006661 filed on Mar. 4, 2004, which designated the US and claims priority to U.S. Provisional Application No. 60/452,728, filed Mar. 7, 2003. The entire contents of these applications are incorporated herein by reference.

FIELD OF THE INVENTION

This invention relates to an immunogenic polysaccharide-protein conjugate comprising a polysaccharide antigen (or its oligosaccharide fragment representing one or more antigenic epitopes) from a nosocomial pathogen and a staphylococcal surface adhesin carrier protein. This invention also relates to immunogenic compositions comprising the polysaccharide-protein conjugate, and their use.

BACKGROUND OF THE INVENTION

Every year about 2 million of the estimated 40 million people admitted to hospitals in the U.S. will develop a nosocomial infection (Anonyomous 1997). With a morality rate of approximately 4.4%, nosocomial infections contribute to 88,000 deaths per year. The cost of hospital-acquired infections in the U.S. has been estimated at $4.5 billion per year (Weinstein 1998). These estimates do not include infections occurring in the 31 million outpatient surgeries performed each year (National Center for Health Statistics' website), the 1.5 million nursing home residents, the extended care facilities, or among those receiving ambulatory care procedures.

*Staphylococcus aureus* and coagulase-negative staphylococci (CoNS), particularly *S. epidermidis*, are Gram-positive opportunistic nosocomial pathogens that are responsible for the majority of nosocomial infections. Staphylococcal infections account for nearly 25% (approximately 500,000) of all nosocomial infections (Haley, Culver et al. 1985) (Boyce 1997). Up to 1% of all admissions in some hospitals result in *S. aureus* infections (Storch and Rajagopalan 1986). Staphylococci (*S. aureus* and *S. epidermidis*) account for about 47% of the nosocomial bloodstream infections, 24% of the surgical site infections (SSI), and 17% of hospital-acquired pneumonia (Anonyomous 1997). The mortality rate of patients with nosocomial *S. aureus* and CoNS infections varies considerably, ranging from 5% to 68% (Nada, Ichiyama et al. 1996); (Thylefors, Harbarth et al. 1998).

Staphylococcal infections are diverse in scope, ranging from cutaneous infections, such as impetigo, boils, wound infections and infections from implanted devices, to severe life-threatening infections, such as osteomyelitis, endocarditis and bacteremia with metastatic complications. This diversity makes the design of an efficacious immunogenic composition against staphylococci a true challenge. A sharp increase in the appearance of drug-resistant nosocomial bacteria makes such a design even more difficult. Methicillin-resistant *S. aureus* causes approximately 40% of the deaths attributed to nosocomial infections (Boyce 1997). The recent emergence of vancomycin intermediate-resistant *S. aureus* (VISA) has raised even greater concern over its spread. Thus, there is a strong and rapidly growing need for an efficacious immunogenic composition against nosocomial infections.

Capsular Polysaccharides

The involvement of capsular polysaccharides (CP) in the virulence of many bacterial pathogens, including *Haemophilus influenzae, Streptococcus pneumoniae* and group B streptococci, is well established. Encapsulated bacteria are resistant to phagocytosis by leukocytes, and thus can infect the blood and tissues. Because antibodies to capsular polysaccharides neutralize the anti-phagocytic properties of the bacterial capsule (Karakawa, Sutton et al. 1988; Thakker, Park et al. 1998), the staphylococcal capsule has been a major target in the development of immunogenic compositions to prevent staphylococcal infection in humans.

Of the 12 known capsular serotypes of *S. aureus*, serotype 5 (CP5) and serotype 8 (CP8) account for approximately 85-90% of all clinical isolates (Arbeit, Karakawa et al. 1984; Karakawa, Fournier et al. 1985; Essawi, Na'was et al. 1998; Na'was, Hawwari et al. 1998). Most methicillin-resistant *S. aureus* isolates express CP5 (Sompolinsky, Samra et al. 1985). Antibodies to CP5 and CP8 induce type-specific opsonophagocytic killing by human polymorphonuclear neutrophils in vitro and confer protection in animals (Karakawa, Sutton et al. 1988; Fattom, Sarwar et al. 1996).

Most bacterial capsular polysaccharides are poor immunogens in animals and humans. However, if the purified polysaccharides are conjugated to protein carrier molecules, they acquire immunogenicity and T-ell dependency. Several laboratories have synthesized immunogenic conjugates consisting of CP5 and CP8 covalently linked to protein. These conjugates are highly immunogenic in mice and humans and induce antibodies that opsonize microencapsulated *S. aureus* for phagocytosis (Fattom, Schneerson et al. 1993; Gilbert et al. 1994; Reynaud-Rondier et al. 1991). Monovalent immunogenic compositions containing CP5 conjugated to *Pseudomonas aeruginosa* recombinant exotoxin A are immunogenic and well tolerated in healthy adults and in patients with end-stage renal disease (Welch et al. 1996). In a double-blind trial involving patients with end-stage renal disease who were receiving hemodialysis, a bivalent conjugate vaccine composed of CP5 and CP8 covalently bound to *Pseudomonas aeruginosa* recombinant exotoxin A conferred partial immunity against *S. aureus* bacteremia for approximately 40 weeks, after which protection decreased as antibody levels decreased (Shinefield et al. 2002). The outcome of this trial indicates a need for an improved immunogenic composition that could contribute to more complete protection.

Another type of extracellular polysaccharide, referred to as polysaccharide adhesin (PS/A; (Tojo, Yamashita et al. 1988)), poly-N-succinyl β1-6 glucosamine (PNSG; (McKenney, Pouliot et al. 1999)), poly-N-acetylglucosamine surface polysaccharide (PNAG; (Maira-Litran, Kropec et al. 2002)), or polysaccharide Intercellular adhesin (PIA (Mack, Fischer et al. 1996)) is expressed by both *S. aureus* and *S. epidermidis*. PIA or PS/A is a linear β1,6-linked glucosaminoglycan. Immunization of mice with PS/A (PNSG, PNAG) reduces colonization of kidneys and protects mice from death after challenge with *S. aureus* strains that produced little PS/A (PNSG, PNAG) in vitro (McKenney, Pouliot et al. 1999). PIA plays an important role in the pathogenesis of intravascular catheter-associated infections (Rupp, Ulphani et al. 1999; Rupp, Ulphani et al. 1999; Rupp and Fey 2001; Rupp, Fey et al. 2001). In addition to promoting adhesion between individual *S. epidermidis* cells, PIA binds to erythrocytes and acts as a hemagglutinin (Fey, Ulphani et al. 1999).

Staphylococcal Surface Adhesins

Staphylococci express multiple surface adhesins (termed microbial surface components recognizing adhesive matrix molecules) which include, for example, fibronectin-binding protein, fibrinogen-binding protein, collagen-binding protein and vitronectin-binding protein. These adhesins specifically recognize and bind to extracellular matrix (ECM) components, such as, for example, fibronectin, fibrinogen, collagen and vitronectin. The redundancy and multitude of adhesion factors expressed by S. aureus contribute to its pathogenicity by providing alternate methods for adherence to, and infection of, a variety of tissues. Antibodies to staphylococcal adhesins may reduce disease by preventing bacteria from invading mammalian host tissues or by promoting opsonophagocytosis. Rats immunized with a portion of the S. aureus fibronectin-binding protein A (provided as a fusion protein) endowed the rats with a modest degree of protection from experimental endocarditis. A similar immunogenic composition designed to elicit antibodies to fibronectin-binding protein A was tested in a mouse model of S. aureus mastitis. Immunized mice showed fewer cases of severe mastitis than the control mice and fewer bacteria were recovered from the mammary glands of immunized mice than of control mice. Mice immunized with fibrinogen-binding proteins of 19 and 87 kDa showed a reduced incidence of mastitis compared with nonimmunized controls, whereas immunization with collagen-binding protein was not protective (Lee, Pier 1997).

However, despite these and other efforts to conjugate polysaccharide antigens to a variety of protein carriers, there currently is no efficacious immunogenic composition for treating or preventing nosocomial infections.

SUMMARY OF THE INVENTION

The present invention thus provides an immunogenic polysaccharide-protein conjugate that comprises at least one polysaccharide antigen derived from a nosocomial pathogen, or an oligosaccharide fragment representing one or more antigenic epitopes of at least one polysaccharide antigen (prepared synthetically or by hydrolysis of native polysaccharide) conjugated to at least one staphylococcal surface adhesin carrier protein. The conjugates of this invention are used in immunogenic compositions, which are useful in eliciting in a subject specific antibody responses to both the polysaccharide antigen of the nosocomial pathogen and the surface adhesin carrier protein. As such, these conjugates can be used to immunize against nosocomial infections caused by S. aureus, S. epidermidis or other nosocomial pathogens, and for the generation of immunoglobulin for passive immunization to prevent or reduce the severity of nosocomial infections.

In one aspect of the invention, there is provided an immunogenic polysaccharide-protein conjugate comprising at least one polysaccharide antigen from a nosocomial pathogen conjugated to at least one staphylococcal surface adhesin carrier protein, wherein the conjugate generates specific antibodies to both the polysaccharide antigen and the surface adhesin carrier protein.

In another aspect of the invention, there is provided an immunogenic polysaccharide-protein conjugate comprising an oligosaccharide fragment representing one or more antigenic epitopes of at least one polysaccharide antigen from a nosocomial pathogen conjugated to at least one staphylococcal surface adhesin carrier protein, wherein the conjugate generates specific antibodies to both the polysaccharide antigen and the surface adhesin carrier protein.

In yet another aspect, there is provided an immunogenic composition which comprises the polysaccharide antigen-surface adhesin protein conjugate in association with a suitable carrier or diluent. The immunogenic compositions of the invention may also comprise an adjuvant, such as, for example, aluminum hydroxide or aluminum phosphate.

In yet a further aspect, there is provided a method of inducing active immunity against nosocomial infections in a mammal, which method comprises administering to the mammal subject to such infections, including a human, an immunogenic amount of an immunogenic composition of the invention.

In still another aspect, there is provided a method of preparing an immunotherapeutic agent against nosocomial infections, which method comprises the steps of immunizing a mammal with the immunogenic composition of the invention, collecting plasma from the immunized mammal, and harvesting from the collected plasma a hyperimmune globulin that contains anti-polysaccharide antibodies and anti-surface adhesin antibodies. The hyperimmune globulin can be used for inducing passive immunity to nosocomial infections.

The conjugates of the present invention have the distinct advantage of eliciting antibodies to both the polysaccharide antigen and the surface adhesin carrier protein (both of which are virulence factors), and conferring immunity to the diseases caused by nosocomial pathogens. That is, the surface adhesin protein itself can confer immunity and not merely act as a protein carrier for the polysaccharide antigen.

BRIEF DESCRIPTION OF THE DRAWINGS

FIG. 14 shows the analysis of conjugates by dot blot.

DETAILED DESCRIPTION OF THE INVENTION

Figure 1:
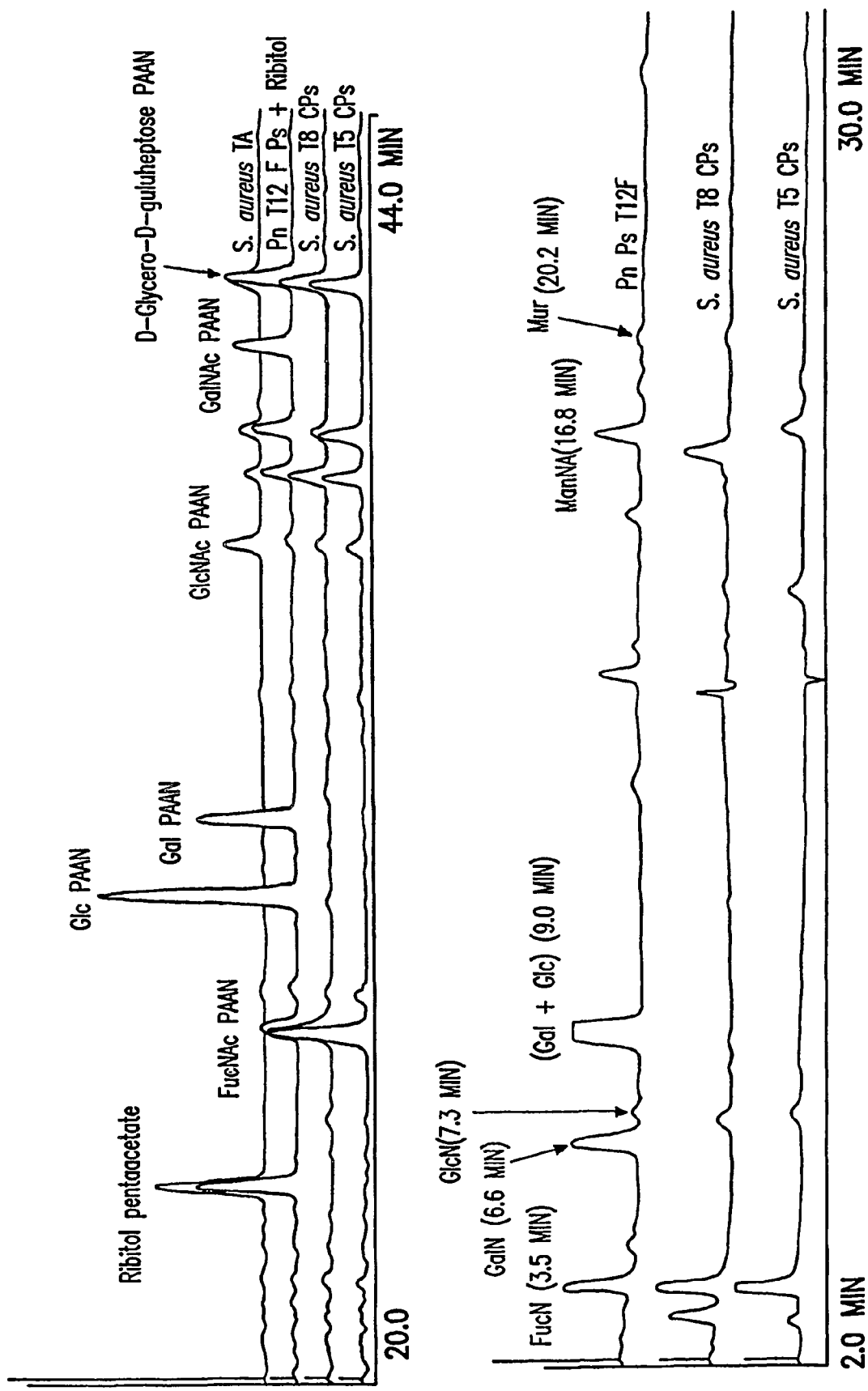
FIG. 1 shows a composition of S. aureus CP5 and CP8 as determined by GLC and HPAEC-PAD analysis.

Nosocomial infections involve multiple virulence factors. Thus, it is highly probable that a combination of virulence determinants included as components in immunogenic compositions would increase protection compared with an immunogenic composition containing only a single virulence determinant. The polysaccharide antigens of the present invention are derived from various nosocomial pathogenic microorganisms including, but not limited to, *Staphylococcus aureus, Staphylococcus epidermidis* and other coagulase-negative staphylococci (CoNS), *Enterococcus* spp., *Candida albicans, Enterobacter* spp., *Haemophilus influenzae, Klebsiella pneumoniae, Escherichia coli,* and *Pseudomonas aeruginosa*. These antigens are virulence factors in systemic infections and are poor immunogens. Their immunogenicity can be enhanced by conjugation to a carrier protein. For the purpose of the present invention surface adhesin proteins are microbial surface components recognizing adhesive matrix molecules. These are suitably available under the trademark MSCRAMM® from Inhibitex Inc, Alpharetta, Ga., USA. As described below, utilizing a *staphylococcus* surface adhesin protein as a carrier protein for polysaccharide antigens converts the polysaccharide into a T-cell dependent antigen, thus inducing an anti-polysaccharide IgG response. Furthermore, the conjugate induces anti-surface adhesin carrier protein antibodies that protect against infection and help prevent bacterial adherence to mammalian host tissues. Although it has been known that the chemical reactions of the protein-saccharide conjugation methods may have a deleterious effect on the immunogenic epitopes of carrier proteins, surprisingly in the present invention, no such effect is seen, and the protein remains capable of eliciting responses against protective epitopes.

Surface adhesin proteins on the bacterial cell surface and ligands within the host tissue interact in a lock and key fashion resulting in the adherence of bacteria to the host. Adhesion is often required for bacterial survival and helps bacteria evade host defense mechanisms and antibiotic challenges. Once the bacteria have successfully adhered to and colonized host tissues, their physiology is dramatically altered, and damaging components such as toxins and enzymes are secreted. Moreover, the adherent bacteria often produce a biofilm and quickly become resistant to the killing effect of most antibiotics.

Representative examples of surface adhesin proteins include fibronectin-binding protein, fibrinogen-binding protein, collagen-binding protein and vitronectin-binding protein. These adhesins specifically recognize and bind to the extracellular matrix components fibrinogen, fibronectin, collagen and vitronectin.

Fibronectin-Binding Protein

Fibronectin (Fn) is a 440-kDa glycoprotein found in the ECM and body fluids of animals. The primary biological function of fibronectin appears to be related to its ability to serve as a substrate for the adhesion of cells expressing the appropriate integrins. Several bacterial species have been shown to bind fibronectin specifically and to adhere to a fibronectin-containing substratum. Most *S. aureus* isolates bind Fn, but do so in varying extents, which reflects variations in the number of surface adhesin molecules expressed on the bacterial cell surface. The interaction between Fn and *S. aureus* is highly specific (Kuusela 1978). Fn binding is mediated by two surface exposed proteins with molecular weights of 110 kDa, named FnBP-A and FnBP-B. The primary Fn binding site consists of a motif of 35-40 amino acids, repeated three to five times. The genes for these have been cloned and sequenced (Jonsson 1991).

WO-A-85/05553 discloses bacterial cell surface proteins having fibronectin-, fibrinogen-, collagen-, and/or laminin-binding ability.

U.S. Pat. Nos. 5,320,951 and 5,571,514 to Hook, et al., disclose the fibronectin-binding protein A (fnbA) gene sequence, and products and methods based on this sequence.

U.S. Pat. No. 5,175,096 to Hook et al., discloses the gene sequence of fnbB, a hybrid DNA molecule (fnbB) and biological products and methods based on this sequence.

U.S. Pat. No. 5,652,217 discloses an isolated and purified protein having binding activity that is encoded by a hybrid DNA molecule from *S. aureus* of defined sequence.

U.S. Pat. No. 5,440,014 discloses a fibronectin-binding peptide within the D3 homology unit of a fibronectin-binding protein of *S. aureus* which can be used for immunization of ruminants against mastitis caused by staphylococcal infections, for treatment of wounds, for blocking protein receptors, for immunization of other animals, or for use in a diagnostic assay.

U.S. Pat. No. 5,189,015 discloses a method for the prophylactic treatment of the colonization of a *S. aureus* bacterial strain having the ability to bind to fibronectin in a mammal that includes administering to the mammal in need of treatment a prophylactically effective amount of a protein having fibronectin-binding properties, to prevent the generation of infections caused by a *S. aureus* bacterial strain having the ability to bind fibronectin, wherein the protein has a molecular weight of 87 kDa to 165 kDa.

U.S. Pat. No. 5,416,021 discloses a fibronectin-binding protein encoding DNA from *Streptococcus dysgalactiae*, along with a plasmid that includes DNA encoding for fibronectin-binding protein from *S. dysgalactiae* contained in *E. coli*, DNA encoding a fibronectin-binding protein from *S. dysgalactiae* and an *E. coli* microorganism transformed by DNA encoding a fibronectin-binding protein from *S. dysgalactiae*.

Collagen-Binding Protein

Collagen is the major constituent of cartilage. Collagen (Cn) binding proteins are commonly expressed by staphylococcal strains. The collagen-binding surface adhesin protein of *S. aureus* adheres to cartilage in a process that constitutes an important part of the pathogenic mechanism in staphylococcal infections (Switalski 1993). Collagen binding by *S. aureus* is found to play a role in at least, but not only, arthritis and septicemia. Collagen adhesins (CNAs) with molecular weights of 133, 110 and 87 kDa (Patti, J., et al. 1992) have been identified. Strains expressing CNAs with different molecular weights do not differ in their collagen-binding ability (Switalski 1993).

Staphylococcal strains recovered from the joints of patients diagnosed with septic arthritis or osteomyelitis almost invariably express a collagen-binding protein, whereas significantly fewer isolates obtained from wound infections express this adhesin (Switalski et al. 1993). Similarly, *S. aureus* strains isolated from the bones of patients with osteomyelitis often have a surface adhesin protein recognizing the bone-specific protein, bone sialoprotein (BSP) (Ryden et al. 1987). S. aureus colonization of the articular cartilage within the joint space appears to be an important factor contributing to the development of septic arthritis.

WO 92/07002 discloses a hybrid DNA molecule which includes a nucleotide sequence from S. aureus coding for a protein or polypeptide having collagen-binding activity and a plasmid or phage comprising the nucleotide sequence.

Also disclosed are an E. coli strain expressing the collagen-binding protein, a microorganism transformed by the recombinant DNA, the method for producing a collagen-binding protein or polypeptide, and the protein sequence of the collagen-binding protein or polypeptide.

The cloning, sequencing, and expression of a gene cna, encoding a S. aureus collagen-binding protein has been reported (Patti, J., et al. 1992).

The cna gene encodes a 133-kDa adhesin that contains structural features characteristic of surface proteins isolated from Gram-positive bacteria.

Recently, the ligand-binding site has been localized within the N-terminal half of the collagen-binding protein (Patti, J. et al. 1993). By analyzing the collagen binding activity of recombinant proteins corresponding to different segments of the surface adhesin protein, a 168-amino-acid long protein fragment (corresponding to amino acid residues 151-318) that had appreciable collagen binding activity was identified. Short truncations of this protein in the N or C terminus resulted in a loss of ligand binding activity but also resulted in conformational changes in the protein as indicated by circular dichroism spectroscopy.

Patti et al. (1995) disclose a collagen-binding epitope in the S. aureus adhesin encoded by the cna gene. In their study, the authors synthesized peptides derived from the sequence of the said protein and used them to produce antibodies. Some of these antibodies inhibit the binding of the protein to collagen.

WO 97/43314 discloses that certain identified epitopes of the collagen-binding protein (M55, M33, and M17) can be used to generate protective antibodies.

The application also discloses the crystal structure of the collagen-binding protein which provides critical information necessary for identifying compositions which interfere with, or block completely, the binding of collagen to S. aureus collagen-binding protein. The ligand-binding site in the S. aureus collagen-binding protein and a 25-amino-acid peptide was characterized that directly inhibits the binding of S. aureus to 125 I-labeled type II collagen.

Fibrinogen-Binding Protein

Fibrin is the major component of blood clots, and fibrinogen/fibrin is one of the major plasma proteins deposited on implanted biomaterials. Considerable evidence exists to suggest that bacterial adherence to fibrinogen/fibrin is important in the initiation of device-related infection. For example, as shown by Vaudaux et al. (1989), S. aureus adheres to in vitro plastic that has been coated with fibrinogen in a dose-dependent manner. In addition, in a model that mimics a blood clot or damage to a heart valve, Herrmann et al. (1993) demonstrated that S. aureus binds avidly via a fibrinogen bridge to platelets adhering to surfaces. S. aureus can adhere directly to fibrinogen in blood clots formed in vitro, and can adhere to cultured endothelial cells via fibrinogen deposited from plasma acting as a bridge (Moreillon et al. 1995; Cheung et al. 1991). As shown by Vaudaux et al. and Moreillon et al., mutants defective in the fibrinogen-binding protein clumping factor (ClfA) exhibit reduced adherence to fibrinogen in vitro, to explanted catheters, to blood clots, and to damaged heart valves in the rat model for endocarditis (Vaudaux et al. 1995; Moreillon et al. 1995).

An adhesin for fibrinogen, often referred to as "clumping factor," is located on the surface of S. aureus cells. The interaction between bacteria and fibrinogen in solution results in the instantaneous clumping of bacterial cells. The binding site on fibrinogen is located in the C-terminus of the gamma chain of the dimeric fibrinogen glycoprotein. The affinity is very high and clumping occurs in low concentrations of fibrinogen. Scientists have recently shown that clumping factor also promotes adherence to solid phase fibrinogen, to blood clots, and to damaged heart valves (McDevitt et al. 1994; Vaudaux et al. 1995; Moreillon et al. 1995).

Two genes in S. aureus have been found that code for two fibrinogen-binding proteins, ClfA and ClfB. The gene, clfA, was cloned and sequenced and found to code for a polypeptide of 92 kDa. ClfA binds the gamma chain of fibrinogen, and ClfB binds the alpha and beta chains (Eidhin, et al. 1998). ClfB is a cell-wall associated protein with a predicted molecular weight of 88 kDa and an apparent molecular weight of 124 kDa that binds both soluble and immobilized fibrinogen and acts as a clumping factor.

The gene for a clumping factor protein, designated ClfA, was cloned, sequenced and analyzed in detail at the molecular level (McDevitt et al. 1994; McDevitt et al. 1995). The predicted protein is composed of 933 amino acids. A signal sequence of 39 residues occurs at the N-terminus followed by a 520 residue region (region A), which contains the fibrinogen-binding domain. A 308 residue region (region R), composed of 154 repeats of the dipeptide serine-aspartate, follows. The R region sequence is encoded by the 18 base pair repeat GAY TCN GAY TCN GAY AGY (SEQ ID NO. 1) in which Y equals pyrimidines and N equals any base. The C-terminus of ClfA has features present in many surface proteins of gram-positive bacteria such as an LPDTG (SEQ ID NO. 2) motif, which is responsible for anchoring the protein to the cell wall, a membrane anchor, and positive charged residues at the extreme C-terminus.

The platelet integrin alpha IIbβ3 recognizes the C-terminus of the gamma chain of fibrinogen. This is a crucial event in the initiation of blood clotting during coagulation. ClfA and alpha IIbβ3 appear to recognize precisely the same sites on the fibrinogen gamma chain because ClfA can block platelet aggregation, and a peptide corresponding to the C-terminus of the gamma chain (198-411) can block both the integrin and ClfA interacting with fibrinogen (McDevitt et al. 1997). The fibrinogen-binding site of alpha IIbβ3 is close to, or overlaps, a Ca2+ binding determinant referred to as an "EF hand." ClfA region A carries several EF hand-like motifs. A concentration of Ca2+ in the range of 3-5 mM blocks these ClfA-fibrinogen interactions and changes the secondary structure of the ClfA protein. Mutations affecting the ClfA EF hand reduce or prevent interactions with fibrinogen. Ca2+ and the fibrinogen gamma chain seem to bind to the same, or to overlapping, sites in ClfA region A.

The alpha chain of the leukocyte integrin, alpha Mβ2, has an insertion of 200 amino acids (A or I domain) which is responsible for ligand binding activities. A novel metal ion-dependent adhesion site (MIDAS) motif in the I domain is required for ligand binding. Among the ligands recognized is fibrinogen. The binding site on fibrinogen is in the gamma chain (residues 190-202). It was recently reported that Candida albicans has a surface protein, alpha Intlp, having properties reminiscent of eukaryotic integrins. The surface protein has amino acid sequence homology with the I domain of Mβ2, including the MIDAS motif. Furthermore, Intlp binds to fibrinogen.

ClfA region A also exhibits some degree of sequence homology with alpha Intlp. Examination of the ClfA region A sequence has revealed a potential MIDAS motif. Mutations in putative cation coordinating residues in the D×S×S portion of the MIDAS motif in ClfA results in a significant reduction in fibrinogen binding. A peptide corresponding to the gamma-chain binding site for alpha Mβ2 (190-202) has been shown by O'Connell et al. to inhibit ClfA-fibrinogen interactions (O'Connell 1998). Thus it appears that ClfA can bind to the gamma chain of fibrinogen at two separate sites. The ligand binding sites on ClfA are similar to those employed by eukaryotic integrins and involve divalent cation binding EF-hand and MIDAS motifs.

Also known is the fibrinogen-binding protein, ClfB, which has a predicted molecular weight of approximately 88 kDa and an apparent molecular weight of approximately 124 kDa. ClfB is a cell-wall associated protein and binds both soluble and immobilized fibrinogen. In addition, ClfB binds both the alpha and beta chains of fibrinogen and acts as a clumping factor.

Proteins related to the fibrinogen-binding ClfA and ClfB have been found, which bind to the extracellular matrix. The SdrC, SdrD and SdrE proteins are related in primary sequence and structural organization to the ClfA and ClfB proteins, and are also localized on the cell surface. With the A region of these proteins localized on the cell surface, the proteins can interact with the proteins in plasma, the extracellular matrix or with molecules on the surface of host cells. SdrC can bind to the extracellular matrix proteins, such as, for example, vitronectin. SdrE also binds to the extracellular matrix; for example, SdrE binds bone sialoprotein (BSP).

It has been discovered that in the A region of SdrC, SdrD. SdrE. ClfA, and ClfB, there is highly conserved amino acid sequence that can be used to derive a consensus TYTFT-DYVD (SEQ ID NO. 3) motif. The motif can be used in multicomponent vaccines to impart broad spectrum immunity to bacterial infections, and also can be used to produce monoclonal or polyclonal antibodies that impart broad spectrum passive immunity. In an alternative embodiment, any combination of the variable sequence motif derived from the Sdr and Clf protein families, (T/I) (Y/F) (TN) (F) (T) (D/N) (Y) (V) (D/N), can be used to impart immunity or to induce protective antibodies.

MHC-II Analogous Proteins

In addition to fibrinogen, fibronectin and collagen, *S. aureus* strains associate with other adhesive eukaryotic proteins, many of which belong to the family of adhesive matrix proteins, such as vitronectin (Chatwal et al. 1987). U.S. Pat. No. 5,648,240 discloses a DNA segment comprising a gene encoding a *S. aureus* broad spectrum adhesin that has a molecular weight of about 70 kDa. The adhesin is capable of binding fibronectin or vitronectin and includes a MHC II mimicking unit of about 30 amino acids. Further analyses of the binding specificities of this protein reveal that it functionally resembles an MHC II antigen in that it binds synthetic peptides. Thus, in addition to mediating bacterial adhesion to extracellular matrix proteins, it may play a role in staphylococcal infections by suppressing the immune system of the host.

Sdr Proteins from *Staphylococcus epidermidis*

*Staphylococcus epidermidis*, a coagulase-negative bacterium, is a common inhabitant of human skin and a frequent cause of foreign-body infections. Pathogenesis is facilitated by the ability of the organism to first adhere to, and subsequently to form biofilms on, indwelling medical devices such as artificial valves, orthopedic devices, and intravenous and peritoneal dialysis catheters. Device-related infections may jeopardize the success of medical treatment and significantly increase patient mortality. Accordingly, the ability to develop vaccines that can control or prevent outbreaks of *S. epidermidis* infection is of great importance, as is the development of conjugate vaccines that can prevent or treat infection from a broad spectrum of bacteria, including both coagulase-positive and coagulase-negative bacteria at the same time.

Three Sdr (serine-aspartate (SD) repeat region) proteins that are expressed by *S. epidermidis* have been designated as SdrF, SdrG and SdrH, and the amino acid sequences of these proteins and their nucleic acid sequences are shown WO 00/12131, which is incorporated herein by reference.

In accordance with the present invention, a conjugate useful as an immunogenic composition is provided that includes at least one polysaccharide antigen conjugated to at least one of the surface adhesin proteins described above. In addition, antibodies to the polysaccharide antigen and the surface adhesin protein are raised using conventional means. As such, the immunogenic compositions that include a surface adhesin protein, such as SdrG, are used to treat a broad spectrum of bacterial infections, including those arising from both coagulase-positive and coagulase-negative bacteria.

The other component of the conjugates of this invention comprises at least one polysaccharide antigen derived from a nosocomial pathogen. Such nosocomial pathogens include, but are not limited to, *Staphylococcus aureus, Staphylococcus epidermidis* and other coagulase-negative staphylococci (CoNS), *Enterococcus* spp., *Candida albicans, Enterobacter* spp., *Haemophilus influenzae, Klebsiella pneumoniae, Escherichia coli*, and *Pseudomonas aeruginosa*.

In one embodiment of this invention, the polysaccharide antigen comprises at least one of *S. aureus* CP5 and CP8.

In another embodiment of this invention, the polysaccharide antigen comprises at least one of PS/A, PNSG, PNAG and PIA, as expressed by *S. aureus* and/or *S. epidermidis*.

Preparation and Use of Immunogenic Compositions

Immunogenic compositions are prepared from the polysaccharide antigen-surface adhesin protein conjugates as disclosed herein. The immunogenic compositions elicit an immune response that produces antibodies to both the polysaccharide antigen and the surface adhesin carrier protein.

Immunogenic compositions are also prepared from the oligosaccharide antigen-surface adhesin protein conjugates as disclosed herein. The immunogenic compositions elicit an immune response that produces antibodies to both the oligosaccharide antigen and the surface adhesin carrier protein.

Conjugates provided herein that are suitable for use as immunogenic compositions include, but are not limited to:

(i) CP5 conjugated to a fibrinogen-binding protein or peptide of *S. aureus*, such as Clumping Factor A (ClfA), or a useful fragment thereof, or a protein or fragment with sufficiently high homology thereto; or (ii) CP8 conjugated to a fibrinogen-binding protein or peptide of *S. aureus*, such as Clumping Factor A (ClfA), or a useful fragment thereof, or a protein or fragment with sufficiently high homology thereto; or (iii) PIA conjugated to a fibrinogen-binding protein or peptide of *S. aureus*, such as Clumping Factor A (ClfA), or a useful fragment thereof, or a protein or fragment with sufficiently high homology thereto; or (iv) CP5 conjugated to a fibrinogen-binding protein or peptide of *S. epidermidis*, such as SdrG, or a useful fragment thereof, or a protein or fragment with sufficiently high homology thereto; or (v) CP8 conjugated to a fibrinogen-binding protein or peptide of *S. epidermidis*, such as SdrG, or a useful fragment thereof, or a protein or fragment with sufficiently high homology thereto; or (vi) PIA conjugated to a fibrinogen-binding protein or peptide of S. epidermidis, such as SdrG, or a useful fragment thereof, or a protein or fragment with sufficiently high homology thereto.

In each instance, an immunogenic composition created from any of conjugates (i) through (vi) is useful to immunize a patient against infection from coagulase-positive bacteria such as S. aureus, as well as coagulase-negative bacteria such as S. epidermidis.

In addition to conjugates (i) through (vi) described above, wherein the surface adhesin carrier protein is a fibrinogen-binding protein, the present invention also contemplates conjugates wherein the surface adhesin carrier protein is any staphylococcal surface adhesin protein, such as, for example, fibronectin-binding protein, collagen-binding protein and vitronectin-binding protein. The present invention also contemplates that the polysaccharide antigen can be PS/A, PNAG or PNSG, or other polysaccharide antigens from nosocomial pathogenic microorganisms, such as S. aureus, S. epidermidis and other CoNS, Enterococcus spp., Candida albicans, Enterobacter spp., Haemophilus influenzae, Klebsiella pneumoniae, Escherichia coli, and Pseudomonas aeruginosa.

Many methods are known in the art for conjugating a polysaccharide to a protein, and are suitable for use herein. In general, the polysaccharide should be activated or otherwise rendered amenable to conjugation, i.e., at least one moiety must be rendered capable of covalently bonding to a protein or other molecule. Many such methods are known in the art. For instance, U.S. Pat. No. 4,356,170, issued to Jennings, describes the use of periodic acid to generate aldehyde groups on the polysaccharide and then performs reductive amination using cyanoborohydride. U.S. Pat. No. 4,663,160, issued to Tsay et al., also used periodic acid to generate aldehyde groups but then linked the polysaccharide to a protein derivatized with a 4-12 carbon moiety (prepared in the presence of a condensing agent) with a Schiff's base reaction in the presence of a reducing agent such as cyanoborohydride. U.S. Pat. No. 4,619,828, issued to Gordon, used cyanogen bromide to activate the polysaccharide and then conjugated it through a spacer bridge of 4-8 carbon atoms to the protein. Still other methods of conjugation are known in the art.

Figure 7:
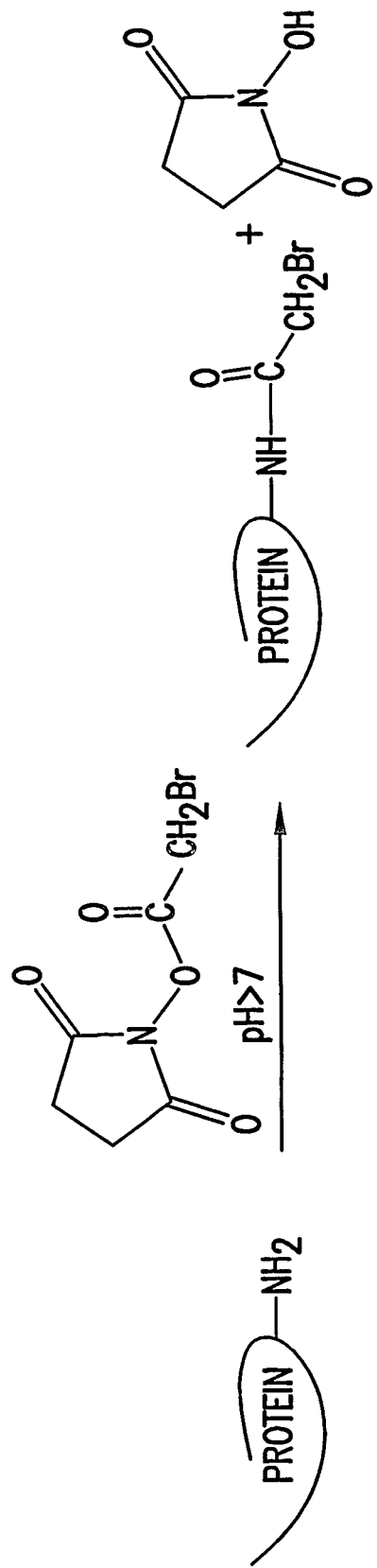
FIG. 7 shows bromoacetylation of a surface adhesin protein.
Figure 8:
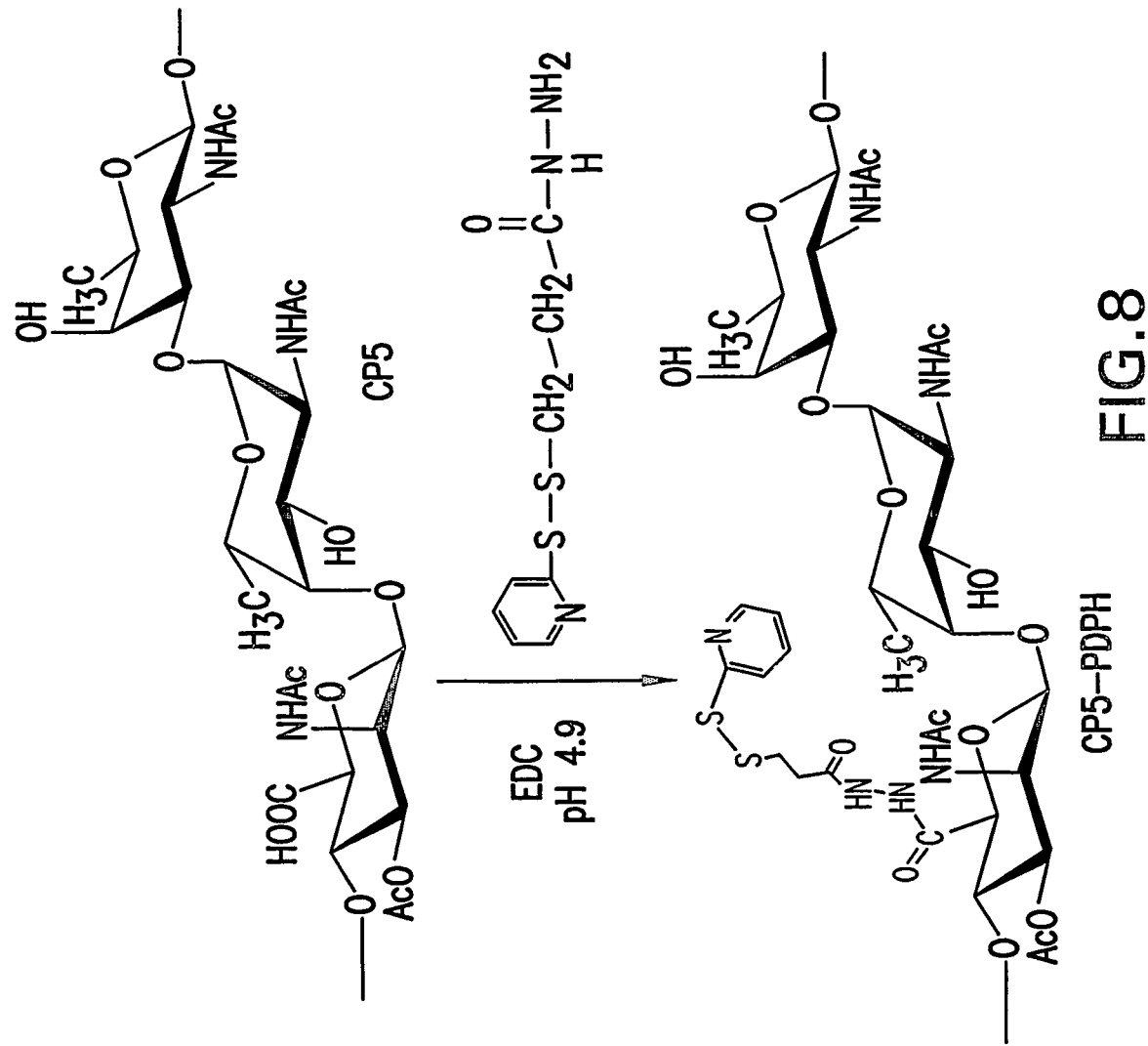
FIG. 8 shows activation of S. aureus CP with 3-(2-pyridyldithio)propionyl hydrazide (PDPH).

In one embodiment of the present invention, the CP is activated with the linker 3-(2-pyridyldithio)-propionyl hydrazide (PDPH), whereby the carbodiimide-activated carboxylate groups of N-acetylmannosaminouronic acid in the CP are coupled to the hydrazide group of PDPH (FIG. 8). The MSCRAMM carrier protein is activated by bromoacetylation of the lysine residues with the N-hydroxysuccimide ester of bromoacetic acid (FIG. 7). The PDPH-thiolated CP is then conjugated to the activated surface adhesin protein by displacement of bromine in the bromoacetylated protein with thiol, resulting in a stable thioether bond (FIG. 9):

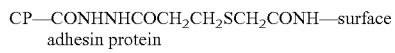
CP—CONHNHCOCH$_2$CH$_2$SCH$_2$CONH—surface adhesin protein

Immunogenic compositions comprising the CP—surface adhesin protein conjugates of the invention were tested in mice, and were shown to possess improved immunogenic properties as compared with the poorly immunogenic unconjugated CP (FIGS. 15-20). In addition, both the capsular polysaccharide specific antibodies and the ClfA and SdrG specific antibodies induced by the CP—surface adhesin conjugate immunogenic compositions were shown to bind to the live strains expressing the corresponding antigens (Tables 5 and 6). In light of these results, it is believed that the immunogenic compositions of the invention will be useful against nosocomial infections caused by pathogens such as S. aureus or S. epidermidis. And when the antibodies induced by CP—surface adhesin conjugates are administered as immunogenic compositions to a wound or used to coat medical devices or polymeric biomaterials in vitro or in vivo, the compositions will prevent or inhibit the binding of staphylococcal bacteria to the wound site or biomaterials. The conjugates that have been processed in accordance with this invention are used in the preparation of immunogenic compositions to confer protection of a subject against nosocomial infections. A "subject" as used herein is a warm-blooded mammal and includes, for instance, humans, primates, horses, cows, dogs and cats.

The conjugates may be added to immunologically acceptable diluents or carriers in the conventional manner to prepare injectable liquid solutions or suspensions.

The immunogenic compositions of the present invention are typically formed by dispersing the conjugate in any suitable pharmaceutically acceptable carrier, such as physiological saline or other injectable liquids. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the composition of the invention. For instance, the conjugate preparation is suspended in sodium phosphate-buffered saline (PBS) (pH 7.0-8.0) at concentrations of 1 to 100 µg of the polysaccharide per ml. The administration of the immunogenic composition of the present invention may be effected by any of the well-known methods, including, but not limited to, parenteral (e.g., subcutaneous, intraperitoneal, intramuscular, intravenous, intradermal), oral and intranasal. The preferred method of administration of the immunogenic composition is parenteral administration. Solutions or suspensions used for parenteral administration include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Immunogenic compositions suitable for injectable use include sterile aqueous solutions (where water soluble) or dispersions and sterile powders for the extemporaneous preparation of sterile injectable solutions or dispersion. In all cases, the composition must be sterile and should be fluid to the extent that easy syringability exists. It must be stable under the conditions of manufacture and storage and must be preserved against the contaminating action of microorganisms such as bacteria and fungi. The carrier is a solvent or dispersion medium containing, for example, water, ethanol, polyol (e.g., glycerol, propylene glycol, and liquid polyethylene glycol, and the like), and suitable mixtures thereof. The proper fluidity is maintained, for example, by the use of a coating such as lecithin, by the maintenance of the required particle size in the case of a dispersion and by the use of surfactants. Prevention of the action of microorganisms is achieved by various antibacterial and antifungal agents, for example, parabens, chlorobutanol, phenol, ascorbic acid, thimerosal, and the like. In many cases, it is preferable to include isotonic agents, for example, sugars, polyalcohols such as mannitol, sorbitol, and sodium chloride in the composition. Prolonged absorption of the injectable compositions is brought about by including in the composition an agent which delays absorption, for example, aluminum monostearate and gelatin.

Sterile injectable solutions are prepared by incorporating a conjugate of this invention in the required amount in an appropriate solvent with one or a combination of ingredients provided above, as required, followed by filtered sterilization. Generally, dispersions are prepared by incorporating the active compound into a sterile vehicle that contains a basic dispersion medium and the required other ingredients from those provided above. In the case of sterile powders for the preparation of sterile injectable solutions, the preferred methods of preparation are vacuum-drying and freeze-drying which yields a powder of the active ingredient plus any additional desired ingredient from a previously sterile-filtered solution thereof.

In certain embodiments, the immunogenic composition will comprise one or more adjuvants. As defined herein, an "adjuvant" is a substance that serves to enhance the immunogenicity of an immunogenic composition of this invention. Thus, adjuvants are often given to boost the immune response and are well known to the skilled artisan.

Preferred adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (see below) or bacterial cell wall components), such as, for example,
   (a) MF59 (PCT Publ. No. WO 90/14837), containing 5% Squalene, 0.5% Tween 80, and 0.5% Span 85 (optionally containing various amounts of MTP-PE (see below, although not required)) formulated into submicron particles using a microfluidizer such as Model 110Y microfluidizer (Microfluidics, Newton, Mass.),
   (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and
   (c) Ribi™ adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL™) described in U.S. Pat. No. 4,912,094 (Corixa), trehalose dimycolate (TDM), and cell wall skeleton (CWS), preferably MPL+CWS (Detox™);

(3) saponin adjuvants, such as Quil A or STIMULON™ QS-21 (Antigenics, Framingham, Mass.) (U.S. Pat. No. 5,057,540) may be used or particles generated therefrom such as ISCOMs (immunostimulating complexes);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113, 918; one such AGP is 2-[(R)-3-Tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also know as 529 (formerly known as RC529), which is formulated as an aqueous form or as a stable emulsion, synthetic polynucleotides such as oligonucleotides containing CpG motif(s) (U.S. Pat. No. 6,207, 646);

(5) cytokines, such as interleukins (e.g., IL-1, IL-2, IL-4, IL-5, IL-6, IL-7, IL-12, IL-15, IL-18, etc.), interferons (e.g., gamma interferon), granulocyte magrophage colony stimulating factor (GM-CSF), macrophage colony stimulating factor (M-CSF), tumor nucrosis factor (TNF), etc.;

(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an E. coli heat-labile toxin (LT), particularly LT-K63, LT-R72, CT-S109, PT-K9/G129 (see, e.g., WO 93/13302 and WO 92/19265); and (7) other substances that act as immunostimulating agents to enhance the effectiveness of the composition.

As mentioned above, muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

The immunogenic compositions of the present invention are administered in amounts sufficient to provoke an immunogenic response. Dosages may be adjusted based on the size, weight or age of the individual receiving the immunogenic composition. The antibody response in an individual can be monitored by assaying for antibody titer or bactericidal activity and boosted if necessary to enhance the response.

The immunogenic compositions of the present invention are administered to a subject to induce a humoral immune response. The subject then acts as a source of immunoglobulin (hyperimmune immunoglobulin) produced in response to the immunogenic composition. The immunized subject donates plasma from which hyperimmune globulin is then obtained, via conventional plasma fractionation technology, and administered to another subject in order to impart resistance against or to treat nosocomial infection.

EXAMPLES

The above disclosure generally describes the present invention. A more complete understanding can be obtained by reference to the following specific Examples. These Examples are described solely for the purpose of illustration and are not intended to limit the scope of the invention.

Example 1

Purification of the S. aureus CP5 and CP8 Polysaccharides

S. aureus strains Lowenstein (ATCC#49521) and Wright (ATCC#49521) were used for purification of CP5 and CP8, respectively. The polysaccharides were purified from the cells by the methods modified from those published previously (Fournier, Vann et al. 1984; Fournier, Hannon et al. 1987). Cells grown in Columbia broth, supplemented with 2% NaCl were digested for 3 hrs at 37° C. with lysostaphin (175 U/g of cells), RNAse, and DNAse (0.1 mg/g of each) for 4 hrs at 37° C., followed by digestion with pronase (1 mg/g of cells) for 3 hrs at 37° C. The crude CP was prepared from enzymatic digest by sequential precipitation with 25% and 75% ethanol in the presence of 10 mM $CaCl_2$. The CP was then purified from the pellet by anion-exchange chromatography on a Q-Sepharose column using a linear gradient of 0.05-0.5 M NaCl. The residual teichoic acid was oxidized with 0.05M NaIO$_4$. After dialysis the CP was then further purified by size-exclusion chromatography on Sephacryl S300 (Amersham Pharmacia Biotech, Piscataway, N.J.) column. The presence of the CP in the fractions was determined by reactivity with *S. aureus* CP5 and CP8 specific antisera.

PIA was purified from heat-extracted, stationary-phase *S. epidermidis* cells and combined with PIA containing culture supernatant as described by Mack, et al. (Mack, Fischer et al. 1996). The extracted material and the culture supernatant were concentrated using a 10K membrane and treated to remove nucleic acids and residual proteins. Crude PIA was fractionated using gel filtration or diafiltration. PIA antigen positive material was fractionated further by anion exchange chromatography to purify the PIA fraction containing ester-linked succinate. The flow-through fraction, containing non-succinylated and partially non-N-acetylated PIA, was purified by cation exchange chromatography. The PS/A (PNSG, PNAG) was purified as described by (Maira-Litran, Kropec et al. 2002) or McKenney, Pouliot et al. 1999.

Example 2

Analysis of *S. aureus* CP5 and CP8

Chemical characterization of the purified CP5 and CP8 demonstrated that both polysaccharides were practically free of nucleic acids and residual protein (Table 1).

Figure 2:
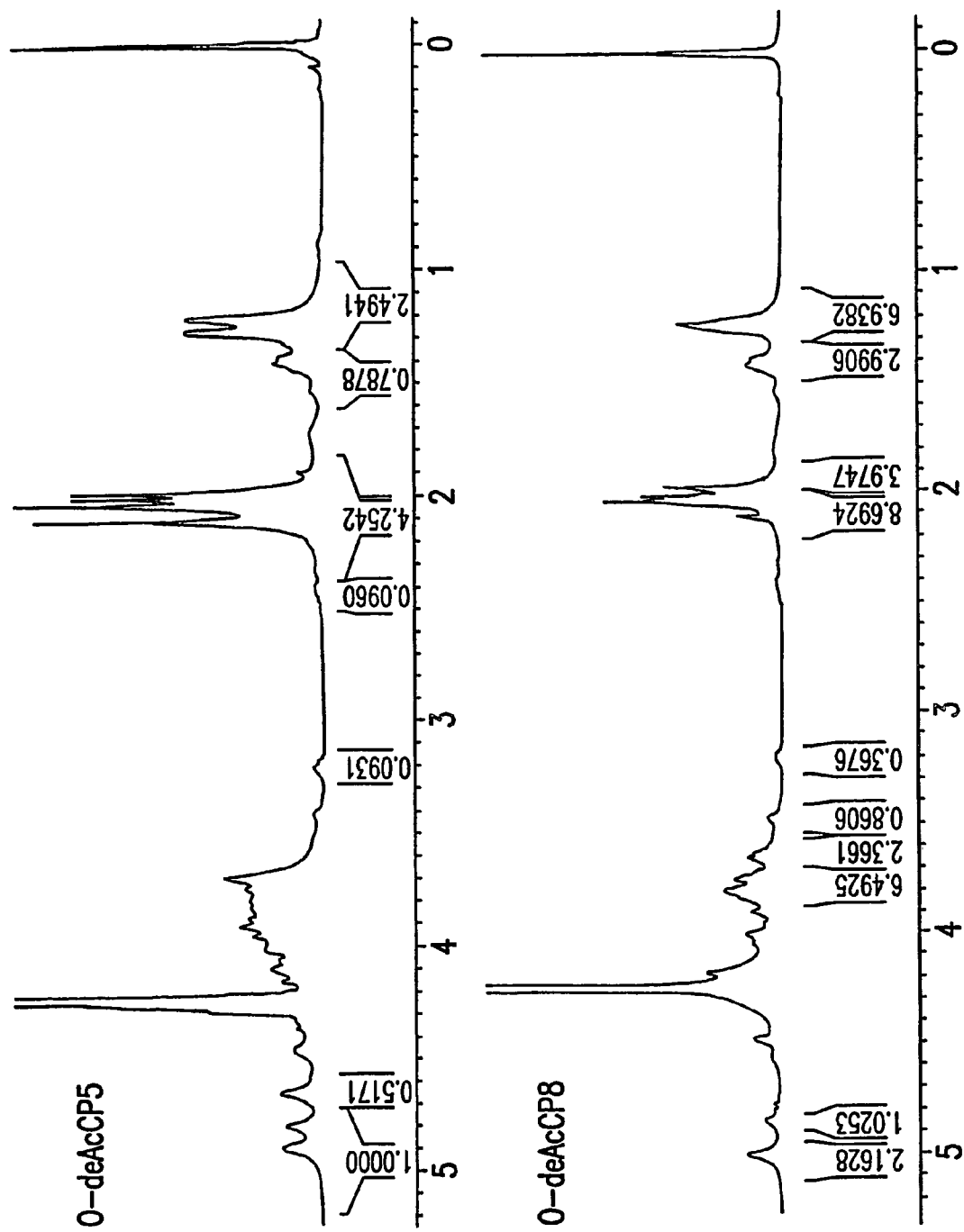
FIG. 2 shows $^1$H-NMR analysis of de-O-Acetylated S. aureus CP5 and CP8.

Sugar composition determined by HPAEC chromatography revealed the presence of Fuc$_p$NAc and Man$_p$NAcA in CP5 and CP8 (FIG. 1). $^1$H NMR spectra of O-deacetylated polysaccharides (FIG. 2) were similar to the spectra previously published (Vann, Moreau et al. 1987; Moreau, Richards et al. 1990), confirming the structure and presence of three monosaccharides: 2-acetamido-2-deoxy-D-mannuronic acid, 2-acetamido-2-deoxy-L-fucose and 2-acetamido-2-deoxy-D-fucose.

Purified CP5, CP8 and TA were immunologically distinct as confirmed by a single precipitin band in a double immunodiffusion assay when reacted with corresponding whole cell antisera (data not presented).

Example 3

Purification of Surface Adhesin Proteins

Figure 3:
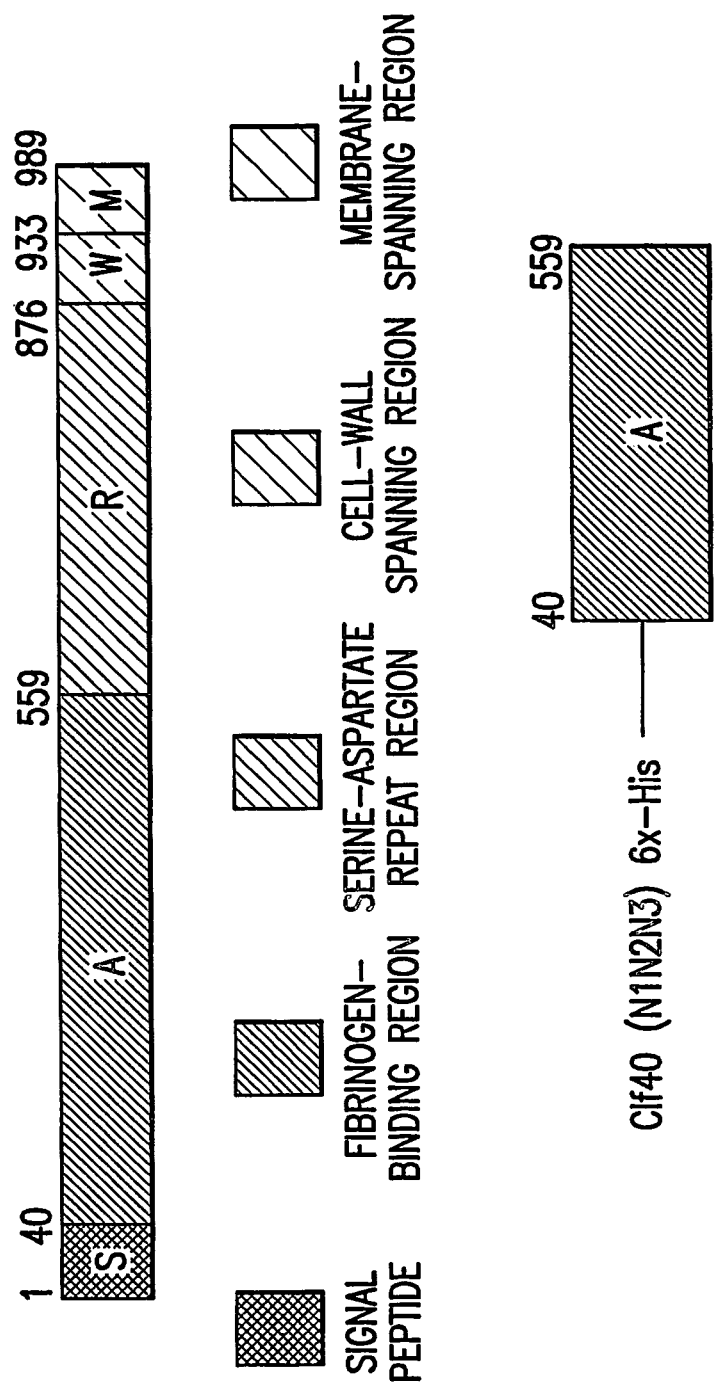
FIG. 3 is a schematic representation of clumping factor from S. aureus—ClfA.
Figure 4:
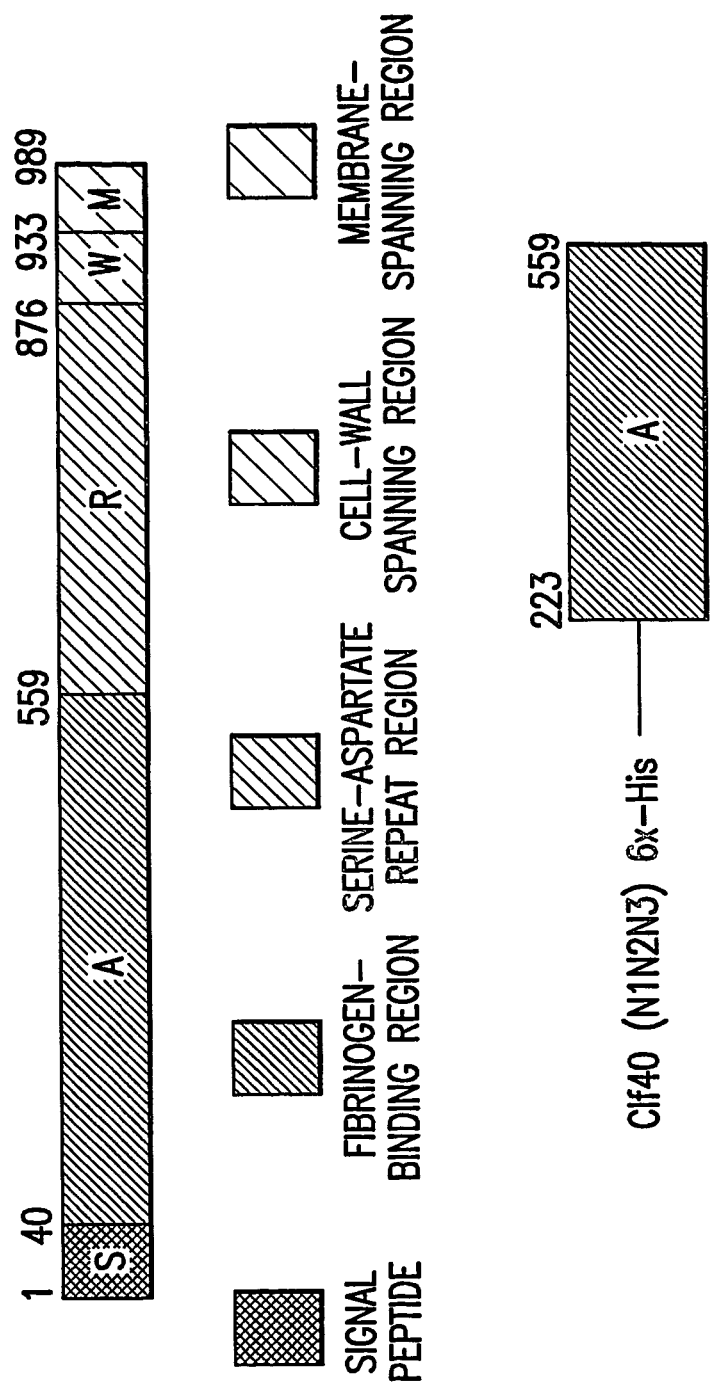
FIG. 4 is a schematic representation of recombinant proteins Clf40 and Clf41 derived from S. aureus ClfA.
Figure 5:
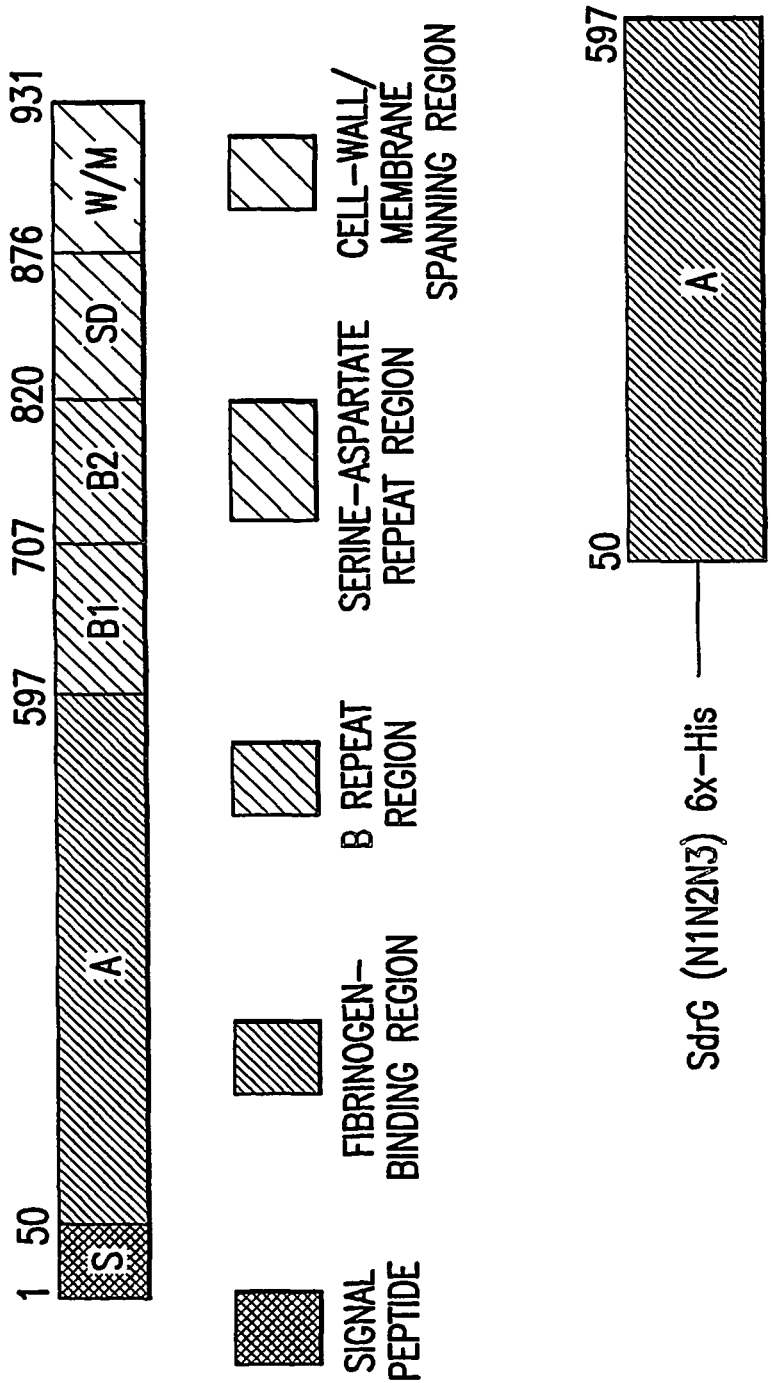
FIG. 5 is a schematic representation of clumping factor from S. epidermis—SdrG.
Figure 6:
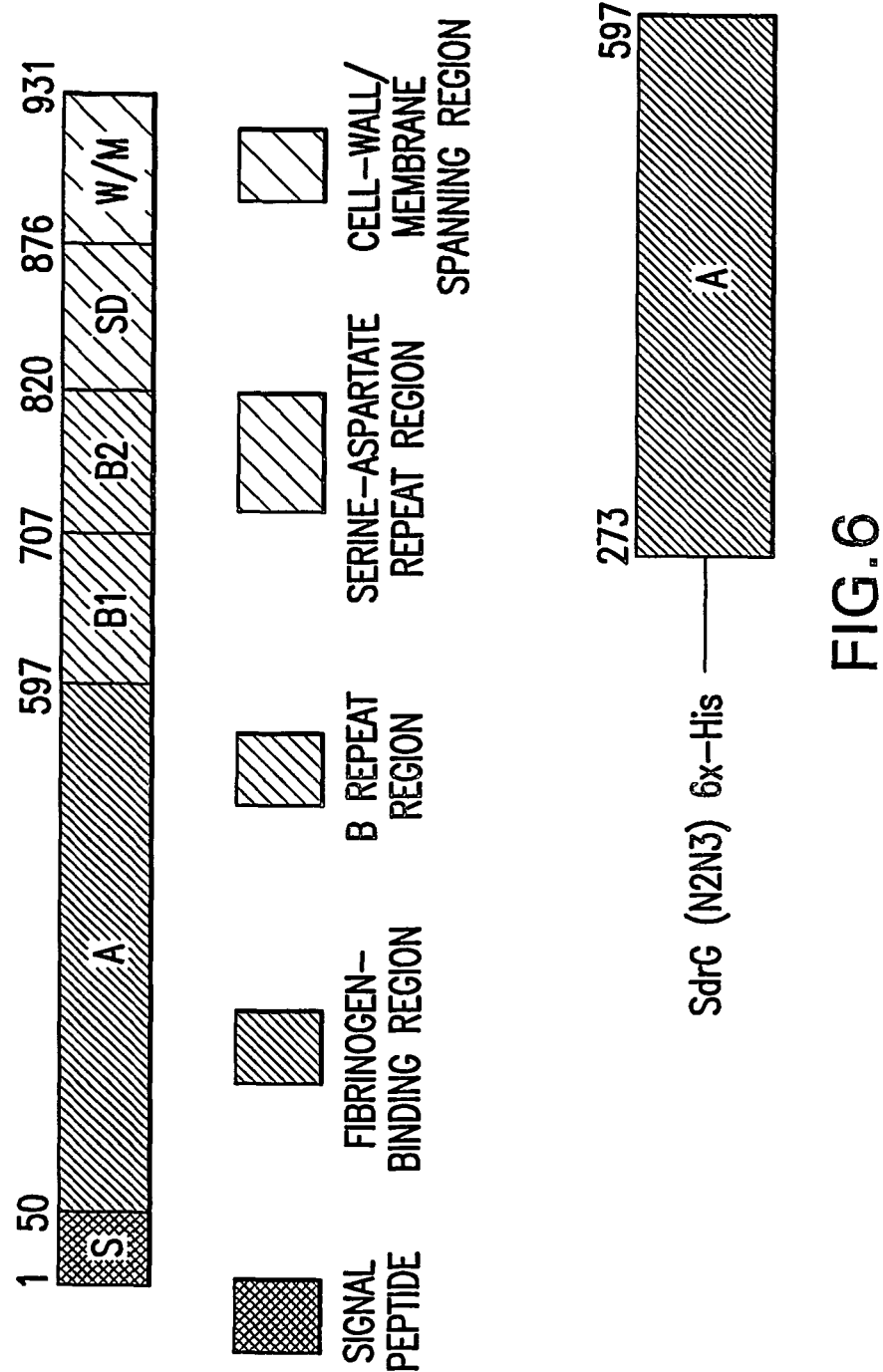
FIG. 6 is a schematic representation of recombinant proteins derived from S. epidermidis SdrG: SdrG (N1N2N3) and SdrG (N2N3).

The surface adhesin proteins evaluated were—
*S. aureus* Clf40 (N1N2N3)—full length A domain of Clumping factor A (amino acids (AA) 40-559)—FIG. 3.
*S. aureus* Clf41 (N2N3)—post protease site fragment of Clf 40 (AA 223-559)—FIG. 4.
*S. epidermidis* SdrG (N1N2N3)—full length A domain of SdrG (AA 50-597)—FIG. 5.
*S. epidermidis* SdrG (N2N3)—post protease site fragment of SdrG (AA 273-597)—FIG. 6.

These surface adhesin proteins were obtained from Inhibitex, Inc., Alpharetta, Ga., USA.

Histag-minus versions of surface adhesin proteins were purified from the *E. coli* plasmid host strains. The *E. coli* pLP1134 BL21 (DE3) was used for *S. aureus* ClfA41 (N2, N3) and pLP1135 B21 (DE3) for *S. epidermidis* SdrG (N2, N3) purification. Both proteins were isolated from soluble fractions of cell lysate by ammonium sulfate precipitation and subsequent ion-exchange chromatography on a Sephacryl Q-Sepharose column (Amersham Pharmacia Biotech, Piscataway, N.J.). The purity of the final material was higher than 90% as determined by SDS-PAGE.

*E. coli* cells containing overexpressed *S. aureus* Clf40 (N1, N2,N3) or Clf41 (N2, N3), *S. epidermidis* SdrG (N1,N2,N3) or SdrG (N2,N3) were solubilized in a single pass through a Microfluidics M10-Y Microfluidizer at about 13000 psi. The cell debris was removed by centrifugation at 17000 rpm for 30 minutes at 4° C. Overexpressed proteins were purified from the supernatant using an AKTAexplorer, XK columns Chelating Sepharose Fast Flow and Q Sepharose HP resins (Amersham Pharmacia Biotech, Piscataway, N.J.). The crude His-tagged protein was purified from the supernatant by an affinity step with Chelating Sepharose Fast Flow charged with 0.1 M NiCl$_2$. The crude lysate was loaded onto the column equilibrated with 25 mM Tris, pH 8.0, 0.5M NaCl, 5 mM imidazole and unbound proteins were eluted from the column by washing the column with five column volumes of the buffer. The bound protein was then eluted with 25 mM Tris, pH 8.0, 0.5M NaCl, 500 mM imidazole buffer and collected in bulk. The protein was then further purified from remaining impurities by ion-exchange chromatography on a Q Sepharose HP column.

Example 4

Synthesis of *S. aureus* CP5- and CP8-Surface Adhesin Carrier Protein Conjugate Immunogenic Compositions

Figure 9:
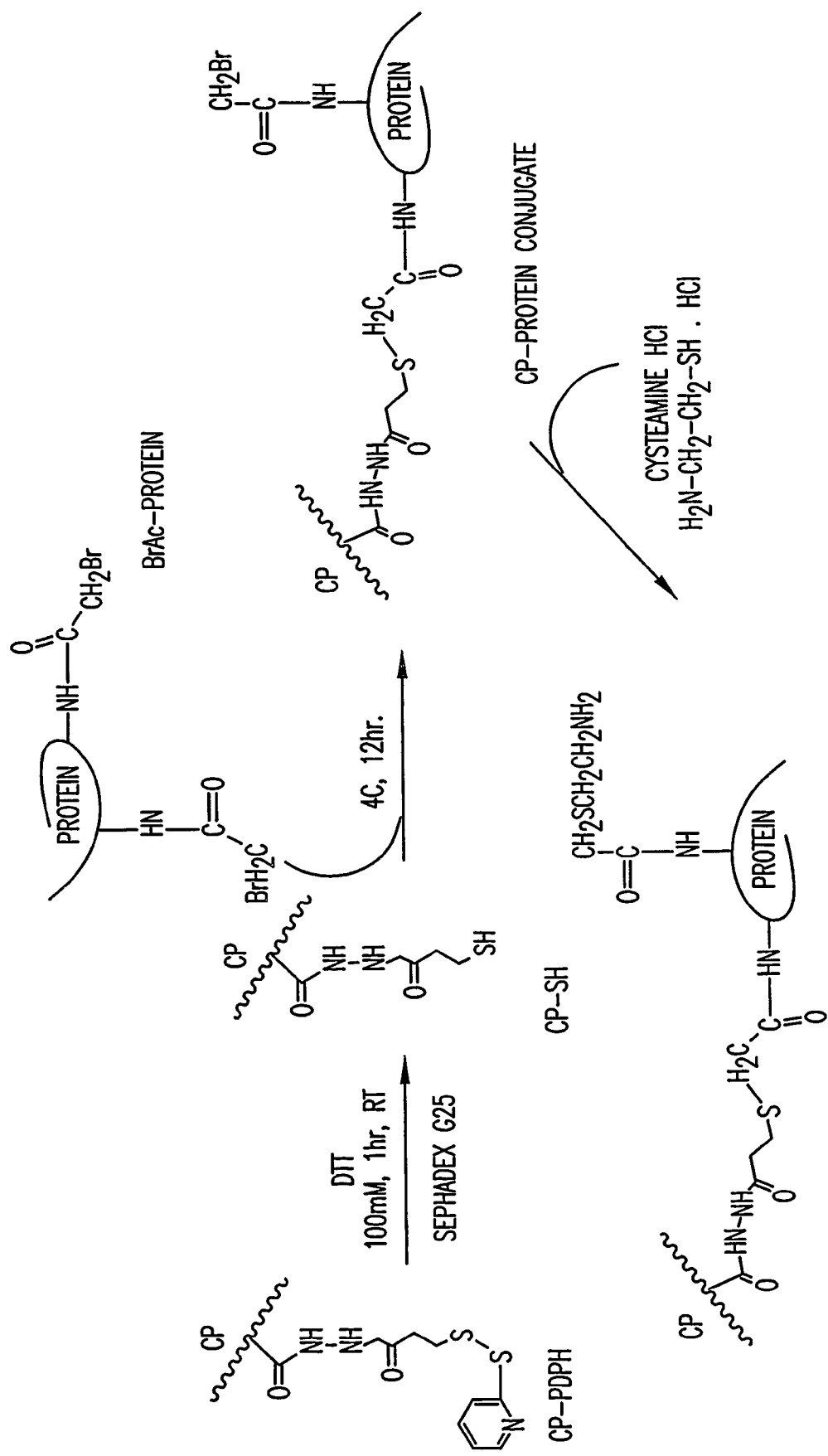
FIG. 9 shows conjugation of thiolated S. aureus CP to an surface adhesin protein.
Figure 10:
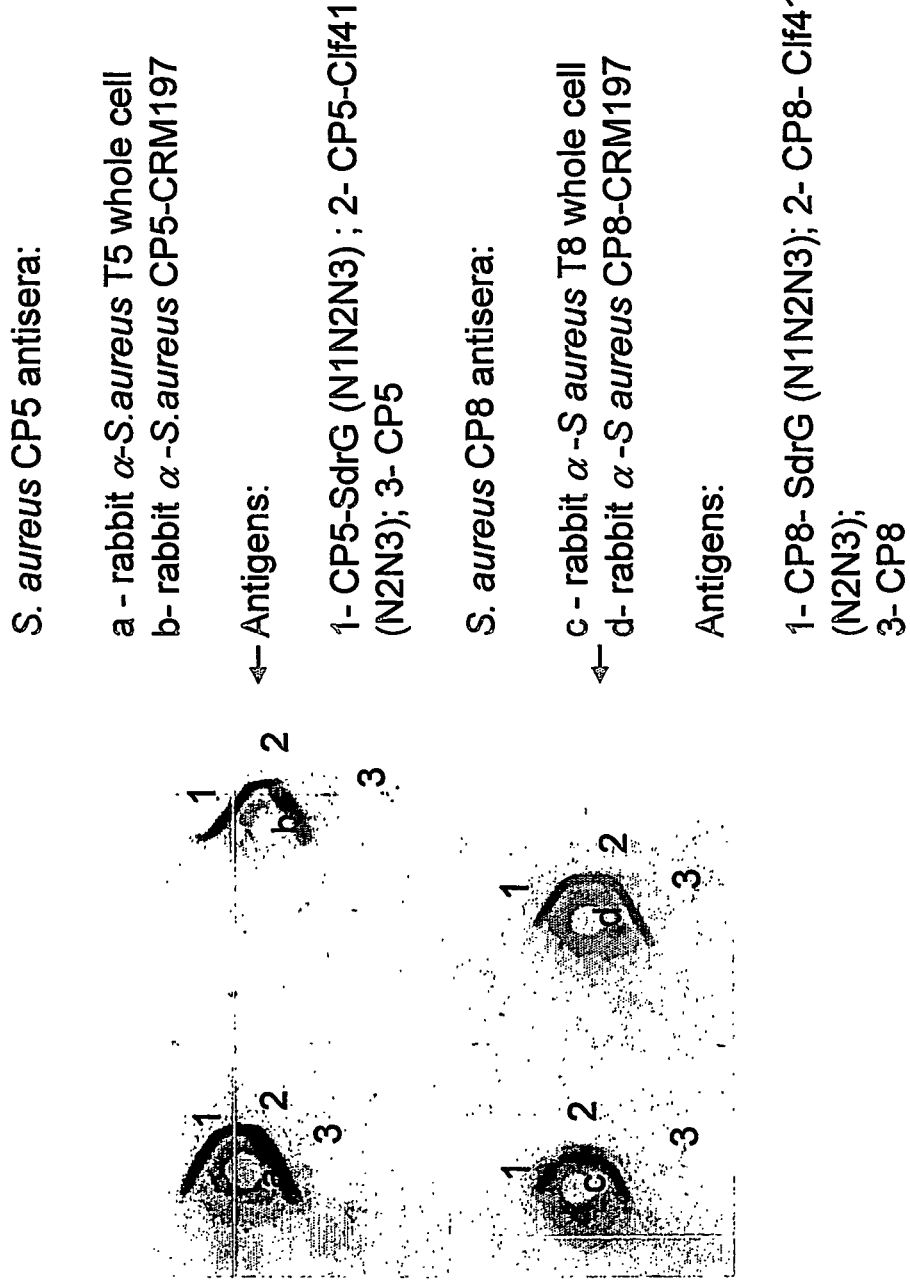
FIG. 10 shows analysis of CP5- and CP8-SdrG (N1N2N3) and CP5- and CP8-Clf41(N2N3) conjugates for antigenicity with CP specific rabbit antisera.
Figure 11:
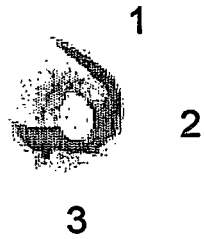
FIG. 11 shows analysis of CP5- and CP8-Clf41(N2N3) conjugates for antigenicity with a ClfA specific rabbit antisera.
Figure 12:
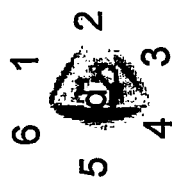
FIG. 12 shows analysis of CP5- and CP8-SdrG (N2N3) 6×His and CP5- and CP8-Clf40 (N1N2N3) 6×His conjugates for antigenicity by double immunodiffusion assay.
Figure 13:
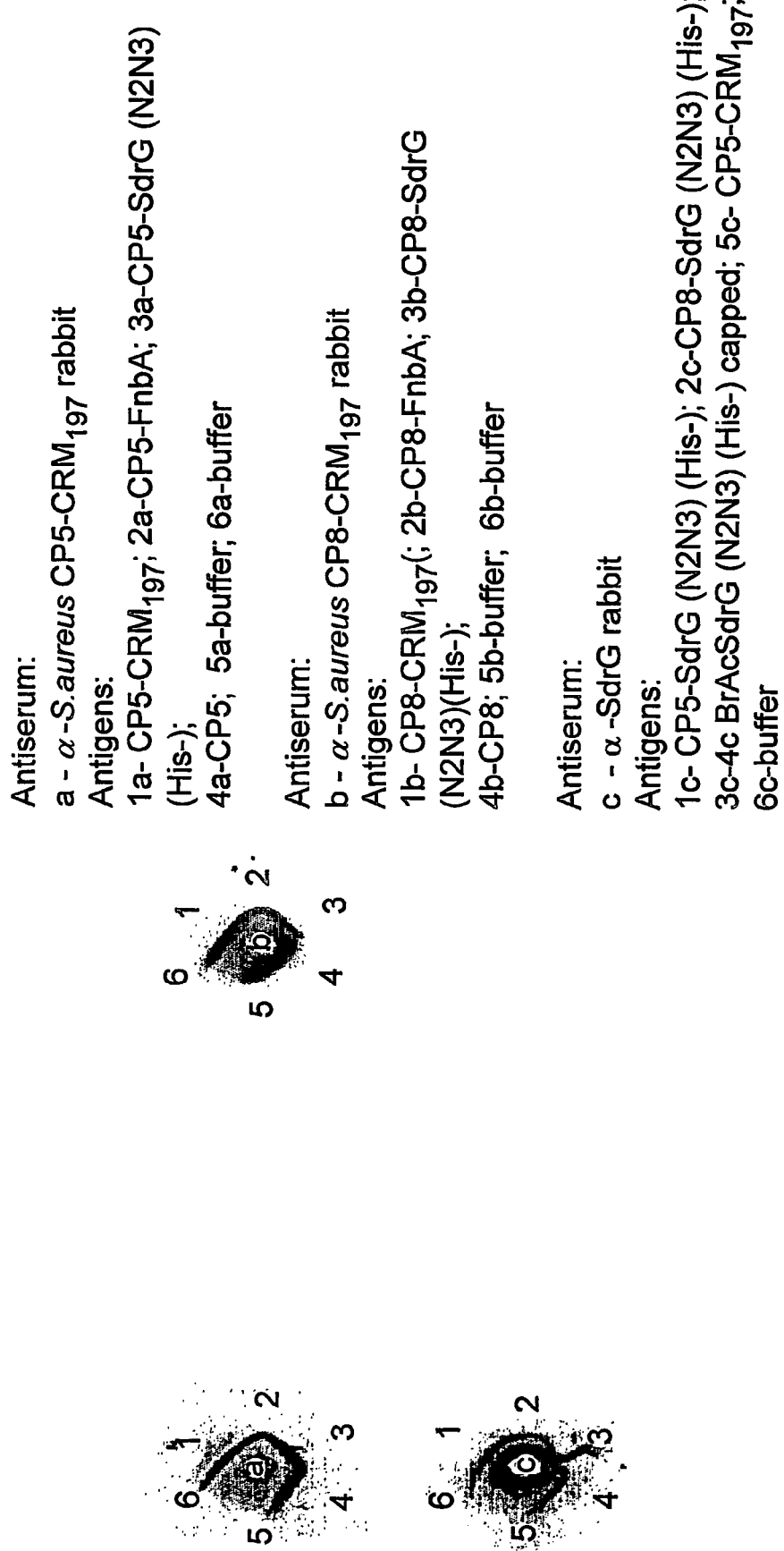
FIG. 13 shows analysis of CP5- and CP8-SdrG (N2N3) and CP5- and CP8-FnbA conjugates for antigenicity by Ouchterlony immunodiffusion assay.
Figure 15A:
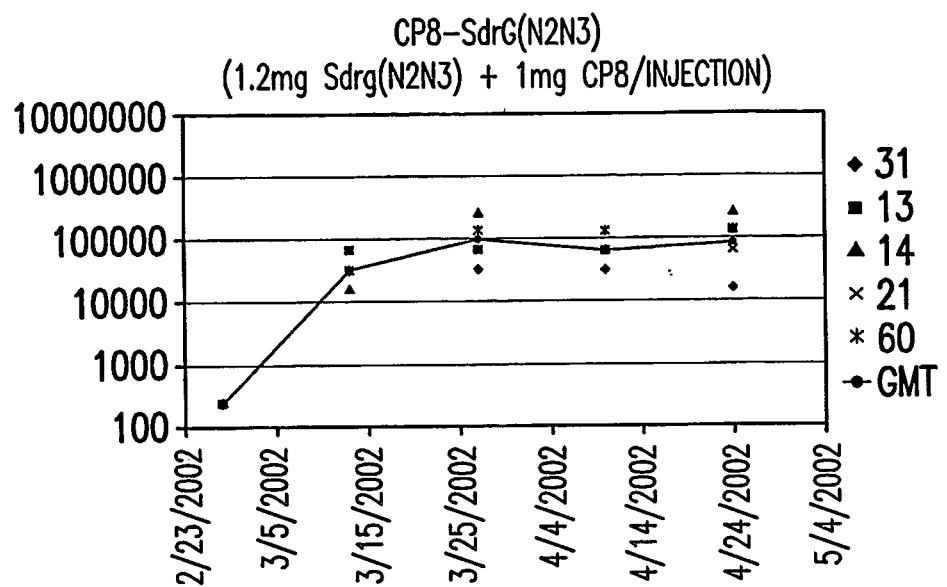
FIGS. 15A-H show the immune response to S. aureus CP8 conjugated to SdrG (N1N2N3), SdrG (N2N3), Clf40 (N1N2N3) and Clf41 (N2N3).
Figure 15B:
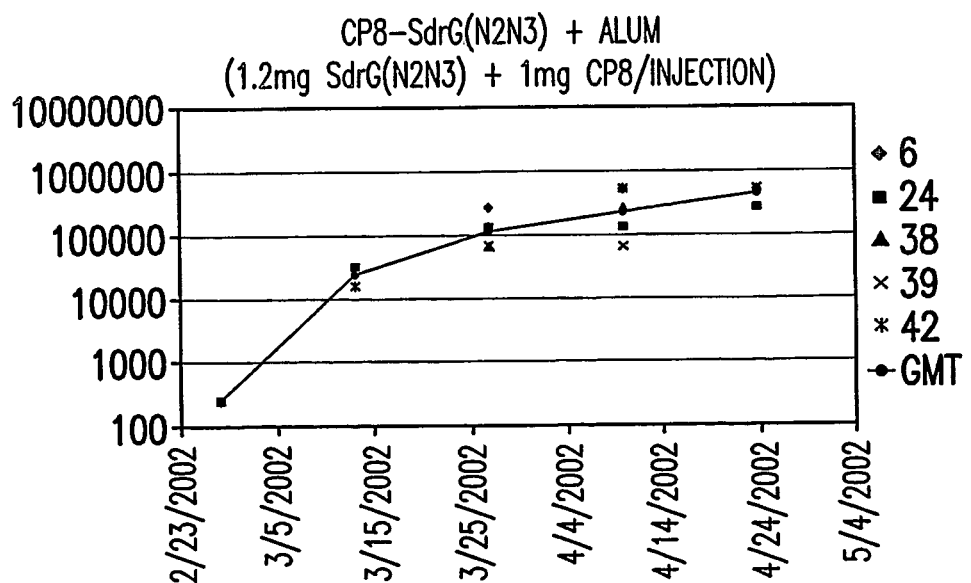
Figure 15C:
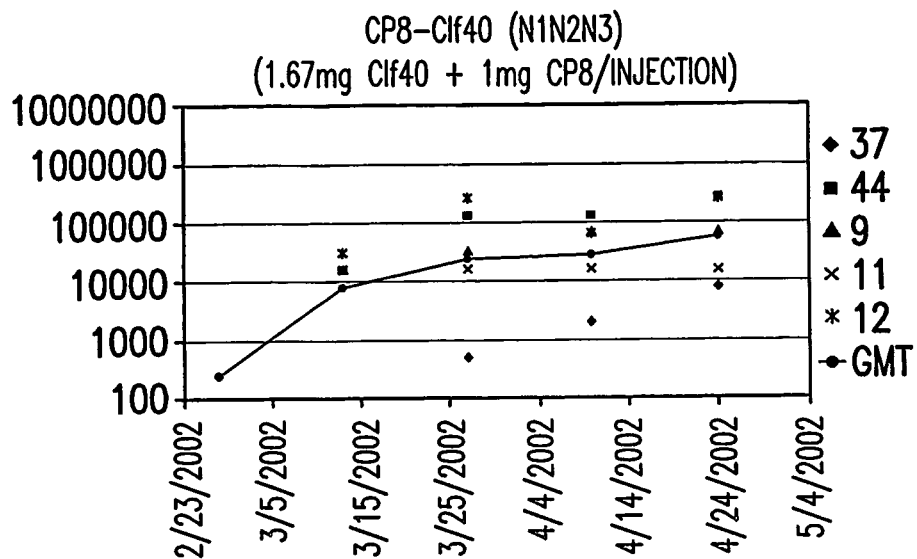
Figure 15D:
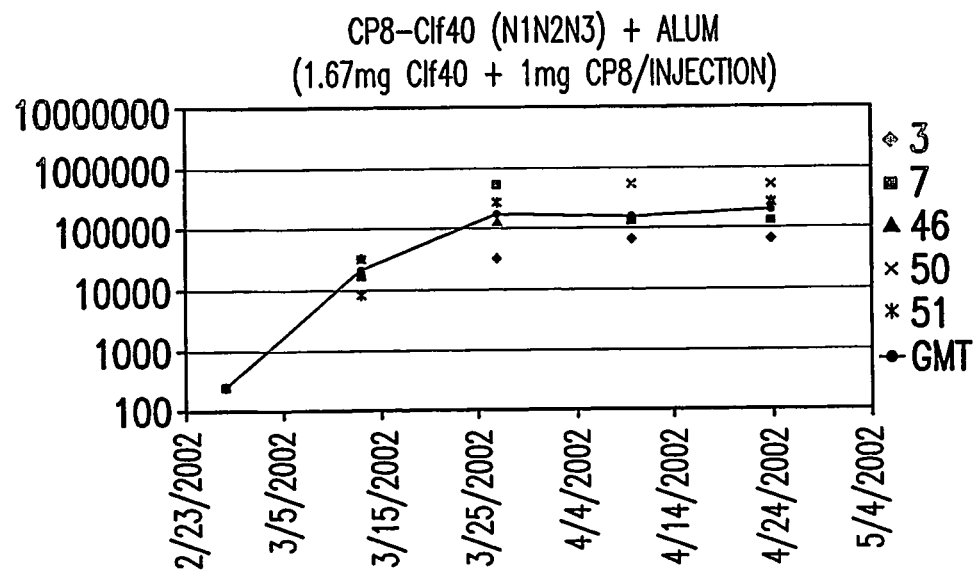
Figure 15E:
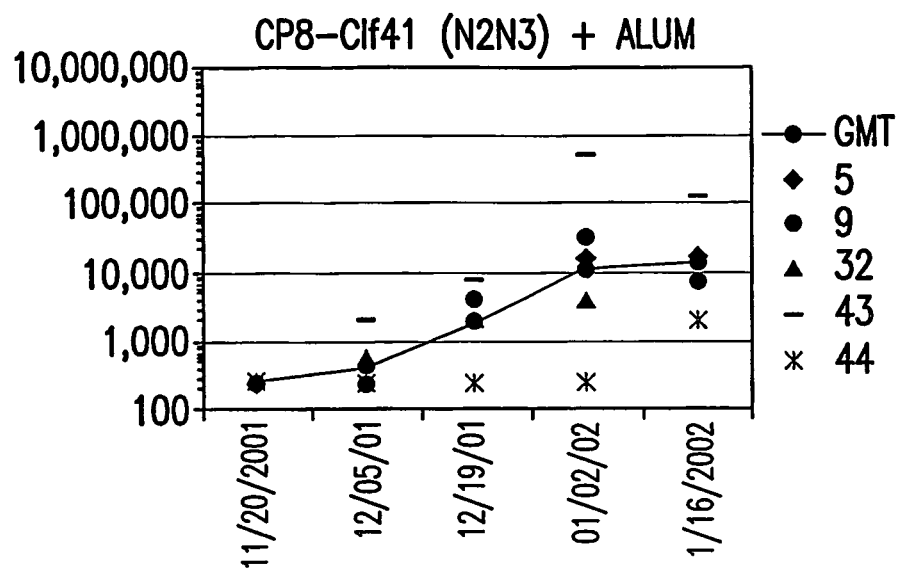
Figure 15F:
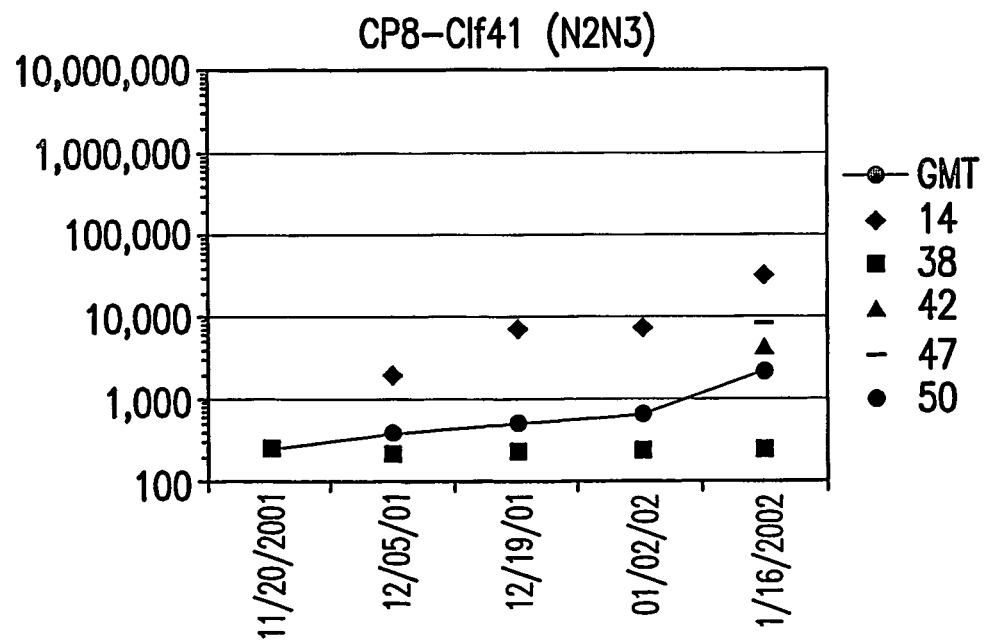
Figure 15G:
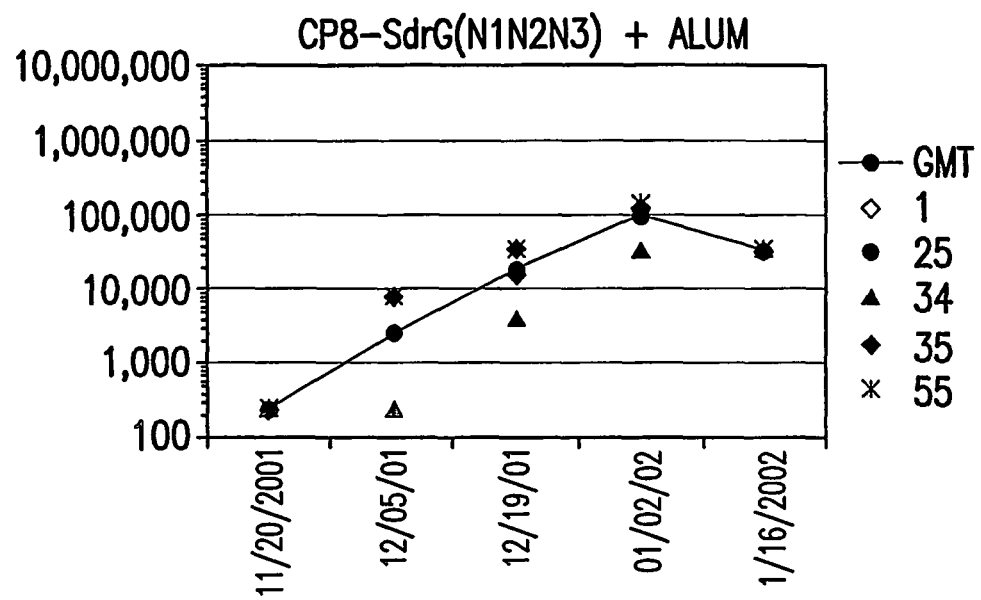
Figure 15H:
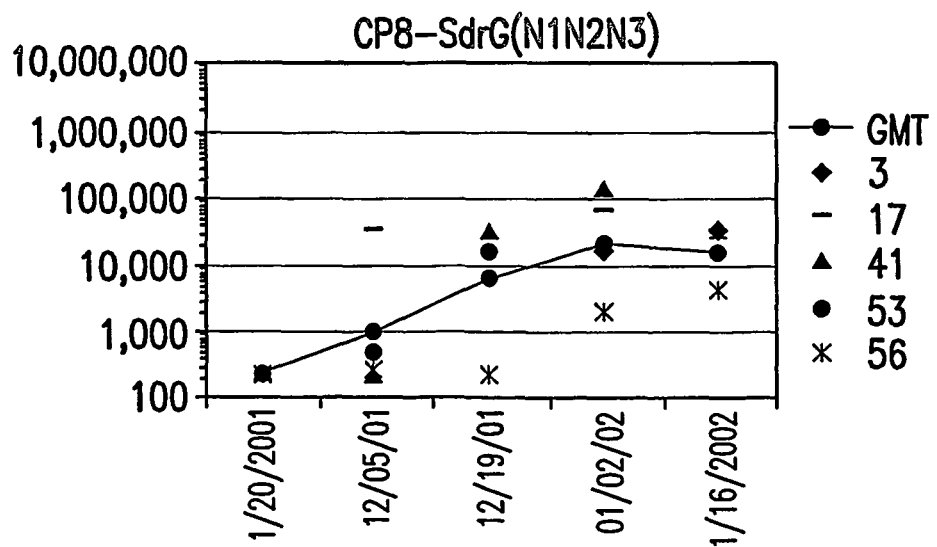
Figure 16A:
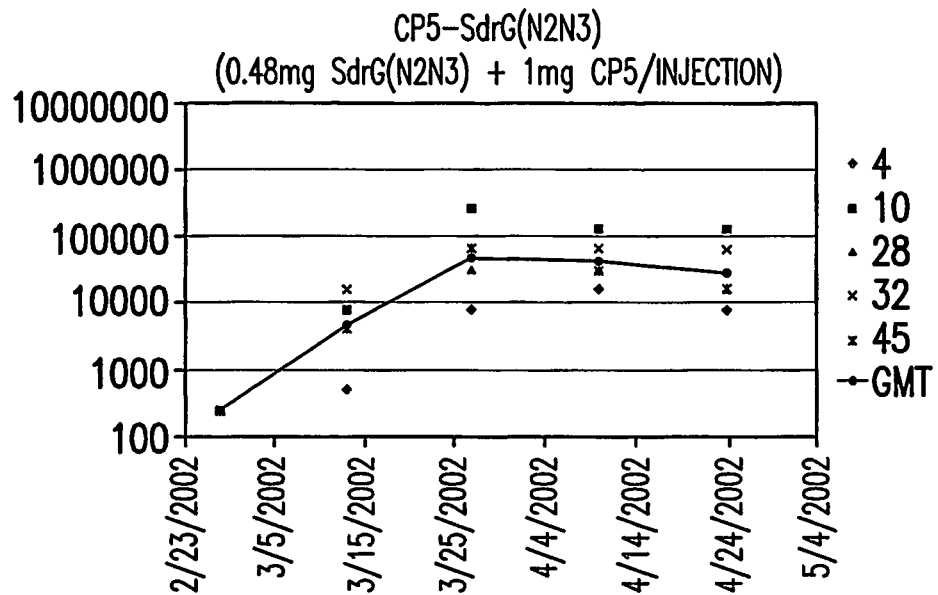
FIGS. 16A-H show the immune response to S. aureus CP5 conjugated to SdrG (N1N2N3), SdrG (N2N3), Clf40 (N1N2N3) and Clf41 (N2N3).
Figure 16B:
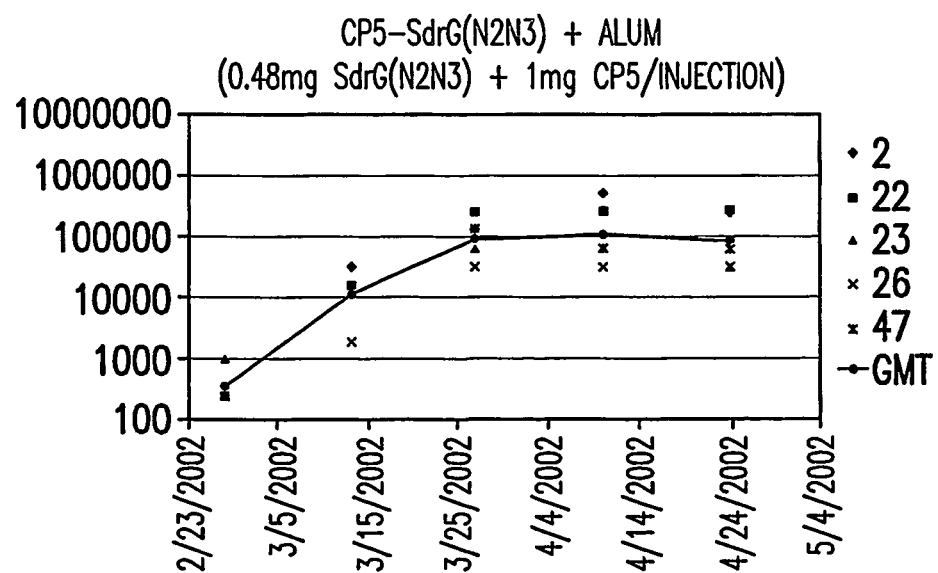
Figure 16C:
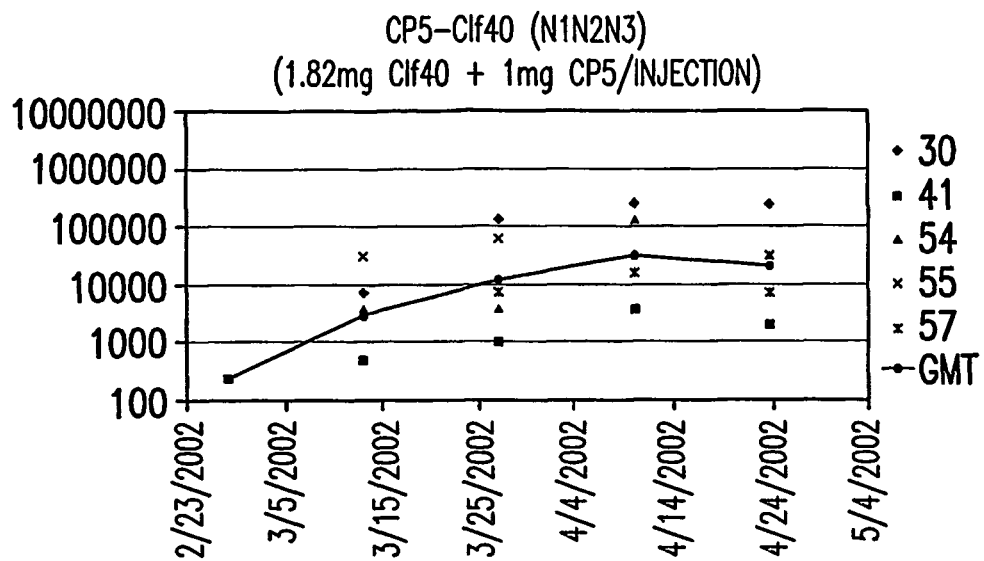
Figure 16D:
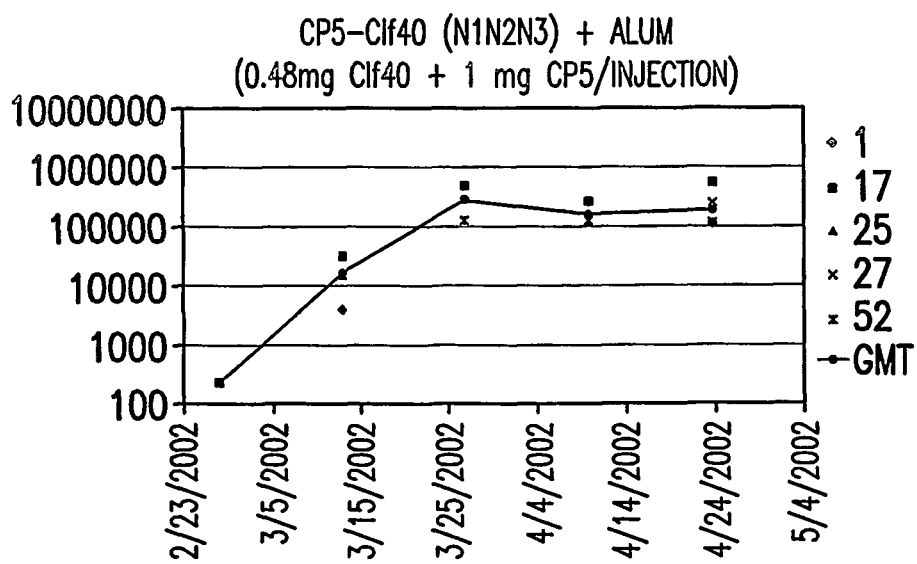
Figure 16E:
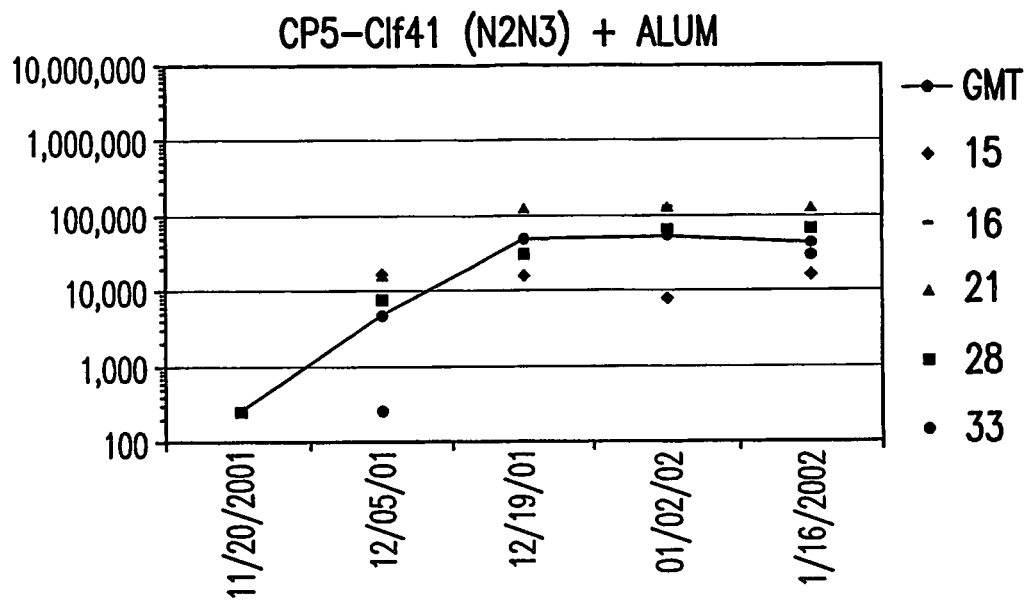
Figure 16F:
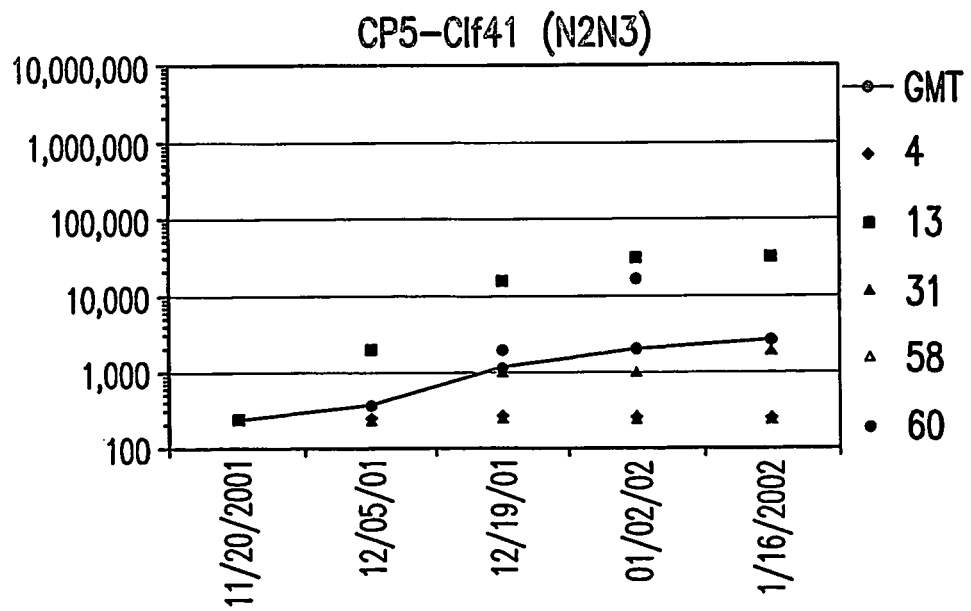
Figure 16G:
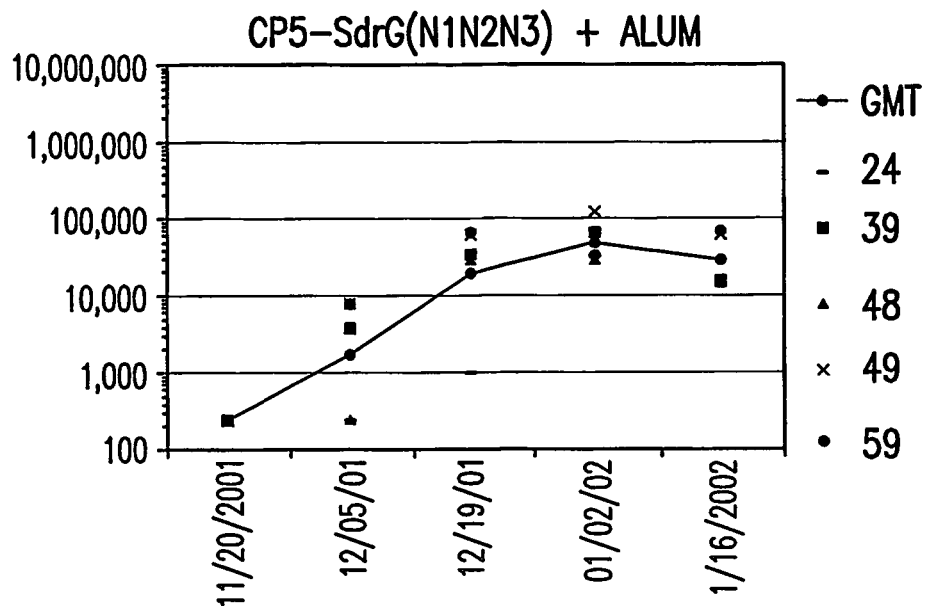
Figure 16H:
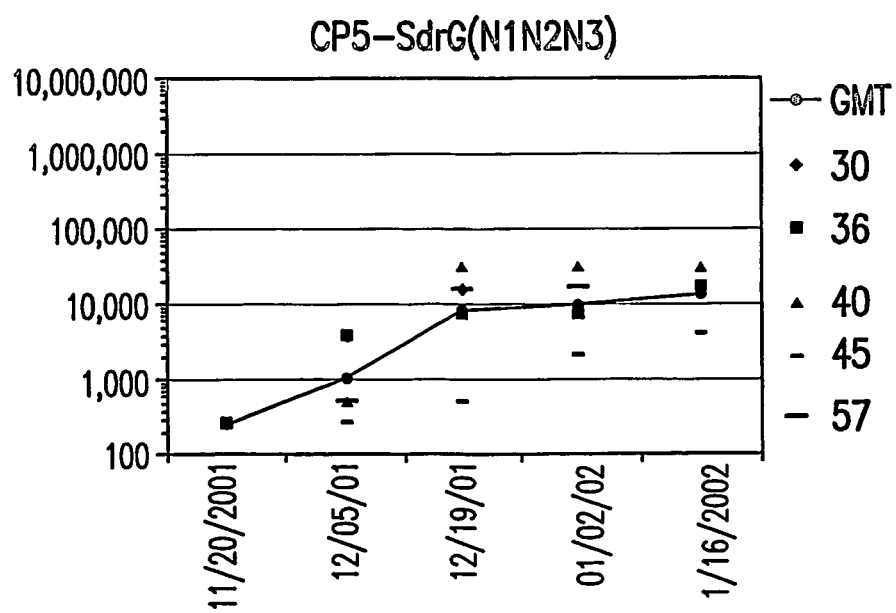
Figure 17A:
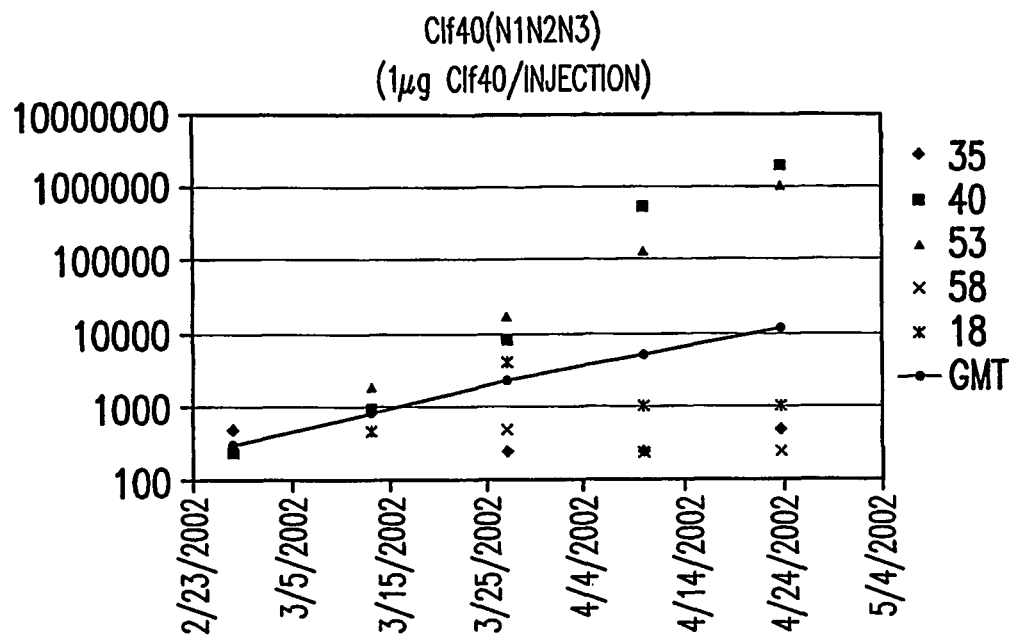
FIGS. 17A-F show the immune response to conjugated and unconjugated S. aureus ClfA (N1N2N3) with and without adjuvant.
Figure 17B:
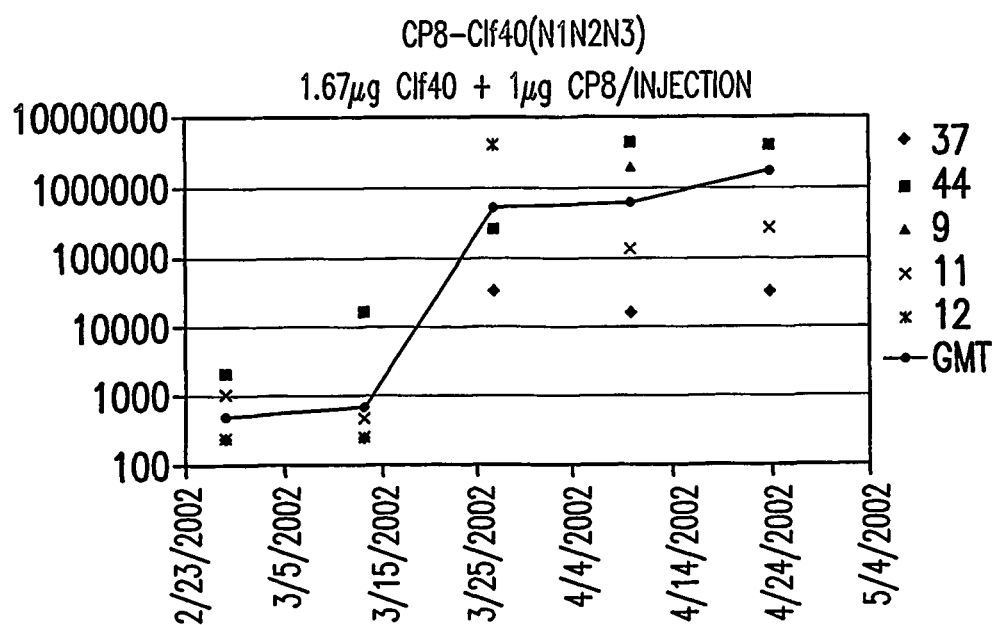
Figure 17C:
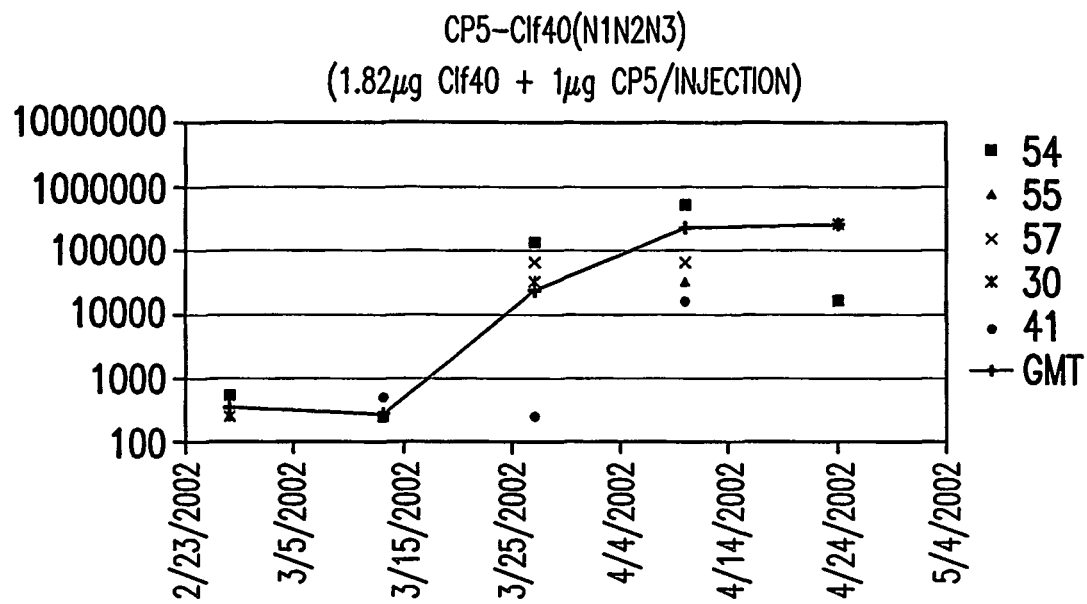
Figure 17D:
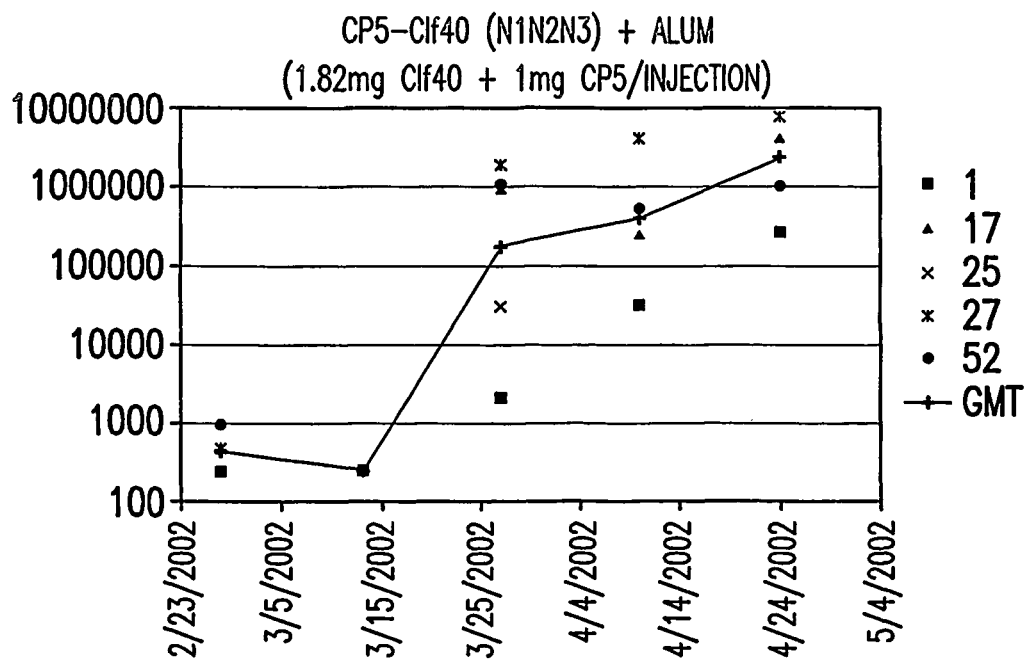
Figure 17E:
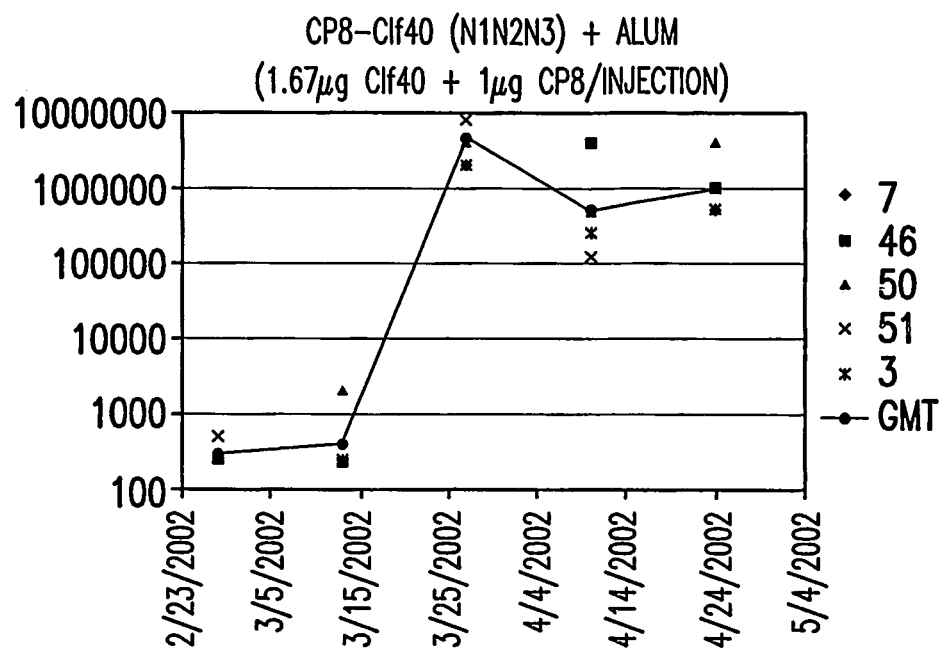
Figure 17F:
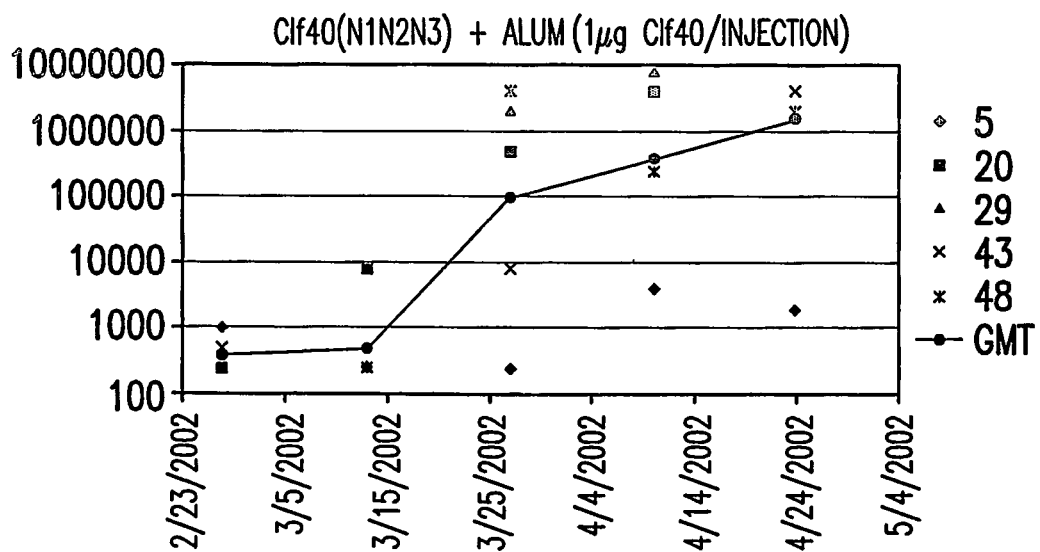
Figure 18A:
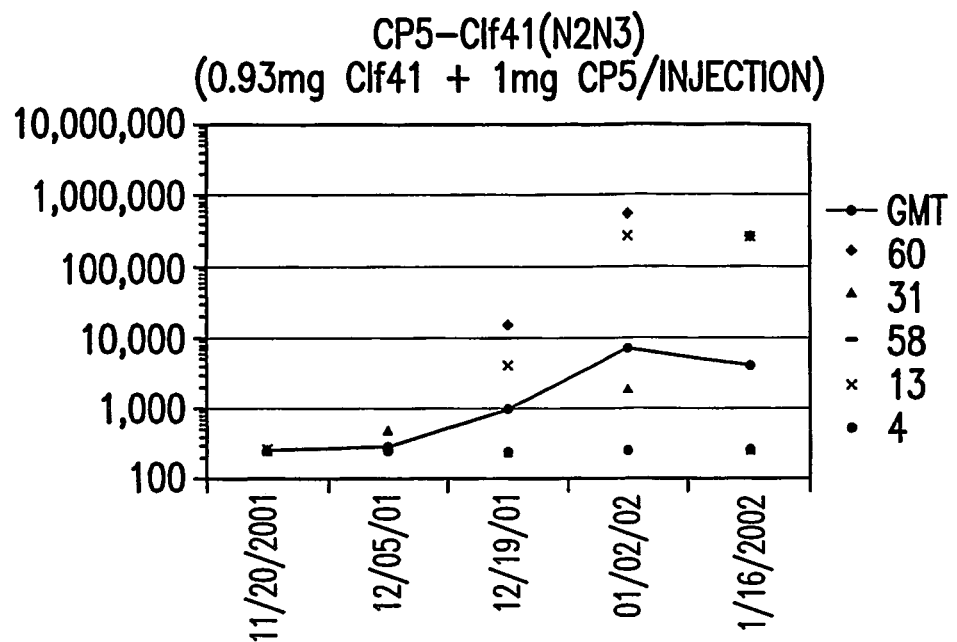
FIGS. 18A-F show the immune response to conjugated and unconjugated *S. aureus* ClfA (N2N3) with and without adjuvant.
Figure 18B:
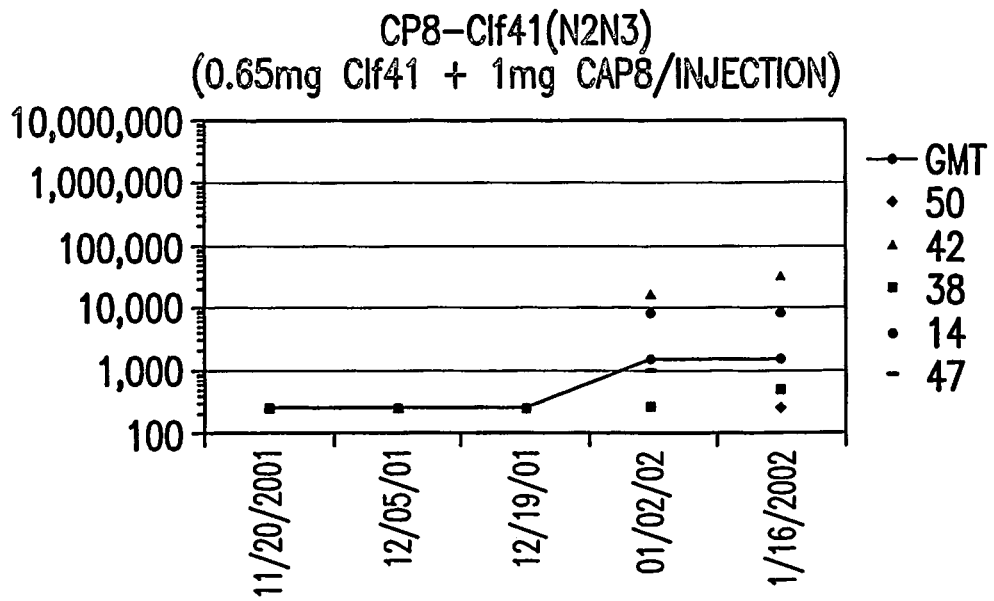
Figure 18C:
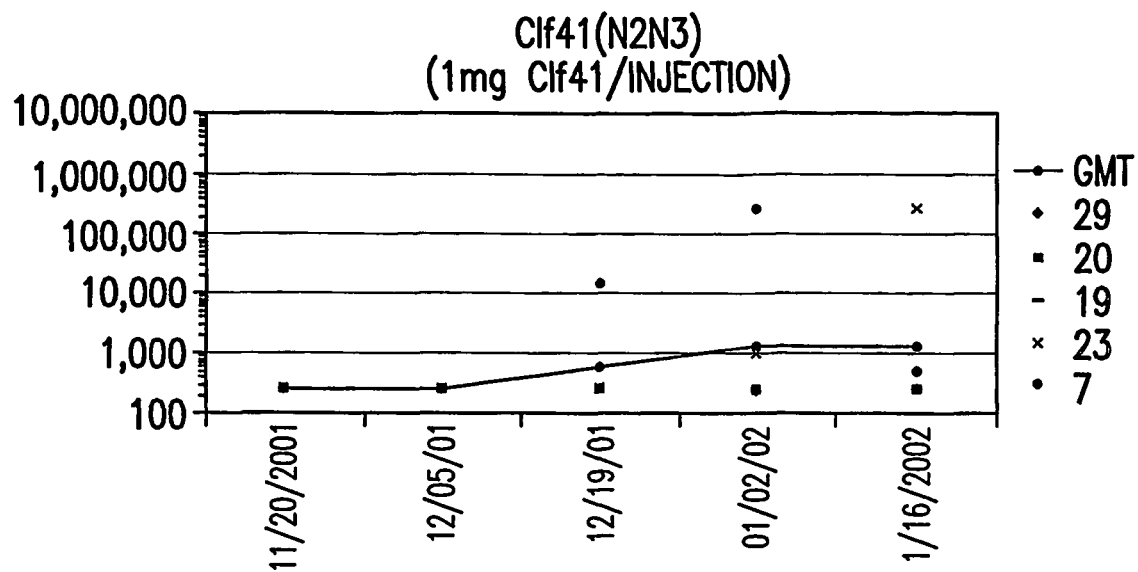
Figure 18D:
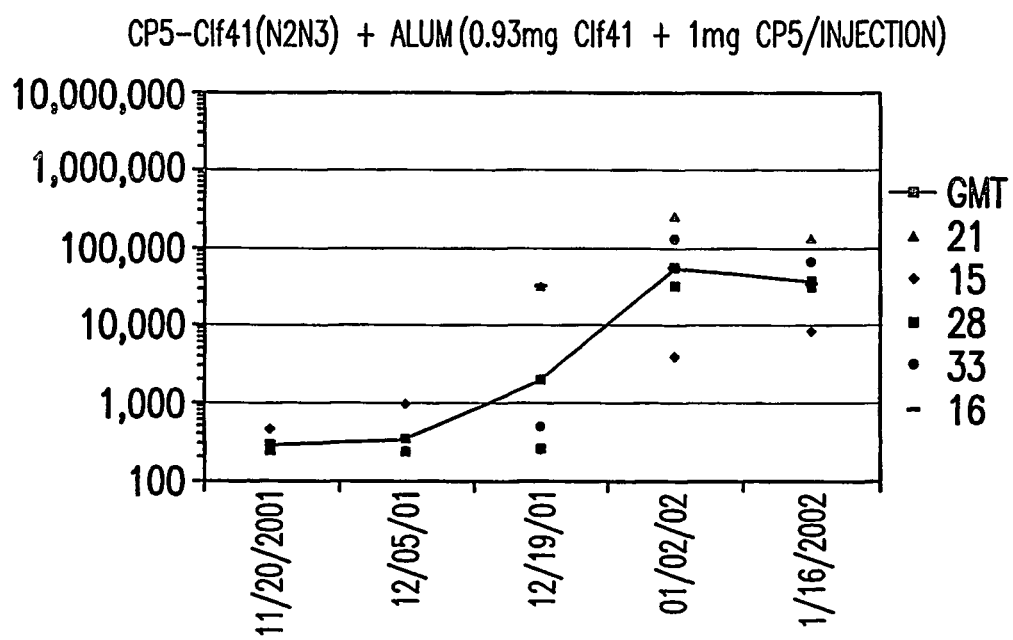
Figure 18E:
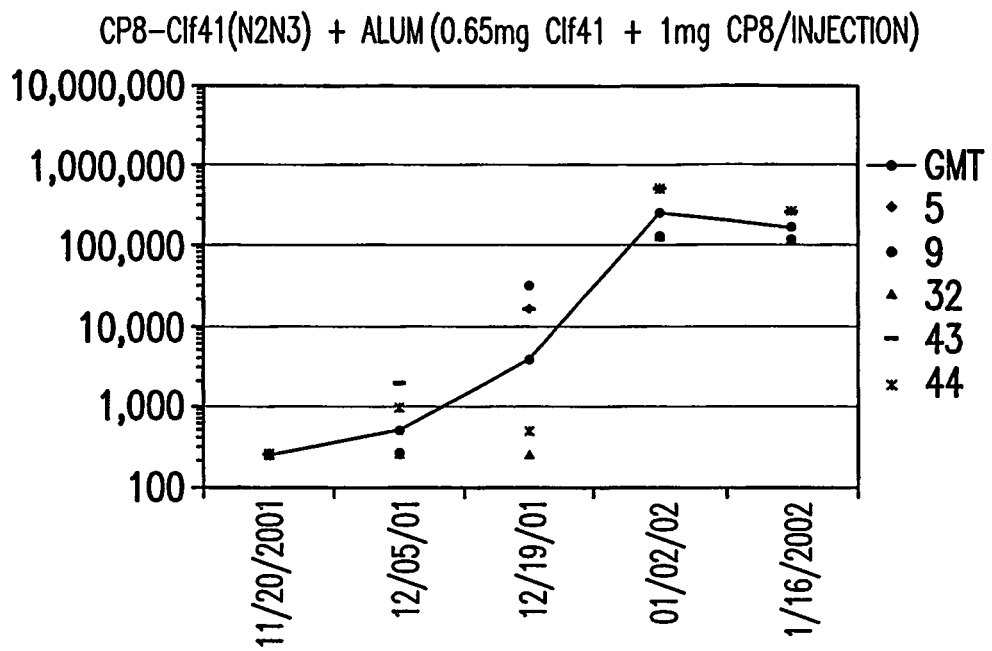
Figure 18F:
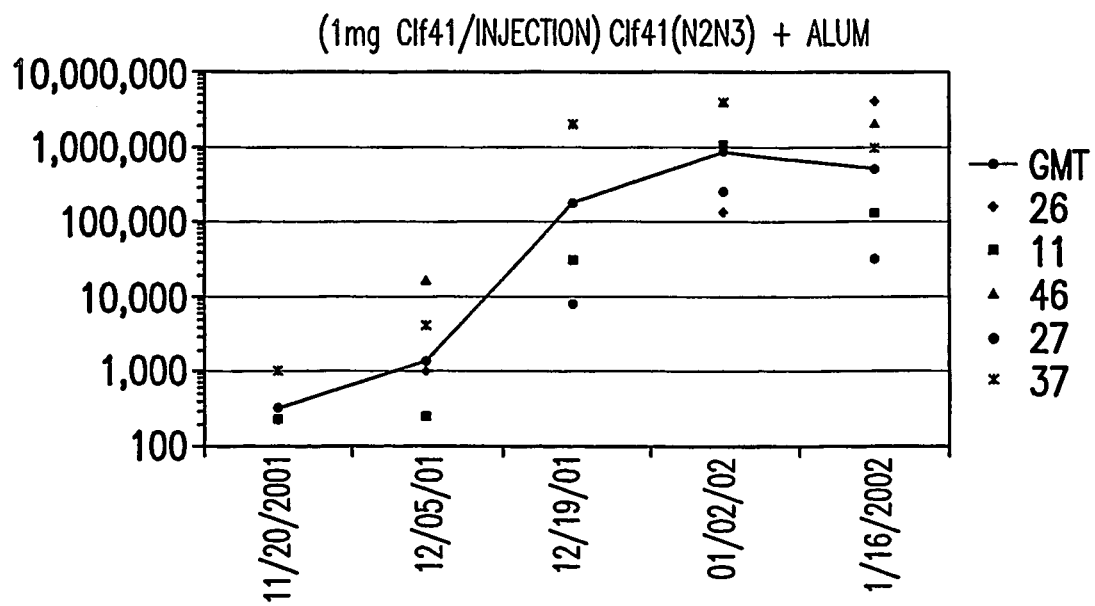
Figure 19A:
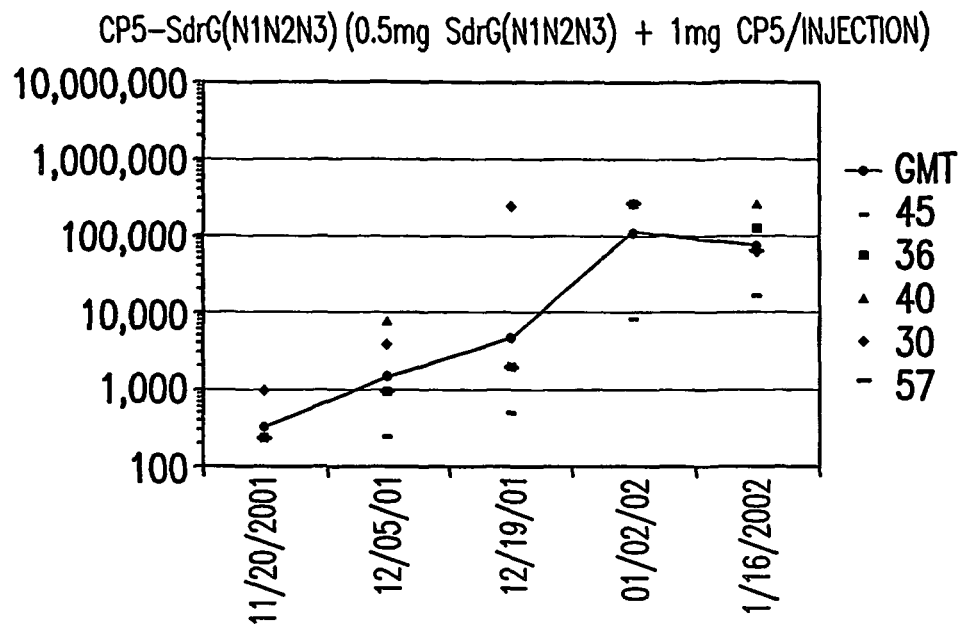
FIGS. 19A-F show the immune response to conjugated and unconjugated *S. epidermidis* SdrG (N1N2N3) with and without adjuvant.
Figure 19B:
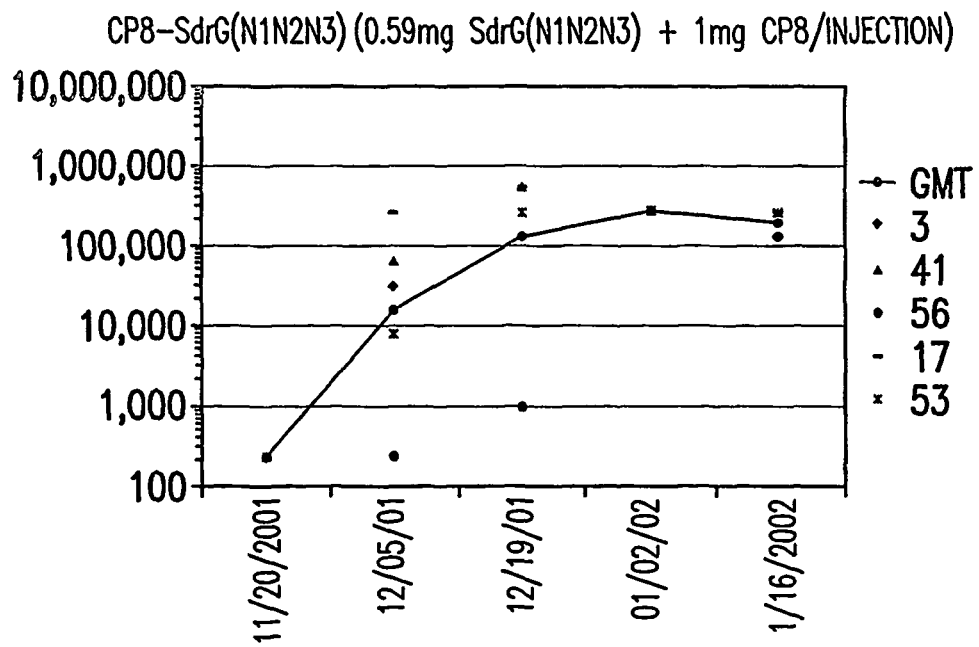
Figure 19C:
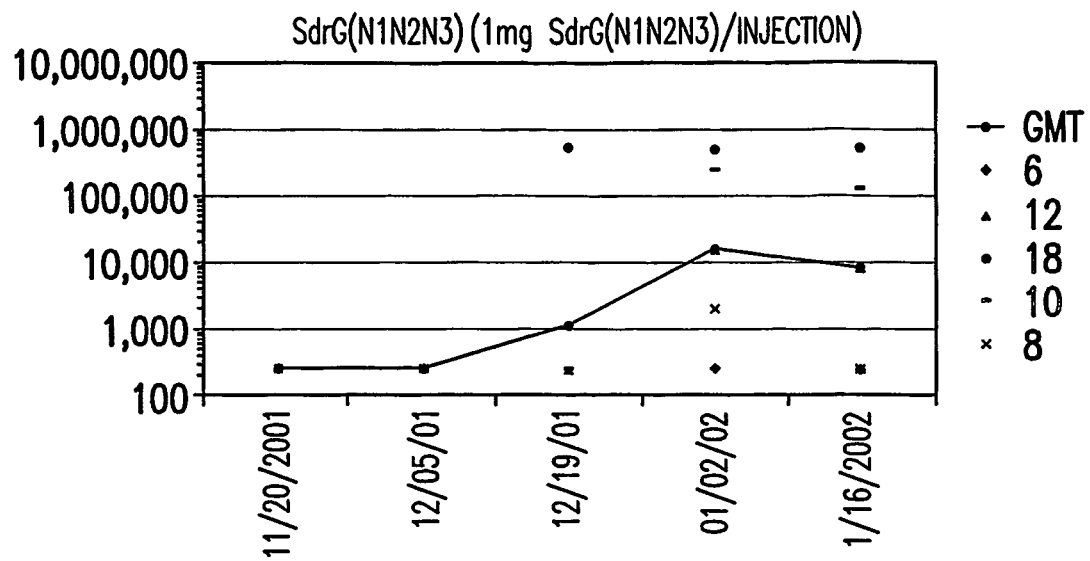
Figure 19D:
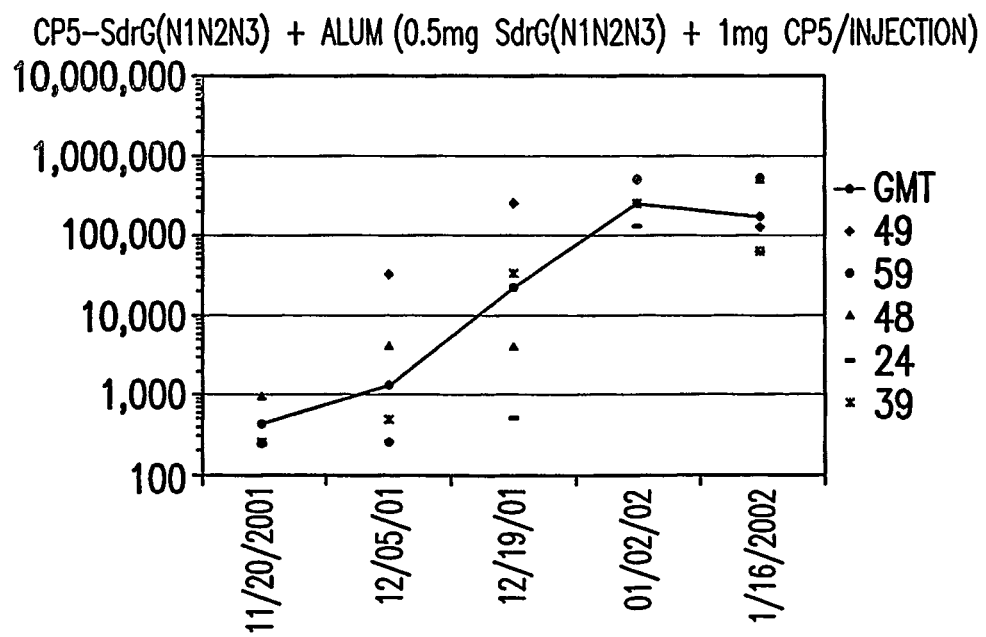
Figure 19E:
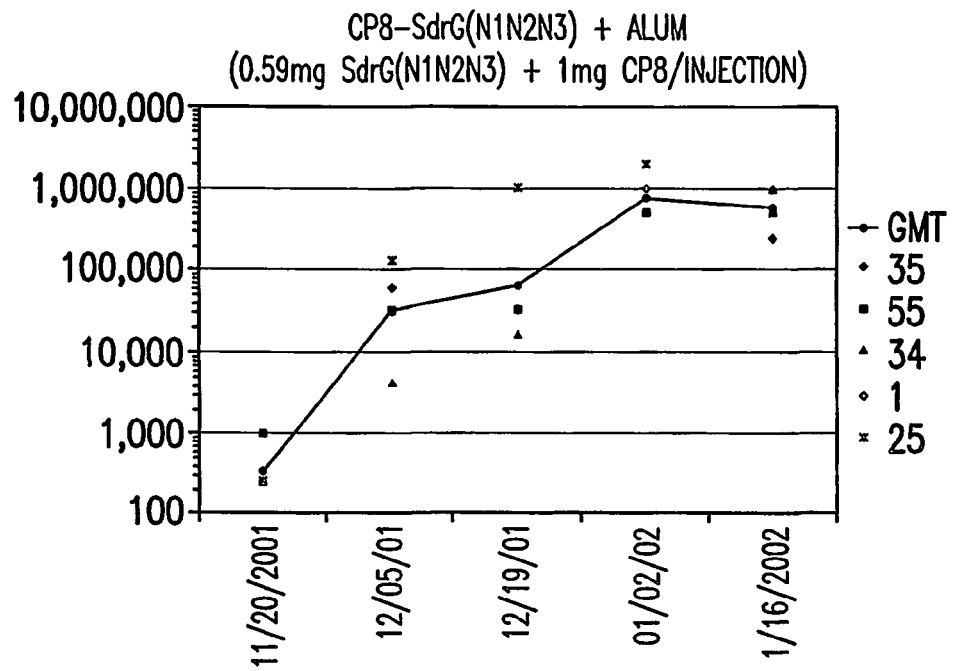
Figure 19F:
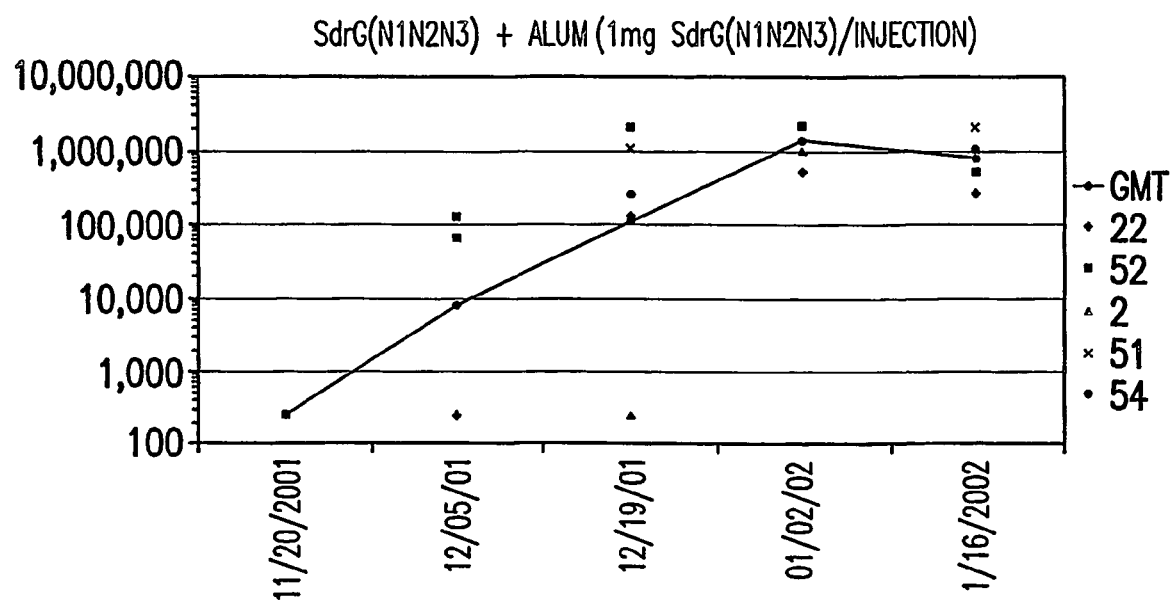
Figure 20A:
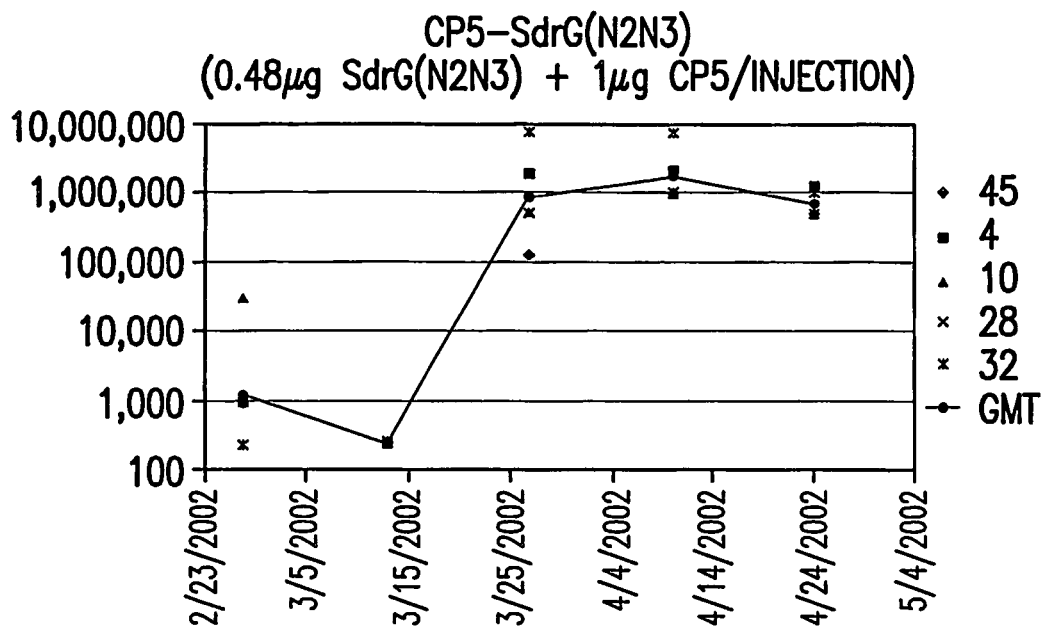
FIGS. 20A-F show the immune response to conjugated and unconjugated *S. epidermidis* SdrG (N2N3) with and without adjuvant.
Figure 20B:
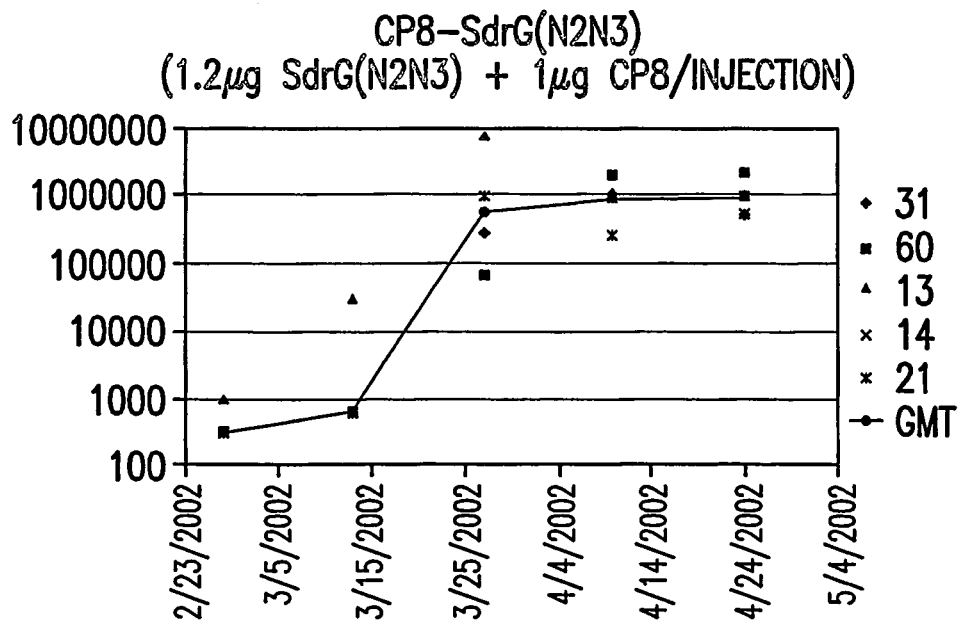
Figure 20C:
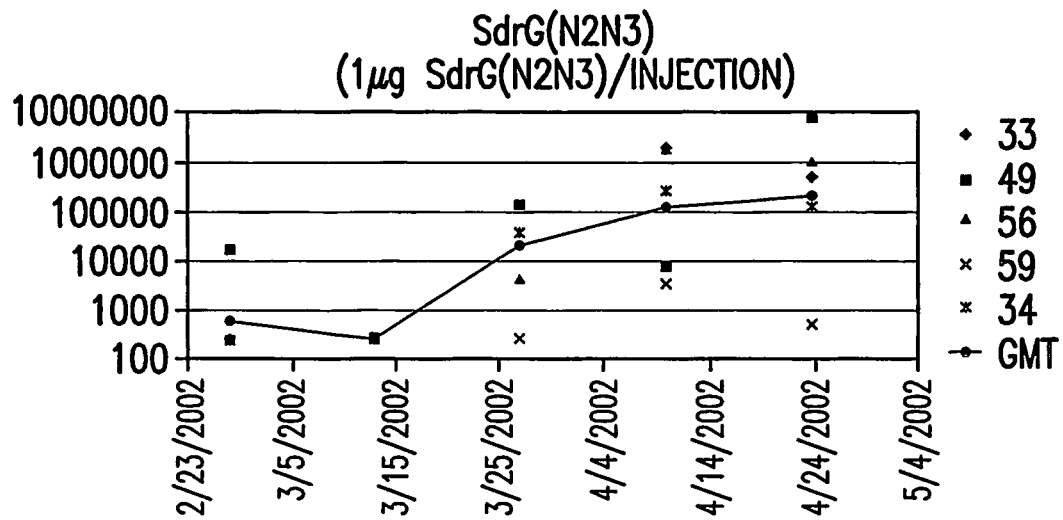
Figure 20D:
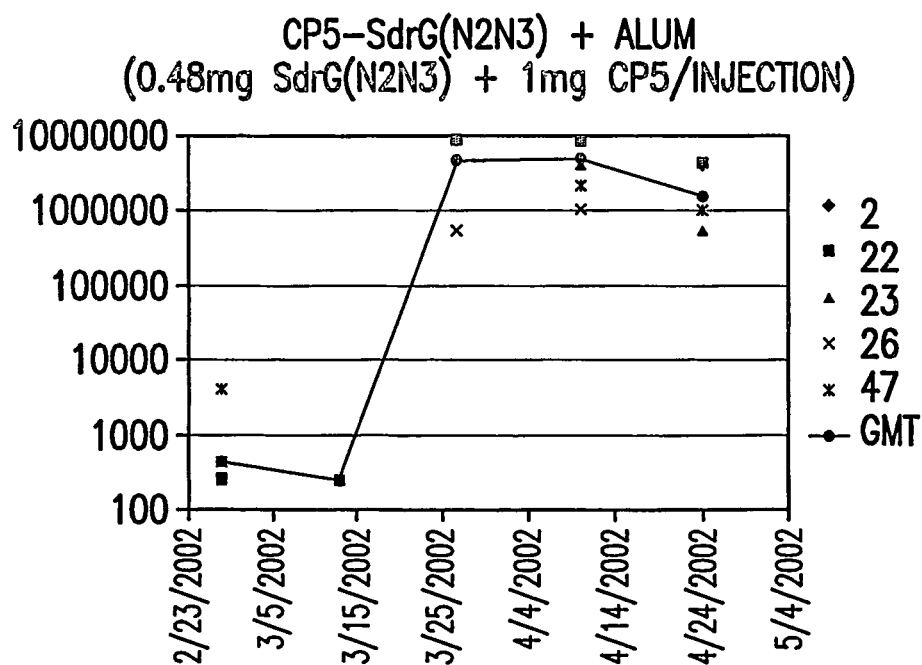
Figure 20E:
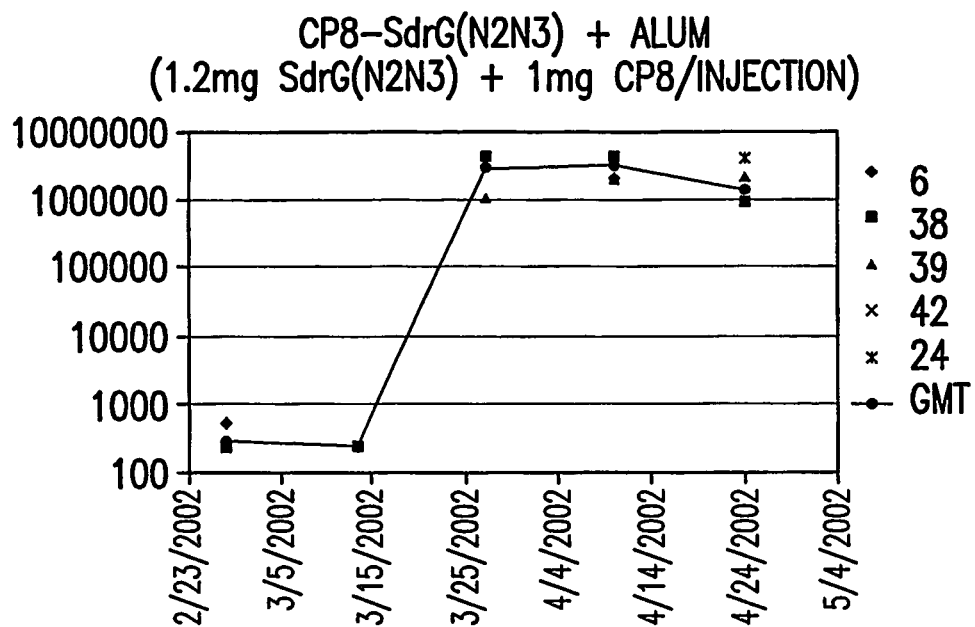
Figure 20F:
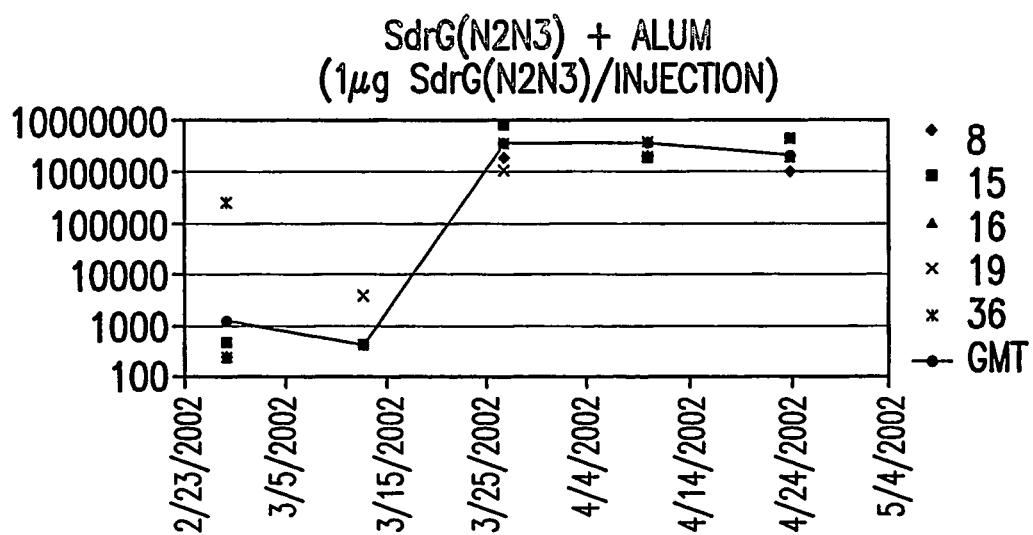

*S. aureus* CP5 and CP8 polysaccharides were separately linked to a surface adhesin carrier protein provided herein through a thioether bond after introduction of a thiol group containing a linker to the polysaccharide and a haloacetyl group to the protein carrier. Bromoacetyl groups were introduced into the surface adhesin protein by reaction of the amine groups with the N-hydroxysuccinimide ester of bromoacetic acid (FIG. 7). To generate thiolated CP, the carbodiimide-activated carboxylate groups of N-acetylmannosaminouronic acid in capsular polysaccharide were coupled to the hydrazide group of the sulfhydryl-reactive hydrazide heterobifunctional linker 3-(2-pyridyldithio)-propionyl hydrazide (PDPH, FIG. 8). Thiols of PDPH-thiolated CP, generated by reduction with dithiothreitol (DTT) and purified by SEC on a Sephadex G25 column, reacted with bromoacetyl groups of activated protein resulting in a covalent thioether linkage formed by bromine displacement between CP and the protein (FIG. 9). Unreacted bromoacetyl groups were "capped" with cysteamine hydrochloride (2-aminoethanethiol hydrochloride). The reaction mixture was then concentrated on an Amicon XM 100 membrane.

Example 5

Characterization of *S. aureus* CP5- and CP8 Surface Adhesin Carrier Protein Conjugate Immunogenic Compositions The conjugate immunogenic compositions were analyzed for CP and surface adhesin carrier protein contents by quantitation of CP by HPAEC-PAD chromatography on a Carbo Pac-PA1 column after hydrolysis with 4N trifluoroacetic acid (TFA). The protein content was determined by Lowry colorimetric assay. The molecular weights of the conjugate immunogenic compositions were determined by a combination of size exclusion chromatography and multiangle laser light scattering (MALLS). The results are reported in Tables 2 and 3. The antigenicity of conjugated CP and surface adhesin proteins was determined by double immunodiffusion (FIGS. 10-13) and by dot blot analysis (FIG. 14). The results showed that conjugation of CP to surface adhesin proteins did not alter antigenicity of either CP or protein. The conjugation of CP to protein was confirmed in dot blot assay by the ability of the conjugate to bind to a nitrocellulose membrane. The unconjugated CP did not bind a nitrocellulose membrane.

Example 6

Immunogenicity of CP-surface Adhesin Carrier Protein Conjugate Immunogenic Compositions in Mice Conjugate immunogenic compositions were tested for the ability to induce IgG responses to CP5 and CP8 and the surface adhesin protein carrier. Swiss-Webster mice were immunized subcutaneously (SC) three times in two-week intervals with a 1 microgram dose (based on CP). The immunogenicity of the conjugate immunogenic compositions was tested with and without 100 micrograms of aluminum phosphate as an adjuvant. Individual protein immunogenic composition candidates were evaluated as well using a similar protocol. The immune response to S. aureus CPs and surface adhesin protein was assayed one week after each injection by standard antigen ELISA (see Examples 7 and 8 below).

Example 7

CPs' Antibody Response in Mice Immunized with S. aureus CP5 and CP8-Surface Adhesin Carrier Protein Conjugate Immunogenic Compositions The results (FIGS. 15 and 16) show that covalent attachment of CPs to surface adhesin proteins resulted in the induction of a capsular polysaccharide (CP)-specific IgG response. This demonstrates that the CP T-cell independent immune response was converted to a T-cell dependent immune response after the coupling of the CP to the surface adhesin carrier protein. Adsorption of the conjugate immunogenic compositions to aluminum phosphate increased antibody titers to CP by approximately 10-fold, with the exception of the mice administered SdrG (N2N3) as the protein carrier. Adsorption of CP5- and CP8-SdrG (N2N3) conjugates to the adjuvant did not result in an increase of immune response to CPs, though the CPs' antibody response was as good as to the other surface adhesin protein conjugates mixed (but not adsorbed) with the adjuvant in the study. Deletion of the N1 domain of ClfA and SdrG did not have an effect on the carrier properties of these proteins.

Example 8

Surface Adhesin Protein Antibody Response in Mice Vaccinated with S. aureus CP5 and CP8-Surface Adhesin Carrier Protein Conjugates Conjugated surface adhesin proteins induced similar titers of surface adhesin protein-specific antibodies compared with the unconjugated ones (FIGS. 17-20). This confirms that antigenic epitopes were not modified by the conjugation of surface adhesin protein to CP. Adsorption of the unconjugated ClfA or CP-ClfA conjugates to aluminum phosphate resulted in increased ClfA antibody titers in mice compared with the mice immunized with the same immunogenic compositions without adjuvant. The mice immunized with unconjugated SdrG responded with lower SdrG antibody titers compared with mice immunized with CP-SdrG conjugate immunogenic compositions. Adsorption of the unconjugated SdrG to aluminum phosphate resulted in the increase of SdrG antibody titers compared to the levels induced by CP-SdrG conjugates administered without alum. Adsorption of the CP-SdrG conjugates to alum did not increase the SdrG antibody titers.

Example 9

Recognition of CPs and Surface Adhesin Carrier Protein Expressed on Live Bacteria by CP-Surface Adhesin Protein Conjugate-Induced Antibodies The binding of the antibodies induced by CP-surface adhesin protein conjugates in mice to live bacteria was tested by Flow cytometry analysis. The S. aureus strains employed in the assay are shown in Table 4. For analysis of the antibodies induced to SdrG conjugates the L. lactis expressing SdrG was used. The results show (Tables 5 and 6) that both capsular polysaccharide-specific antibodies and ClfA- or SdrG-specific antibodies induced by CP5 and CP8-surface adhesin protein conjugates bound to the live strains expressing corresponding antigens. This shows that conjugation of CP to surface adhesin protein does not alter the immune response towards naturally expressed epitopes present on CP and surface adhesin protein antigens.

Example 10

Flow Cytometric Analysis Method

The S. aureus strains used were as follows: Newman, a ClfA knockout mutant of Newman (Newman ClfA::emr) and Wright (ATCC 49525). To maximize ClfA expression, S. aureus bacteria were grown to stationary phase in tryptic soy broth. To maximize capsule expression, S. aureus bacteria were grown overnight on Columbia 2% NaCl agar (BD Microbiology, Sparks, Md.). The Newman ClfA::emr strain was grown in the presence of 5 µg/ml erythromycin to maintain the knock-out mutation. A recombinant Lactococcus lactis (L. Lactis) strain expressing SdrG was used to evaluate SdrG antigen recognition. The L. lactis strain was grown to late exponential phase in M17 broth in the presence of 5 µg/ml erythromycin.

All bacterial cultures were harvested, washed twice in 10 ml of cold 1×PBS (Invitrogen Corp., Rockville, Md.) and stored on ice prior to analysis. Bacterial concentrations were adjusted with 1×PBS to $OD_{600\ nm}$=2.0 using a UV-Visible Recording Spectrophotometer (Ultrospec 3000, Pharmacia Biotech, Cambridge, England). To eliminate non-specific and Protein A mediated binding of mouse IgG to the cell surface, all of the bacterial preparations were incubated for 30 minutes on ice in 10 ml of a 1:50 dilution (2.32 mg IgG) of Rabbit IgG (Sigma, St. Louis, Mo.) in 1×PBS (Invitrogen Corp., Rockville, Md.). To evaluate Type 8 capsule recognition in the absence of ClfA binding, ClfA epitopes were blocked on *S. aureus* strain Wright by an additional 30 min incubation with a high titer ClfA specific rabbit antiserum (Inhibitex, Alpharetta, Ga.) (1:100 dilution). Following the blocking incubations, bacteria were washed twice in 10 ml cold 1×PBS by centrifugation at 3000 rpm for 10 minutes. Bacterial pellets were resuspended in 2.5% BSA in 1×PBS (Invitrogen Corp., Rockville, Md.) (PBSA) and stored on ice.

The assay was performed in titertubes (BioRad Labs, Hercules, Calif.). Prebleeds and high titer antiserum from test animals were diluted in PBSA and 0.5 ml of each serum dilution was added to the appropriate tubes containing 20 μl of the bacterial suspension. All tubes were vortexed and incubated on ice for 30 minutes. Following the incubation, each tube was vortexed and then centrifuged at 3000 RPM for 10 minutes. The bacteria pellets were washed twice in 0.5 ml of cold PBSA. Each pellet was resuspended in 0.5 ml of a 1:200 dilution of PE conjugated F(ab')$_2$ fragment of anti-mouse IgG (H&L) (Rockland Labs, Gilbertsville, Pa.). The bacteria were resuspended and mixed by vortexing. The tubes were incubated on ice for 30 minutes vortexing twice at fifteen-minute intervals. Following this incubation, the bacteria were washed twice with a final resuspension in PBSA. The tubes were stored on ice until FACS analysis.

Each titertube was transferred to a 12×75 mm polystyrene tube and analyzed using a B-D FACSCalibur (BD Biosciences, Mansfield, Mass.) flow cytometer. Results were scored positive if the fluorescence intensity for a given antiserum was greater than the signal obtained with pre-bleeds at the same dilution. The results are shown in Table 7.

It should be understood that the foregoing discussion and examples merely present a detailed description of certain embodiments. It therefore should be apparent to those of ordinary skill in the art that various modifications and equivalents can be made without departing from the spirit and scope of the invention.

All journal articles, other references, patents and patent applications that are identified in this patent application are incorporated by reference in their entirety.

TABLE 1

Characterization of purified *S. aureus* polysaccharides:

| Polysaccharide | Protein (amino acid analysis) (%; w/w) | Nucleic Acids (%; w/w) | MW (g/mol) |
|---|---|---|---|
| CP5 | 1.1 | 0.05 | $5.1 \times 10^4$ |
| CP8 | 0.79 | 0.14 | $4.5 \times 10^4$ |

TABLE 2

Characteristics of *S. aureus* CP5 and CP8-surface adhesin protein (His+) conjugate immunogenic compositions.

| Immunogenic Composition | CP (mg/ml) | surface adhesin protein (mg/ml) | Ratio (w/w) (CP/surface adhesin protein) | MW (g/mol) |
|---|---|---|---|---|
| CP8-Clf40 (N1N2N3) | 0.083 | 0.14 | 0.6:1 | $2.67 \pm 0.2 \times 10^5$ |
| CP5-Clf40 (N1N2N3) | 0.102 | 0.183 | 0.55:1 | $2.33 \pm 0.3 \times 10^5$ |
| CP8-Clf41 (N2N3) | 0.67 | 0.44 | 1.5:1 | $1.78 \pm 1.1 \times 10^5$ |
| CP5-Clf41 (N2N3) | 0.43 | 0.40 | 1:1 | $1.30 \pm 0.4 \times 10^5$ |
| CP8-SdrG (N1N2N3) | 0.59 | 0.35 | 1.68:1 | $1.54 \pm 0.5 \times 10^5$ |
| CP5-SdrG (N1N2N3) | 0.68 | 0.34 | 2:1 | $2.01 \pm 1.4 \times 10^5$ |
| CP8-SdrG (N2N3) | 0.124 | 0.15 | 0.83:1 | $3.98 \pm 0.2 \times 10^5$ |
| CP5-SdrG (N2N3) | 0.125 | 0.059 | 2.1:1 | $3.12 \pm 0.2 \times 10^5$ |

TABLE 3

Characteristics of *S. aureus* CP5 and CP8-surface adhesin protein (His) conjugate immunogenic compositions.

| Immunogenic Composition | CP (mg/ml) | surface adhesin protein (mg/ml) | Ratio (w/w) (CP/surface adhesin protein) | MW (g/mol) |
|---|---|---|---|---|
| CP5-SdrG (N2N3)(His-) | 0.26 | 0.32 | 0.81:1 | $1.18 \pm 0.1 \times 10^5$ |
| CP8-SdrG (N2N3)(His-) | 0.24 | 0.5 | 0.48:1 | $2.39 \pm 0.1 \times 10^5$ |
| CP5-FnBPA | 0.085 | 0.135 | 0.63:1 | $7.73 \pm 0.2 \times 10^5$ |
| CP8-FnBPA | 0.089 | 0.16 | 0.56:1 | $9.83 \pm 0.3 \times 10^5$ |

TABLE 4

Strains Used For Antisera Recognition of Native Antigens by Flow Cytometry.

| Strain | Capsule Type | Protein Type |
|---|---|---|
| S. aureus Newman Wild Type | CP5 | ClfA positive |
| S. aureus Newman ClfA::emr | CP5 | ClfA knockout |
| S. aureus ATCC 49525 (Wright) | CP8 | ClfA positive |
| S. aureus ATCC 49521 (Lowenstein) | CP5 | ClfA positive |
| L. lactis SdrG | None | SdrG positive |

TABLE 5

Labeling of the bacterial strains with CP5- and CP8- ClfA (N2N3) Conjugate Antisera by Flow Cytometry.

| Strain | Antigen Expressed | αCP5-ClfA (N2N3) | αCP8-ClfA (N2N3) |
|---|---|---|---|
| S. aureus Newman ClfA (-) Mutant | CP5 | +(276.6) | -(2.58) |
| S. aureus ATCC 49525 (ClfA Blocked) | CP8 | -(1.77) | +(159.08) |

| Strain | Antigen Expressed | αCP5-ClfA (N2N3) | αCP8-ClfA (N2N3) | αClfA (N2N3) |
|---|---|---|---|---|
| S. aureus Newman WT | ClfA CP5 | +(281.8) | +(253.3) | +(169.1) |
| S. aureus ATCC 49525 | ClfA CP8 | +(23.34) | +(82.81) | +(85.18) |

TABLE 6

Labeling of the bacterial strains with CP5- and CP8- SdrG (N1N2N3) Conjugate Antisera by Flow Cytometry.

| Strain | Antigen | αCP8-SdrG (N1N2N3) | αCP5-SdrG (N1N2N3) |
|---|---|---|---|
| S. aureus Newman WT | CP5 | -(1.49) | +(128.29) |
| S. aureus ATCC 49525 | CP8 | +(120.86) | -(1.56) |

| Strain | Antigen | αCP8-SdrG (N1N2N3) | αCP5-SdrG (N1N2N3) | αSdrG (N1N2N3) |
|---|---|---|---|---|
| L. lactis | SdrG (N1N2N3) | +(478.27) | +(518.31) | +(511.73) |

TABLE 7

Summary of Flow Cytometric Analysis

| Immunizing Conjugate* | Bacteria Preparation | Relevant Antigen(s) | Result |
|---|---|---|---|
| CP5-ClfA | Newman | ClfA and CP5 | + |
| | Newman ClfA::emr | CP5 | + |
| | Wright | ClfA and CP8 | + |
| | Wright ClfA Blocked | CP8 | − |
| CP8-ClfA | Newman | ClfA and CP5 | + |
| | Newman ClfA::emr | CP5 | − |
| | Wright | ClfA and CP8 | + |
| | Wright ClfA Blocked | CP8 | + |
| CP5-SdrG | Newman | CP5 | + |
| | Wright | CP8 | − |
| | L. lactis-SdrG | SdrG | + |
| CP8-SdrG | Newman | CP5 | − |
| | Wright | CP8 | + |
| | L. lactis-SdrG | SdrG | + |

* ClfA = N1, N2, N3 or N2, N3 regions of ClfA A domain. SdrG = N1, N2, N3 or N2, N3 regions of SdrG A domain.

REFERENCES

Anonyomous (1997). "National Nosocomial Infections Surveillance (NNIS) Report, Data Summary from October 1986-April 1997, Issued May 1997." *Am J Infect Control* 25: 477487.

Arbeit, R. D., W. W. Karakawa, et al. (1984). "Predominance of two newly described capsular polysaccharide types among clinical isolates of *Staphylococcus aureus*." *Diagn Microbiol Infect Dis* 2(2): 85-91.

Boyce, J. M. (1997). Epidemiology and Prevention of Nosocomial Infections. *The Staphylococci in Human Disease*. K. B. Crossley and G. L. Archer, Churchill Livingstone: 309-329.

Chatwal et al. (1987) *Infect. Immun.* 55:1878-1883.

Cheung et al. (1991) *J. Clin. Invest.* 87:2236-2245.

Eidhin, et al. (1998) "Clumping Factor B (ClfB, a new surface-located fibrinogen-binding adhesin of *Staphylococcus aureus*." *Molecular Microbiology* 30(2) (Oct):245-257.

Essawi, T., T. Na'was, et al. (1998). "Molecular, antibiogram and serological typing of *Staphylococcus aureus* isolates recovered from Al-Makased Hospital in East Jerusalem." *Tropical Medicine & International Health* 3(7): 576-583.

Fattom, A., X. Li, et al. (1995). "Effect of conjugation methodology, carrier protein, and adjuvants on the immune response to *Staphylococcus aureus* capsular polysaccharides." *Vaccine* 13(14): 1288-1293.

Fattom, A., R. Schneerson, et al. (1990). "Synthesis and immunologic properties in mice of vaccines composed of *Staphylococcus aureus* type 5 and type 8 capsular polysaccharides conjugated to *Pseudomonas aeruginosa* exotoxin A." *Infection & Immunity* 58(7): 2367-2374.

Fattom, A., R. Schneerson, et al. (1993). "Laboratory and clinical evaluation of conjugate vaccines composed of *Staphylococcus aureus* type 5 and type 8 capsular polysaccharides bound to *Pseudomonas aeruginosa* recombinant exoprotein A." *Infect Immun* 61(3): 1023-32.

Fattom, A., J. Shiloach, et al. (1992). "Comparative immunogenicity of conjugates composed of the *Staphylococcus aureus* type 8 capsular polysaccharide bound to carrier proteins by adipic acid hydrazide or N-succinimidyl-3-(2-pyridyidithio) propionate." *Infection & Immunity* 60(2): 584-9.

Fattom, A. I. and R. Naso (1996). "Staphylococcal vaccines: a realistic dream." *Annals of Medicine* 28(1): 43-6.

Fattom, A. I. and R. Naso (1996). "*Staphylococcus aureus* vaccination for dialysis patients—an update." *Advances in Renal Replacement Therapy* 3(4): 302-8.

Fattom, A. I., J. Sarwar, et al. (1996). "A *Staphylococcus aureus* capsular polysaccharide (CP) vaccine and CP-specific antibodies protect mice against bacterial challenge." *Infection & Immunity* 64(5): 1659-65.

Fey, P. D., J. S. Ulphani, et al. (1999). "Characterization of the relationship between polysaccharide intercellular adhesin and hemagglutination in *Staphylococcus epidermidis*." *Journal of Infectious Diseases* 179(6): 1561-4.

Foster, T. J. and M. Hook (1998). "Surface protein adhesins of *Staphylococcus aureus*." *Trends in Microbiology* 6(12): 484-8.

Fournier, J. M., K. Hannon, et al. (1987). "Isolation of type 5 capsular polysaccharide from *Staphylococcus aureus*." *Ann Inst Pasteur Microbiol* 138(5): 561-567.

Fournier, J. M., W. F. Vann, et al. (1984). "Purification and characterization of *Staphylococcus aureus* type 8 capsular polysaccharide." *Infect Immun* 45(1): 87-93.

Gilbert, F. B., B. Poutrel, et al. (1994). "Immunogenicity in cows of *Staphylococcus aureus* type 5 capsular polysaccharide-ovalbumin conjugate." *Vaccine* 12(4): 369-74.

Haley, R. W., D. H. Culver, et al. (1985). "The nation-wide nosocomial infection rate: a new need for vital statistics." *Am. J. Epidemiol.* 121: 159.

Hienz, S. A., T. Schennings, et al. (1996). "collagen binding of *Staphylococcus aureus* is a virulence factor in experimental endocarditis." *Journal of Infectious Diseases* 174 (1): 83-88.

Herrmann et al. (1993) *J. Infect. Dis.* 167:312-322.

Inodot, acute, et al. (1998). "Clumping factor B (ClfB), a new surface-located fibrinogen-binding adhesin of *staphylococcus aureus* [In Process Citation]." *Mol. Microbiol.* 30(2): 245-257.

Jonsson, K., et al. (1991) Eur. J Biochem. 202:1041-1048.

Josefsson, E., K. W. McCrea, et al. (1998). "Three new members of the serine-aspartate repeat protein multigene family of *Staphylococcus aureus*." *Microbiology* 144(Pt 12): 3387-3395.

Karakawa, W. W. (1992). "The role of capsular antigens in *Staphylococcus aureus* immunity [editorial]." *Zentralblatt fur Bakteriologie* 277(4): 415-418.

Karakawa, W. W., J. M. Fournier, et al. (1985). "Method for the serological typing of the capsular polysaccharides of *Staphylococcus aureus*." *J Clin Microbiol* 22(3): 445-7.

Karakawa, W. W., A. Sutton, et al. (1988). "Capsular antibodies induce type-specific phagocytosis of capsulated *Staphylococcus aureus* by human polymorphonuclear leukocytes." *Infect Immun* 56(5): 1090-5.

Karakawa, W. W. and W. F. Vann (1982). "Capsular polysaccharides of *Staphylococcus aureus*." *Semin. Infect. Dis.* 4: 285-293.

Kuusela, P. (1978). *Nature* 276:718-720.

Lee, C. Y. and G. B. Pier (1997). Vaccine Based Strategies for Prevention of Staphylococcal Disease. *The Staphylococci in human disease*. K. B. Crossley and G. L. Archer. New York, Churchill Livingstone: 649-650.

Lee, J. C. (1996). "The prospects for developing a vaccine against *Staphylococcus aureus*." *Trends Microbiol* 4(4): 162-6.

Lee, J. C., J. S. Park, et al. (1997). "Protective efficacy of antibodies to the *Staphylococcus aureus* type 5 capsular polysaccharide in a modified model of endocarditis in rats." *Infect Immun* 65(10): 4146-51.

Lee, J. C., N. E. Perez, et al. (1988). "Purified capsular polysaccharide-induced immunity to *Staphylococcus aureus* infection." *J Infect Dis* 157(4): 723-730.

Mack, D., W. Fischer, et al. (1996). "The intercellular adhesin involved in biofilm accumulation of *Staphylococcus epidermidis* is a linear beta-1,6-linked glucosaminoglycan: purification and structural analysis." *Journal of Bacteriology* 178(1): 175-183.

Maira-Litran, T., A. Kropec, et al. (2002). "Immunochemical properties of the staphylococcal poly-N-acetylglucosamine surface polysaccharide." *Infection & Immunity*. 70(8): 4433-4440.

Mamo, W., M. Boden, et al. (1994). "Vaccination with *Staphylococcus aureus* fibrinogen binding proteins (FgBPs) reduces colonisation of *S. aureus* in a mouse mastitis model." *FEMS Immunol Med Microbiol* 10(1): 47-53.

Mamo, W., P. Jonsson, et al. (1994). "Vaccination against *Staphylococcus aureus* mastitis: immunological response of mice vaccinated with fibronectin-binding protein (FnBP-A) to challenge with *S. aureus*." *Vaccine* 12(11): 988-92.

Mamo, W., P. Jonsson, et al. (1995). "Opsonization of *Staphylococcus aureus* with a fibronectin-binding protein antiserum induces protection in mice." *Microb Pathog* 19(1): 49-55.

McDevitt et al. (1994) Mol. Microbiol. 11: 237-248.

McDevitt et al. (1995) Mol. Microbiol. 16:895-907.

McDevitt et al. (1997) *Eur. J. Biochem.* 247:416-424.

McKenney, D., K. L. Pouliot, et al. (1999). "Broadly protective vaccine for *Staphylococcus aureus* based on an in vivo-expressed antigen." *Science* 284(5419): 1523-1527.

Moreau, M., J. C. Richards, et al. (1990). "Structure of the type 5 capsular polysaccharide of *Staphylococcus aureus*." *Carbohydr Res* 201(2): 285-97.

Moreillon, P., J. M. Entenza, et al. (1995). "Role of *Staphylococcus aureus* coagulase and clumping factor in pathogenesis of experimental endocarditis." *Infect Immun* 63(12): 473843.

Nada, T., S. Ichiyama, et al. (1996). "Types of methicillin-resistant *Staphylococcus aureus* associated with high mortality in patients with bacteremia." *European Journal of Clinical Microbiology & Infectious Diseases* 15(4): 340-3.

Na'was, T., A. Hawwari, et al. (1998). "Phenotypic and genotypic characterization of nosocomial *Staphylococcus aureus* isolates from trauma patients." *Journal of Clinical Microbiology* 36(2): 414420.

Nilsson, I. M., J. C. Lee, et al. (1997). "The role of staphylococcal polysaccharide microcapsule expression in septicemia and septic arthritis." *Infection & Immunity* 65(10): 4216-4221.

Nilsson, I. M., J. M. Patti, et al. (1998). "Vaccination with a recombinant fragment of collagen adhesin provides protection against *Staphylococcus aureus*-mediated septic death." *J Clin Invest* 101(12): 2640-2649.

O'Connell (1998) *J. Biol. Chem.*, in press.

Palma, M., S. Nozohoor, et al. (1996). "Lack of the extracellular 19-kilodalton fibrinogen-binding protein from *Staphylococcus aureus* decreases virulence in experimental wound infection." *Infect Immun* 64(12): 5284-5289.

Patti, J., et al. (1992) *J Biol. Chem.* 267:4766-4772.

Patti, J. et al. (1993) *Biochemistry* 32:11428-11435.

Patti, J. M., B. L. Allen, et al. (1994). "MSCRAMM-mediated adherence of microorganisms to host tissues." *Annu Rev Microbiol* 48:585-617.

Patti, J. and Hook, M. (1994) *Cur Orin Cell Biol.*, 6:752-758.

Patti, J. et al. (1995) J of Biol Chem. 270:12005-12011, 1995.

Reynaud-Rondier, L., A. Voiland, et al. (1991). "Conjugation of capsular polysaccharide to alpha-haemolysin from *Staphylococcus aureus* as a glycoprotein antigen." *FEMS Microbiol Immunol* 3(4): 193-199.

Rupp, M. E. and P. D. Fey (2001). "In vivo models to evaluate adhesion and biofilm formation by *Staphylococcus epidermidis*." *Methods in Enzymology* 336: 206-215.

Rupp, M. E., P. D. Fey, et al. (2001). "Characterization of the Importance of *Staphylococcus epidermidis* Autolysin and Polysaccharide Intercellular Adhesin in the Pathogenesis of Intravascular Catheter-Associated Infection in a Rat Model." *J Infect Dis* 183(7): 1038-1042.

Rupp, M. E., J. S. Ulphani, et al. (1999). "Characterization of the importance of polysaccharide intercellular adhesin/hemagglutinin of *Staphylococcus epidermidis* in the pathogenesis of biomaterial-based infection in a mouse foreign body infection model." *Infection & Immunity* 67(5): 2627-2632.

Rupp, M. E., J. S. Ulphani, et al. (1999). "Characterization of *Staphylococcus epidermidis* polysaccharide intercellular adhesin/hemagglutinin in the pathogenesis of intravascular catheter-associated infection in a rat model." *Infection & Immunity* 67(5): 2656-2659.

Ryden et al. (1987) *Lancet*, 11:515-518.

Schennings, T., A. Heimdahl, et al. (1993). "Immunization with fibronectin binding protein from *Staphylococcus aureus* protects against experimental endocarditis in rats." *Microb Pathog* 15(3): 227-36.

Shinefield, H., S. Black, et al. (2002). "Use of a *Staphylococcus aureus* conjugate vaccine in patients receiving hemodialysis." *N Engl J Med* 346(7): 491-6.

Sompolinsky, D., Z. Samra, et al. (1985). "Encapsulation and capsular types in isolates of *Staphylococcus aureus* from different sources and relationship to phage types." *J Clin Microbiol* 22(5): 828-34.

Storch, G. A. and L. Rajagopalan (1986). "Methicillin resistant *Staphylococcus aureus* bacteremia in children." *Pediatr. Infect. Dis.* 5: 59.

Switalski, L. M., J. M. Patti, et al. (1993). "A collagen receptor on *Staphylococcus aureus* strains isolated from patients with septic arthritis mediates adhesion to cartilage." *Molecular Microbiology* 7(1): 99-107.

Thakker, M., J. S. Park, et al. (1998). "*Staphylococcus aureus* serotype 5 capsular polysaccharide is antiphagocytic and enhances bacterial virulence in a murine bacteremia model." *Infect Immun* 66(11): 5183-9.

Thylefors, J. D., S. Harbarth, et al. (1998). "Increasing bacteremia due to coagulase-negative staphylococci: fiction or reality?" *Infection Control & Hospital Epidemiology* 19(8): 581-9.

Tojo, M., N. Yamashita, et al. (1988). "Isolation and characterization of a capsular polysaccharide adhesin from *Staphylococcus epidermidis* [published erratum appears in J Infect Dis 1988 July; 158(1):268]." *Journal of Infectious Diseases* 157(4): 713-22.

Vann, W. F., M. Moreau, et al. (1987). "Structure and immunochemistry of *Staphylococcus aureus* capsular polysaccharide." *UCLA Symp. Mol. Cell. Biol. New. Ser.* 64:187-198.

Vaudaux et al. (1989) J. Infect. Dis. 160:865-875.

Vaudaux et al. (1995) Infect. Immun. 63:585-590.

Weinstein, R. A. (1998). "Nosocomial infection update." *Emerg Infect Dis* 4(3): 416-20.

Welch, P. G., Fattom A., Moore J. Jr. et al. (1996) "Safety and immunogenicity of *Staphylococcus aureus* type 5 capsular polysaccharide-*Psuedomonas aeruginosa* recombinant exoprotein A conjugate vaccine in patients on hemodialysis." *J. Am Soc. Nephrol.* 7:247-253 [Abstract]

The invention claimed is:

1. An immunogenic polysaccharide-protein conjugate, comprising: at least one polysaccharide antigen derived from a nosocomial pathogen and at least one staphylococcal surface adhesin carrier protein,
   wherein the conjugate generates specific antibodies to both the polysaccharide antigen and the staphylococcal surface adhesin carrier protein, and
   wherein the polysaccharide antigen is an antigen from coagulase-negative staphylococci (CoNS), wherein the CoNS is *Staphylococcus epidermidis* (*S. epidermidis*).

2. An immunogenic polysaccharide-protein conjugate, comprising: an oligosaccharide fragment representing one or more antigenic epitopes of at least one polysaccharide antigen derived from a nosocomial pathogen and at least one staphylococcal surface adhesin carrier protein,
   wherein the conjugate generates specific antibodies to both the polysaccharide antigen and the staphylococcal surface adhesin carrier protein, and
   wherein the polysaccharide antigen is an antigen from coagulase-negative staphylococci (CoNS), wherein the CoNS is *Staphylococcus epidermidis* (*S. epidermidis*).

3. The conjugate of claim 1, wherein the polysaccharide antigen is polysaccharide intercellular adhesin (PIA), polysaccharide adhesin (PS/A), poly-N-succinyl β-1-6-glucosamine (PNSG), or poly-N-acetyl β-1-6-glucosamine (PNAG), expressed by *S. epidermidis*.

4. The conjugate of claim 1, wherein the staphylococcal surface adhesin carrier protein is selected from the group consisting of fibrinogen-binding protein, fibronectin-binding protein, collagen-binding protein, vitronectin-binding protein and combinations thereof.

5. The conjugate of claim 4, wherein the staphylococcal surface adhesin carrier protein is the fibronectin-binding protein of *S. aureus*.

6. The conjugate of claim 4, wherein the staphylococcal surface adhesin carrier protein is the collagen-binding protein of *S. aureus*.

7. The conjugate of claim 4, wherein the staphylococcal surface adhesin carrier protein is the vitronectin-binding protein of *S. aureus*.

8. The conjugate of claim 1, wherein the polysaccharide antigen is conjugated to the staphylococcal surface adhesin carrier protein through a linker.

9. The conjugate of claim 8, wherein the linker is 3-(2-pyridyldithio)-propionyl hydrazide (PDPH).

10. An immunogenic composition comprising the conjugate of claim 1 in an immunologically acceptable carrier or diluent.

11. The immunogenic composition of claim 10, further comprising an adjuvant.

12. The conjugate of claim 2, wherein the polysaccharide antigen is polysaccharide intercellular adhesin (PIA), polysaccharide adhesin (PS/A), poly-N-succinyl β-1-6-glucosamine (PNSG), or poly-N-acetyl β-1-6-glucosamine (PNAG), expressed by *S. epidermidis*.

13. The conjugate of claim 2, wherein the staphylococcal surface adhesin carrier protein is selected from the group consisting of fibrinogen-binding protein, fibronectin-binding protein, collagen-binding protein, vitronectin-binding protein and combinations thereof.

14. The conjugate of claim 13, wherein the staphylococcal surface adhesin carrier protein is the fibronectin-binding protein of *S. aureus*.

15. The conjugate of claim 13, wherein the staphylococcal surface adhesin carrier protein is the collagen-binding protein of *S. aureus*.

16. The conjugate of claim 13, wherein the staphylococcal surface adhesin carrier protein is the vitronectin-binding protein of *S. aureus*.

17. The conjugate of claim 2, wherein the polysaccharide antigen is conjugated to the staphylococcal surface adhesin carrier protein through a linker.

18. The conjugate of claim 17, wherein the linker is 3-(2-pyridyldithio)propionyl hydrazide (PDPH).

19. An immunogenic composition comprising the conjugate of claim 2 in an immunologically acceptable carrier or diluent.

20. The immunogenic composition of claim 19, further comprising an adjuvant.

21. An immunogenic polysaccharide-protein conjugate, comprising: at least one polysaccharide antigen derived from a nosocomial pathogen and at least one staphylococcal surface adhesin carrier protein,
   wherein the conjugate generates specific antibodies to both the polysaccharide antigen and the staphylococcal surface adhesin carrier protein, and
   wherein the polysaccharide antigen is an antigen from *Staphylococcus aureus* (*S. aureus*), or coagulase-negative staphylococci (CoNS), wherein the CoNS is *Staphylococcus epidermidis* (*S. epidermidis*) and
   wherein the polysaccharide antigen is polysaccharide intercellular adhesin (PIA), polysaccharide adhesin (PS/A), poly-N-succinyl β-1-6-glucosamine (PNSG), or poly-N-acetyl β-1-6-glucosamine (PNAG), expressed by *S. aureus* or *S. epidermidis*.

22. An immunogenic polysaccharide-protein conjugate, comprising: an oligosaccharide fragment representing one or more antigenic epitopes of at least one polysaccharide antigen derived from a nosocomial pathogen and at least one staphylococcal surface adhesin carrier protein,
   wherein the conjugate generates specific antibodies to both the polysaccharide antigen and the staphylococcal surface adhesin carrier protein, and
   wherein the polysaccharide antigen is an antigen from *Staphylococcus aureus* (*S. aureus*) or coagulase-negative staphylococci (CoNS), wherein the CoNS is *Staphylococcus epidermidis* (*S. epidermidis*); and
   wherein the polysaccharide antigen is polysaccharide intercellular adhesin (PIA), polysaccharide adhesin (PS/A), poly-N-succinyl β-1-6-glucosamine (PNSG), or poly-N-acetyl β-1-6-glucosamine (PNAG), expressed by *S. aureus* or *S. epidermidis*.

* * * * *

SEQUENCE LISTING

```
<160> NUMBER OF SEQ ID NOS: 3

<210> SEQ ID NO 1
<211> LENGTH: 18
<212> TYPE: DNA
<213> ORGANISM: Staphylococcus aureus
<220> FEATURE:
<221> NAME/KEY: modified_base
<222> LOCATION: (6)
<223> OTHER INFORMATION: a, c, g, or t
<220> FEATURE:
<221> NAME/KEY: modified_base
<222> LOCATION: (12)
<223> OTHER INFORMATION: a, c, g, or t

<400> SEQUENCE: 1
gaytcngayt cngayagy                                                    18

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus motif

<400> SEQUENCE: 2

Leu Pro Asp Thr Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus motif

<400> SEQUENCE: 3

Thr Tyr Thr Phe Thr Asp Tyr Val Asp
1               5
```